United States Patent
Mujica-Fernaud et al.

(10) Patent No.: US 9,978,949 B2
(45) Date of Patent: May 22, 2018

(54) MATERIALS FOR ELECTRONIC DEVICES

(71) Applicant: Merck Patent GmbH, Darmstadt (DE)

(72) Inventors: Teresa Mujica-Fernaud, Darmstadt (DE); Elvira Montenegro, Weinheim (DE); Frank Voges, Bad Duerkheim (DE); Jonas Valentin Kroeber, Frankfurt am Main (DE); Philipp Stoessel, Frankfurt am Main (DE)

(73) Assignee: Merck Patent GmbH (DE)

( * ) Notice: Subject to any disclaimer, the term of this patent is extended or adjusted under 35 U.S.C. 154(b) by 171 days.

(21) Appl. No.: 14/441,975

(22) PCT Filed: Oct. 18, 2013

(86) PCT No.: PCT/EP2013/003136
§ 371 (c)(1),
(2) Date: May 11, 2015

(87) PCT Pub. No.: WO2014/072017
PCT Pub. Date: May 15, 2014

(65) Prior Publication Data
US 2015/0295181 A1    Oct. 15, 2015

(30) Foreign Application Priority Data

Nov. 12, 2012   (EP) ..................... 12007665

(51) Int. Cl.
| | |
|---|---|
| *H05B 33/20* | (2006.01) |
| *H01L 51/50* | (2006.01) |
| *C09K 11/06* | (2006.01) |
| *C07D 409/12* | (2006.01) |
| *C07D 405/12* | (2006.01) |
| *C07D 311/96* | (2006.01) |
| *C07D 311/90* | (2006.01) |
| *H01L 51/00* | (2006.01) |
| *C08G 73/02* | (2006.01) |
| *C08G 75/00* | (2006.01) |

(52) U.S. Cl.
CPC ........ *H01L 51/0061* (2013.01); *C07D 311/90* (2013.01); *C07D 311/96* (2013.01); *C07D 405/12* (2013.01); *C07D 409/12* (2013.01); *C08G 73/0273* (2013.01); *C08G 75/00* (2013.01); *C09K 11/06* (2013.01); *H01L 51/006* (2013.01); *H01L 51/0052* (2013.01); *H05B 33/20* (2013.01); *C09K 2211/1011* (2013.01); *C09K 2211/1014* (2013.01); *H01L 51/0072* (2013.01); *H01L 51/0073* (2013.01); *H01L 51/0074* (2013.01); *H01L 51/0085* (2013.01); *H01L 51/0087* (2013.01); *H01L 51/5012* (2013.01); *H01L 51/5056* (2013.01); *H01L 51/5096* (2013.01); *Y02E 10/549* (2013.01)

(58) Field of Classification Search
CPC combination set(s) only.
See application file for complete search history.

(56) References Cited

U.S. PATENT DOCUMENTS

| | | |
|---|---|---|
| 5,387,725 A | 2/1995 | Walters et al. |
| 9,368,733 B2 | 6/2016 | Ryu et al. |
| 2003/0168970 A1 | 9/2003 | Tominaga et al. |

FOREIGN PATENT DOCUMENTS

| | | | |
|---|---|---|---|
| CN | 1397148 A | 2/2003 | |
| CN | 101440082 A | 5/2009 | |
| CN | 102229623 A | 11/2011 | |
| JP | H07502728 A | 3/1995 | |
| JP | 2002222697 A | 8/2002 | |
| JP | 2009191232 A | 8/2009 | |
| JP | 4843889 B2 | 12/2011 | |
| JP | 2016502500 A | 1/2016 | |
| KR | 20080037699 A | 4/2008 | |
| KR | 20120116838 A | 10/2012 | |
| KR | 20130007390 A * | 1/2013 | |
| KR | 20130140303 A | 12/2013 | |
| WO | WO 9309074 A2 * | 5/1993 | ............. C07B 37/04 |
| WO | WO-2014051232 A1 | 4/2014 | |

OTHER PUBLICATIONS

Chu et al. "Synthesis of spiro[fluorene-9,9'-xanthene] derivatives and their application as hole-transporting materials for organic light-emitting devices" Synth. Met. 2012 162, 614-620.*
Goodbrand et al. "Ligand-Accelerated Catalysis of the Ullmann Condensation: Application to Hole Conducting Trlarylamlnes" J. Org. Chem. 1999, 64, 670-674.*
Kim et al. KR 20130007390 A English Machine Translation [retrieved on Feb. 16, 2017]. Retrieved from KIPO.*
Qian, Y., et al., "A new spiro[fluorene-9,9'-xanthene]-based host material possessing no conventional hole- and electron-transporting units for efficient and low voltage blue PHOLED via simple two-step synthesis", Organic Electronics, 2012, vol. 13, pp. 22741-22746.
International Search Report for PCT/EP2013/003136 dated Dec. 13, 2013.
Japanese Office Action for Japanese Application No. 2015/541029, dated Jul. 11, 2017.

* cited by examiner

*Primary Examiner* — Amanda L Aguirre
(74) *Attorney, Agent, or Firm* — Drinker Biddle & Reath LLP

(57) ABSTRACT

The application relates to a compound of a formula (I) which is suitable for use as functional material in electronic devices.

11 Claims, No Drawings

MATERIALS FOR ELECTRONIC DEVICES

CROSS-REFERENCE TO RELATED APPLICATIONS

This application is a national stage application (under 35 U.S.C. § 371) of PCT/EP2013/003136, filed Oct. 18, 2013, which claims benefit of European Application No. 12007665.8, filed Nov. 12, 2012, both of which are incorporated herein by reference in their entirety.

The present application relates to a compound having a xanthene basic structure of the formula (I) below. The application furthermore relates to a process for the preparation of the compound of the formula (I) and to the use of the compound in an electronic device.

Electronic devices in the sense of this application are taken to mean so-called organic electronic devices which comprise organic semiconductor materials as functional materials. In particular, they are taken to mean organic electroluminescent devices (OLEDs) and other electronic devices which are mentioned below.

The structure of OLEDs in which organic semiconductors are employed as functional materials is described, for example, in U.S. Pat. No. 4,539,507, U.S. Pat. No. 5,151,629, EP 0676461 and WO 98/27136. In general, the term OLED is taken to mean electronic devices which comprise organic material and emit light on application of an electrical voltage.

In the case of electronic devices, in particular OLEDs, there is considerable interest in improving the performance data, in particular lifetime, efficiency and operating voltage. An entirely satisfactory solution has not yet been found regarding these points.

A major influence on the performance data of electronic devices is exerted by layers having a hole-transporting function, such as, for example, hole-injection layers, hole-transport layers, electron-blocking layers and emitting layers.

Novel materials having hole-transporting properties are continuously being sought for this purpose. They can be employed in the said layers as pure materials, as principal components or as secondary components in combination with further materials.

In hole-injecting layers, hole-transport layers and electron-blocking layers, materials having hole-transporting properties are typically employed as pure substances. However, they can also be employed in such layers as a mixture with a doped further material. In emitting layers, in particular in phosphorescent emitting layers, the materials having hole-transporting properties are in many cases employed as one of the principal components of the layer (matrix material, host material) in combination with further materials, for example emitter materials.

It is known from the prior art to employ triarylamines as materials having hole-transporting properties in the above-mentioned layers. These can be monotriarylamines, as described, for example, in JP 1995/053955, WO 2006/123667 and JP 2010/222268, or bis- or other oligoamines, as described, for example, in U.S. Pat. No. 7,504,163 or US 2005/0184657. Known examples of triarylamine compounds as materials having hole-transporting properties for OLEDs are, inter alia, tris-p-biphenylamine, N,N'-di-1-naphthyl-N,N'-diphenyl-1,1'-biphenyl-4,4'-diamine (NPB) and 4,4',4''-tris-(3-methylphenylphenylamino)triphenylamine (MTDATA).

The prior art discloses the use of xanthene compounds which are substituted by aryl groups as matrix materials for phosphorescent emitters in OLEDs (U.S. Pat. No. 7,014,925).

The prior art furthermore discloses compounds which have a xanthene basic structure and which carry arylamino groups. For example, JP 2009-191232 discloses xanthene-arylamine compounds as emitting compounds in OLEDs. Furthermore, CN 101440082 discloses xanthenediamine compounds which are employed as functional materials in the emitting layer in OLEDs.

Surprisingly, it has now been found that excellent performance data in electronic devices can be achieved using a xanthene compound of the formula (I), as defined below, which contains a single arylamino group.

The invention thus relates to a compound of a formula (I)

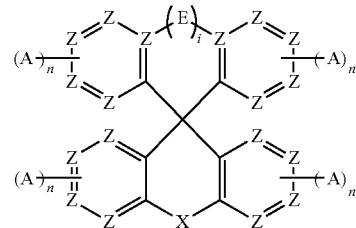

formula (I), where:
A is an arylamino group, optionally substituted by one or more radicals $R^1$, or a carbazole group, optionally substituted by one or more radicals $R^1$;
E is a single bond;
X is O or S;
Z is on each occurrence, identically or differently, $CR^2$ or N, where, in the case where a group A is bonded to it, the group Z is equal to C;
$R^1$ is on each occurrence, identically or differently, H, D, F, Cl, Br, I, C(=O)$R^3$, CN, Si($R^3$)$_3$, N($R^3$)$_2$, P(=O)($R^3$)$_2$, S(=O)$R^3$, S(=O)$_2R^3$, a straight-chain alkyl or alkoxy group having 1 to 20 C atoms or a branched or cyclic alkyl or alkoxy group having 3 to 20 C atoms or an alkenyl or alkynyl group having 2 to 20 C atoms, where the above-mentioned groups may each be substituted by one or more radicals $R^3$ and where one or more CH$_2$ groups in the above-mentioned groups may be replaced by —$R^3$C=C$R^3$—, —C≡C—, Si($R^3$)$_2$, C=O, C=N$R^3$, —C(=O)O—, —C(=O)N$R^3$—, N$R^3$, P(=O)($R^3$), —O—, —S—, SO or SO$_2$ and where one or more H atoms in the above-mentioned groups may be replaced by D, F, Cl, Br, I or CN, or an aromatic or heteroaromatic ring system having 5 to 30 aromatic ring atoms, which may in each case be substituted by one or more radicals $R^3$, or an aryloxy or heteroaryloxy group having 5 to 30 aromatic ring atoms, which may be substituted by one or more radicals $R^3$, where two or more radicals $R^1$ may be linked to one another and may form a ring;
$R^2$ is on each occurrence, identically or differently, H, D, F, Cl, Br, I, C(=O)$R^3$, CN, Si($R^3$)$_3$, P(=O)($R^3$)$_2$, S(=O)$R^3$, S(=O)$_2R^3$, a straight-chain alkyl or alkoxy group having 1 to 20 C atoms or a branched or cyclic alkyl or alkoxy group having 3 to 20 C atoms or an alkenyl or alkynyl group having 2 to 20 C atoms, where the above-mentioned groups may each be substituted by one or more radicals $R^3$ and where one or more CH$_2$ groups in the above-mentioned groups may be replaced by —R³C=CR³—, —C≡C—, Si(R³)₂, C=O, C=NR³, —C(=O)O—, —C(=O)NR³—, NR³, P(=O)(R³), —O—, —S—, SO or SO₂ and where one or more H atoms in the above-mentioned groups may be replaced by D, F, Cl, Br, I or CN, or an aromatic or heteroaromatic ring system having 5 to 30 aromatic ring atoms, which may in each case be substituted by one or more radicals R³, or an aryloxy or heteroaryloxy group having 5 to 30 aromatic ring atoms, which may be substituted by one or more radicals R³, where two or more radicals R² may be linked to one another and may form a ring;

R³ is on each occurrence, identically or differently, H, D, F, Cl, Br, I, C(=O)R⁴, CN, Si(R⁴)₃, N(R⁴)₂, P(=O)(R⁴)₂, S(=O)R⁴, S(=O)₂R⁴, a straight-chain alkyl or alkoxy group having 1 to 20 C atoms or a branched or cyclic alkyl or alkoxy group having 3 to 20 C atoms or an alkenyl or alkynyl group having 2 to 20 C atoms, where the above-mentioned groups may each be substituted by one or more radicals R⁴ and where one or more CH₂ groups in the above-mentioned groups may be replaced by —R⁴C=CR⁴—, —C≡C—, Si(R⁴)₂, C=O, C=NR⁴, —C(=O)O—, —C(=O)NR⁴—, NR⁴, P(=O)(R⁴), —O—, —S—, SO or SO₂ and where one or more H atoms in the above-mentioned groups may be replaced by D, F, Cl, Br, I or CN, or an aromatic or heteroaromatic ring system having 5 to 30 aromatic ring atoms, which may in each case be substituted by one or more radicals R⁴, or an aryloxy or heteroaryloxy group having 5 to 30 aromatic ring atoms, which may be substituted by one or more radicals R⁴, where two or more radicals R³ may be linked to one another and may form a ring;

R⁴ is on each occurrence, identically or differently, H, D, F or an aliphatic, aromatic or heteroaromatic organic radical having 1 to 20 C atoms, in which, in addition, one or more H atoms may be replaced by D or F; two or more substituents R⁴ here may be linked to one another and may form a ring;

i is equal to 0 or 1;

n is on each occurrence, identically or differently, 0 or 1, where the sum of all the indices n is equal to 1.

The following definitions and explanations apply:

An aryl group in the sense of this invention contains 6 to 60 aromatic ring atoms; a heteroaryl group in the sense of this invention contains 5 to 60 aromatic ring atoms, at least one of which is a heteroatom. The heteroatoms are preferably selected from N, O and S. This represents the basic definition. If other preferences are indicated in the description of the present invention, for example with respect to the number of aromatic ring atoms or the heteroatoms present, these apply.

An aryl group or heteroaryl group here is taken to mean either a simple aromatic ring, i.e. benzene, or a simple heteroaromatic ring, for example pyridine, pyrimidine or thiophene, or a condensed (annellated) aromatic or heteroaromatic polycycle, for example naphthalene, phenanthrene, quinoline or carbazole. A condensed (annellated) aromatic or heteroaromatic polycycle in the sense of the present application consists of two or more simple aromatic or heteroaromatic rings condensed with one another.

An aryl or heteroaryl group, which may in each case be substituted by the above-mentioned radicals and which may be linked to the aromatic or heteroaromatic ring system via any desired positions, is taken to mean, in particular, groups derived from benzene, naphthalene, anthracene, phenanthrene, pyrene, dihydropyrene, chrysene, perylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

An aryloxy group in accordance with the definition of the present invention is taken to mean an aryl group, as defined above, which is bonded via an oxygen atom. An analogous definition applies to heteroaryloxy groups.

An aromatic ring system in the sense of this invention contains 6 to 60 C atoms in the ring system. A heteroaromatic ring system in the sense of this invention contains 5 to 60 aromatic ring atoms, at least one of which is a heteroatom. The heteroatoms are preferably selected from N, O and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be connected by a non-aromatic unit (preferably less than 10% of the atoms other than H), such as, for example, an sp³-hybridised C, Si, N or O atom, an sp²-hybridised C or N atom or an sp-hybridised C atom. Thus, for example, systems such as 9,9'-spirobifluorene, 9,9'-diarylfluorene, triarylamine, diaryl ether, stilbene, etc., are also intended to be taken to be aromatic ring systems in the sense of this invention, as are systems in which two or more aryl groups are connected, for example, by a linear or cyclic alkyl, alkenyl or alkynyl group or by a silyl group. Furthermore, systems in which two or more aryl or heteroaryl groups are linked to one another via single bonds are also taken to be aromatic or heteroaromatic ring systems in the sense of this invention, such as, for example, systems such as biphenyl, terphenyl or diphenyl-triazine.

An aromatic or heteroaromatic ring system having 5-60 aromatic ring atoms, which may in each case also be substituted by radicals as defined above and which may be linked to the aromatic or heteroaromatic group via any desired positions, is taken to mean, in particular, groups derived from benzene, naphthalene, anthracene, benzanthracene, phenanthrene, benzophenanthrene, pyrene, chrysene, perylene, fluoranthene, naphthacene, pentacene, benzopyrene, biphenyl, biphenylene, terphenyl, terphenylene, quaterphenyl, fluorene, spirobifluorene, dihydrophenanthrene, dihydropyrene, tetrahydropyrene, cis- or trans-indenofluorene, truxene, isotruxene, spiro-truxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzo-pyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole, or combinations of these groups.

For the purposes of the present invention, a straight-chain alkyl group having 1 to 40 C atoms or a branched or cyclic alkyl group having 3 to 40 C atoms or an alkenyl or alkynyl group having 2 to 40 C atoms, in which, in addition, individual H atoms or $CH_2$ groups may be substituted by the groups mentioned above under the definition of the radicals, is preferably taken to mean the radicals methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cyclo-heptenyl, octenyl, cyclooctenyl, ethynyl, propynyl, butynyl, pentynyl, hexynyl or octynyl. An alkoxy or thioalkyl group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy, 2,2,2-trifluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexynylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio.

The formulation that two or more radicals may form a ring with one another is, for the purposes of the present application, intended to be taken to mean, inter alia, that the two radicals are linked to one another by a chemical bond. This is illustrated by the following scheme:

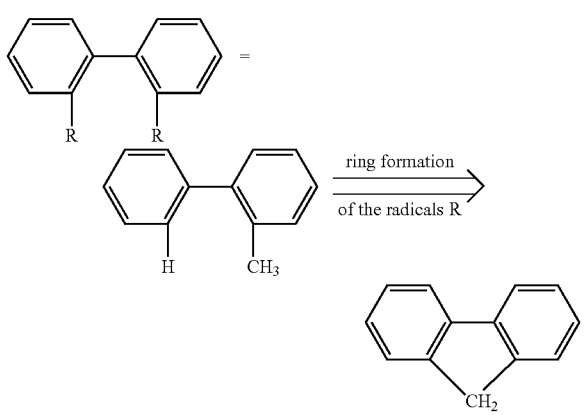

Furthermore, however, the above-mentioned formulation is also intended to be taken to mean that, in the case where one of the two radicals represents hydrogen, the second radical is bonded at the position to which the hydrogen atom was bonded, with formation of a ring. This is illustrated by the following scheme:

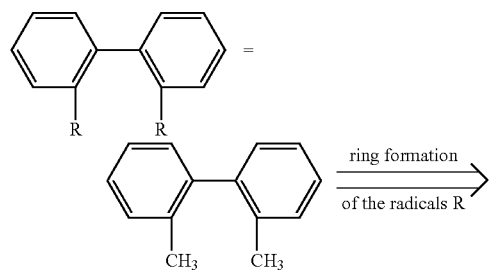

Regarding the indices n and i, the relevant group is not present if an index is equal to zero. For example, the group E is not present for i=0, so that the two aromatic six-membered rings are not connected via a single bond to form a fluorene ring system.

For the purposes of this application, an arylamino group as group A is taken to mean a group in which at least one aryl group or heteroaryl group is bonded to a trivalent nitrogen atom. The way in which the group is constructed further, or what further groups it includes, is unimportant for the definition.

The group A is preferably an arylamino group, optionally substituted by one or more radicals $R^1$.

An arylamino group as group A preferably includes a group of the following formula (A-1), where Ar* represents any desired substituted or unsubstituted aryl or heteroaryl group, and the dashed lines represent bonds to any desired substituents.

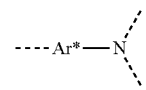

formula (A-1)

Regarding the bonding of the arylamino group A to the remainder of the compound, this group may be bonded directly via the nitrogen atom or via any desired substituent or via the aryl or heteroaryl group which is bonded to the nitrogen atom.

The said nitrogen atom of the arylamino group as group A is an amino nitrogen atom. Apart from the said aryl or heteroaryl group, any desired further substituents, such as, for example, alkyl or alkenyl groups, may be bonded to the nitrogen atom. Preferably, however, exclusively aryl or heteroaryl groups are bonded. The groups bonded to the nitrogen atom may be constituents of a ring, such as, for example, in the case of a dihydroacridine group. However, this is preferably not the case.

An arylamino group in the sense of this application can be a monoarylamino group, a diarylamino group or a triarylamino group, depending on the number of aryl or heteroaryl groups which are bonded to the nitrogen atom (1, 2 or 3). Preference is given to di- or triarylamino groups.

The arylamino group as group A preferably contains only a single unit of the above formula (A-1). It particularly preferably contains only a single amino group. It very particularly preferably contains only a single nitrogen atom.

For the purposes of this application, a carbazole group as group A is taken to mean any desired group containing a carbazole group. A carbazole group in the sense of the present application is also taken to mean carbazole groups in which one or more carbon atoms of the aromatic six-membered rings have been replaced by nitrogen. Furthermore, it is also taken to mean carbazole groups in which the five-membered carbazole ring has been expanded to form a six-membered ring, so that, for example, a methylene, silylene, oxygen or sulfur bridge is arranged opposite the nitrogen atom. In the former case, this gives rise, for example, to a unit which is also called dihydroacridine. Furthermore, a carbazole groups is also taken to mean carbazole groups containing condensed-on groups, such as, for example, indenocarbazoles or indolocarbazoles.

Regarding the radicals $R^1$ to $R^3$, the following generally preferred definitions apply:

$R^1$ is preferably on each occurrence, identically or differently, H, D, F, CN, $Si(R^3)_3$, a straight-chain alkyl or alkoxy group having 1 to 20 C atoms or a branched or cyclic alkyl or alkoxy group having 3 to 20 C atoms, where the above-mentioned groups may each be substituted by one or more radicals $R^3$ and where one or more $CH_2$ groups in the above-mentioned groups may be replaced by —C≡C—, —$R^3$C=C$R^3$—, $Si(R^3)_2$, C=O, C=NR, —O—, —S—, —C(=O)O— or —C(=O)N$R^3$—, or an aromatic or heteroaromatic ring system having 5 to 20 aromatic ring atoms, which may in each case be substituted by one or more radicals $R^3$, where two or more radicals $R^1$ may be linked to one another and may form a ring.

$R^2$ is preferably on each occurrence, identically or differently, H, D, F, CN, $Si(R^3)_3$, a straight-chain alkyl or alkoxy group having 1 to 20 C atoms or a branched or cyclic alkyl or alkoxy group having 3 to 20 C atoms, where the above-mentioned groups may each be substituted by one or more radicals $R^3$ and where one or more $CH_2$ groups in the above-mentioned groups may be replaced by —C≡C—, —$R^3$C=C$R^3$—, $Si(R^3)_2$, C=O, C=N$R^3$, —N$R^3$—, —O—, —S—, —C(=O)O— or —C(=O)N$R^3$—, or an aromatic or heteroaromatic ring system having 5 to 20 aromatic ring atoms, which may in each case be substituted by one or more radicals $R^3$, where two or more radicals $R^2$ may be linked to one another and may form a ring.

$R^3$ is preferably on each occurrence, identically or differently, H, D, F, CN, $Si(R^4)_3$, a straight-chain alkyl or alkoxy group having 1 to 20 C atoms or a branched or cyclic alkyl or alkoxy group having 3 to 20 C atoms, where the above-mentioned groups may each be substituted by one or more radicals $R^4$ and where one or more $CH_2$ groups in the above-mentioned groups may be replaced by —C≡C—, —$R^4$C=C$R^4$—, $Si(R^4)_2$, C=O, C=N$R^4$, —N$R^4$—, —O—, —S—, —C(=O)O— or —C(=O)N$R^4$—, or an aromatic or heteroaromatic ring system having 5 to 20 aromatic ring atoms, which may in each case be substituted by one or more radicals $R^4$, where two or more radicals $R^3$ may be linked to one another and may form a ring.

In formula (I), X is preferably equal to O. This preferred embodiment should preferably be combined with all preferred embodiments of the groups and indices in formula (I), in particular with the preferred embodiments of A and the radicals $R^1$ to $R^3$.

It is preferred for not more than three groups Z in an aromatic ring to be equal to N. It is furthermore preferred for not more than two adjacent groups Z in an aromatic ring to be equal to N. It is furthermore preferred for not more than one group Z per aromatic ring to be equal to N.

It is generally preferred for Z to be equal to $CR^1$, where, in the case where a group A is bonded to Z, the group Z is equal to C.

The compound of the formula (I) preferably contains no condensed aryl group having more than 14 aromatic ring atoms, particularly preferably no condensed aryl group having more than 10 aromatic ring atoms.

The group A is preferably a group of the following formula (A-II)

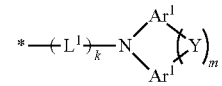

formula (A-II), where:

$L^1$ is on each occurrence, identically or differently, C=O, $Si(R^1)_2$, $PR^1$, P(=O)($R^1$), O, S, SO, $SO_2$, an alkylene group having 1 to 20 C atoms or an alkenylene or alkynylene group having 2 to 20 C atoms, where one or more $CH_2$ groups in the said groups may be replaced by C=O, C=N$R^1$, C=O—O, C=O—N$R^1$, $Si(R^1)_2$, N$R^1$, P(=O)($R^1$), O, S, SO or $SO_2$ and where one or more H atoms in the above-mentioned groups may be replaced by D, F or CN, or an aromatic or heteroaromatic ring system having 6 to 24 aromatic ring atoms, which may be substituted by one or more radicals $R^1$;

$Ar^1$ is on each occurrence, identically or differently, an aromatic or heteroaromatic ring system having 6 to 30 aromatic ring atoms, which may be substituted by one or more radicals $R^1$;

Y is selected from a single bond, $BR^1$, $C(R^1)_2$, $C(R^1)_2$—C($R^1$)_2, $Si(R^1)_2$, $Si(R^1)_2$—$Si(R^1)_2$, C=O, C=N$R^1$, C=C($R^1$)_2, C(=O)N($R^1$), O, S, S=O, $SO_2$ and N$R^1$;

k is equal to 0, 1, 2 or 3;

m is equal to 0 or 1;

where the group A is bonded to the remainder of the compound of the formula (I) via the bond labelled with *.

$L^1$ in formula (A-II) is preferably on each occurrence, identically or differently, $Si(R^1)_2$, O, S, an alkylene group having 1 to 10 C atoms or an alkenylene or alkynylene group having 2 to 10 C atoms, where one or more $CH_2$ groups in the said groups may be replaced by $Si(R^1)_2$, O or S and where one or more H atoms in the said groups may be replaced by D, F or CN, or an aromatic ring system having 6 to 24 aromatic ring atoms, which may be substituted by one or more radicals $R^1$.

$L^1$ is particularly preferably on each occurrence, identically or differently, an aromatic or heteroaromatic ring system having 6 to 18 aromatic ring atoms, which may be substituted by one or more radicals $R^1$. $L^1$ is very particularly preferably on each occurrence, identically or differently, phenyl, biphenyl, naphthyl, terphenyl, fluorenyl, spirobifluorene, indenofluorenyl, carbazole, dibenzofuran or dibenzothiophene, each of which may be substituted by one or more radicals R¹.

k in formula (A-II) is furthermore preferably equal to 0 or 1, particularly preferably equal to 0.

m in formula (A-II) is furthermore preferably equal to 0, i.e. the two groups Ar¹ are not connected to one another.

Ar¹ in formula (A-II) is furthermore preferably on each occurrence, identically or differently, an aromatic or heteroaromatic ring system having 6 to 24 aromatic ring atoms, which may be substituted by one or more radicals R¹. Of these, very particular preference is given to phenyl, biphenyl, naphthyl, terphenyl, fluorenyl, spirobifluorene, indenofluorenyl, carbazole, dibenzofuran and dibenzothiophene, each of which may be substituted by one or more radicals R¹.

The group Y in formula (A-II) is furthermore preferably selected from a single bond, C(R¹)₂, O, S and NR¹. Y is particularly preferably a single bond.

Particularly preferred groups A conform to the formulae (A-II-1) to (A-II-50):

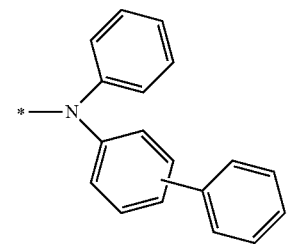

formula (A-II-1)

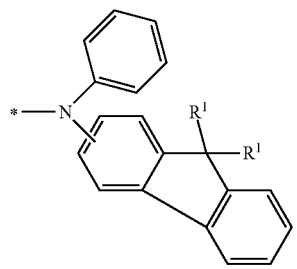

formula (A-II-2)

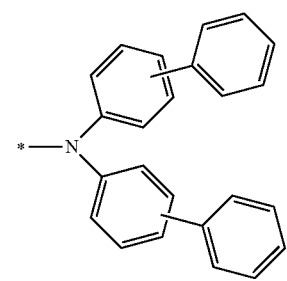

formula (A-II-3)

formula (A-II-4)

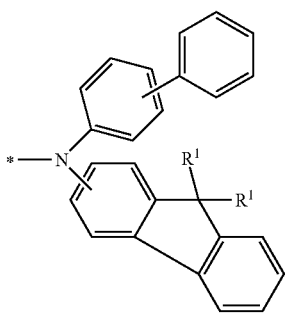

formula (A-II-5)

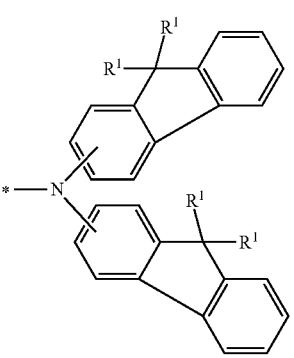

formula (A-II-6)

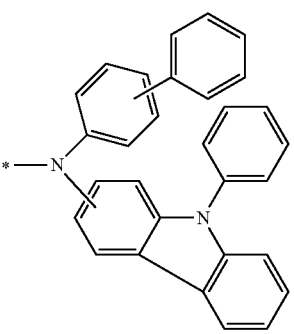

formula (A-II-7)

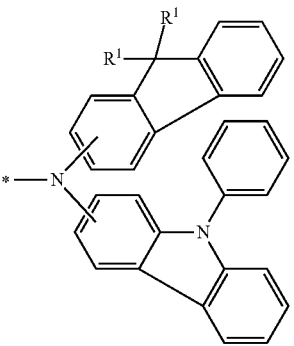

formula (A-II-8)

formula (A-II-9)
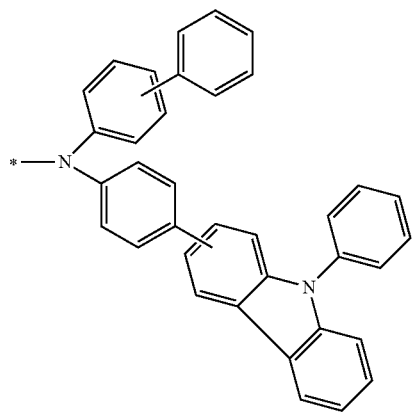
formula (A-II-10)
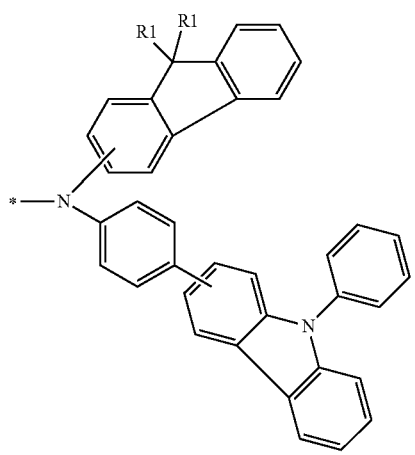
formula (A-II-11)
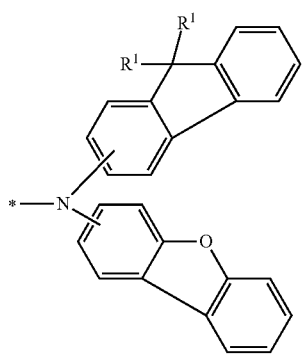
formula (A-II-12)
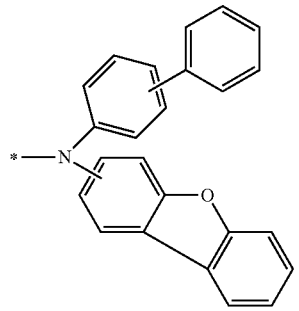
formula (A-II-13)
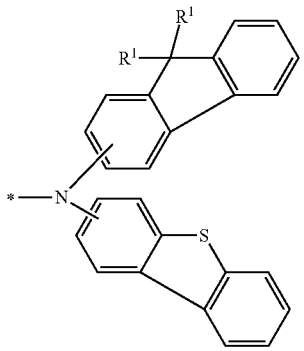
formula (A-II-14)
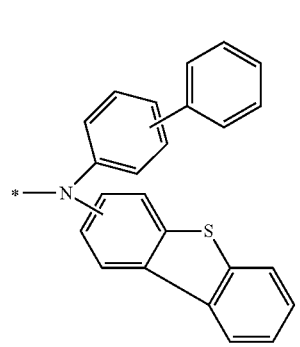
formula (A-II-15)
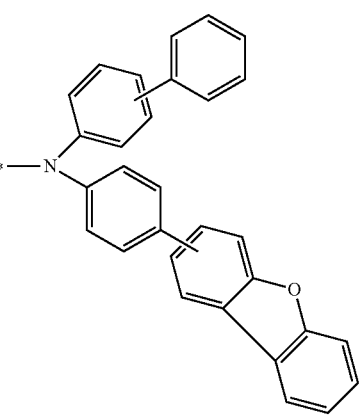
formula (A-II-16)
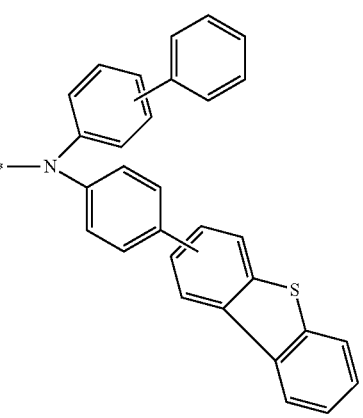

formula (A-II-17)
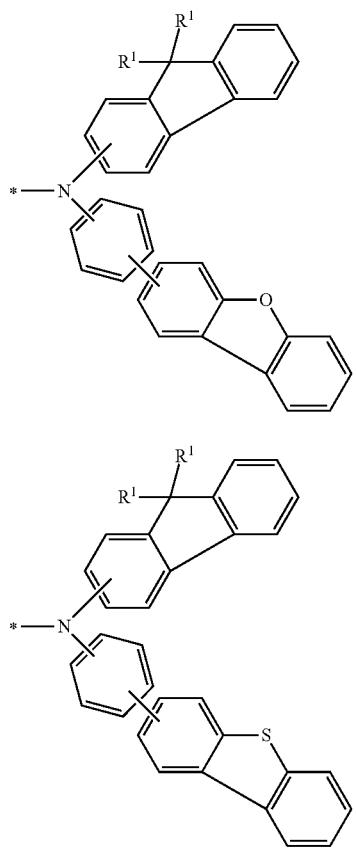
formula (A-II-18)
formula (A-II-19)
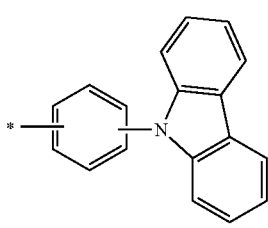
formula (A-II-20)
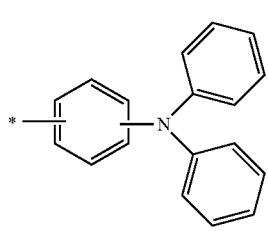
formula (A-II-21)
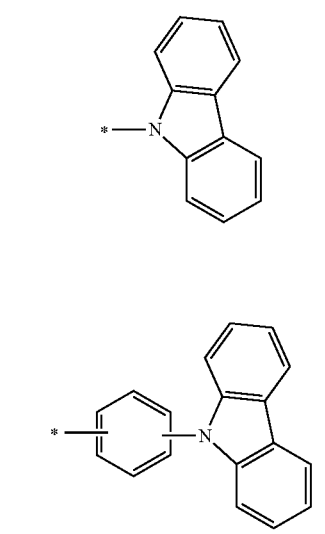
formula (A-II-22)
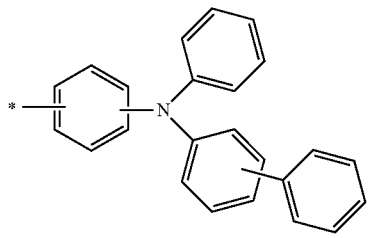
formula (A-II-23)
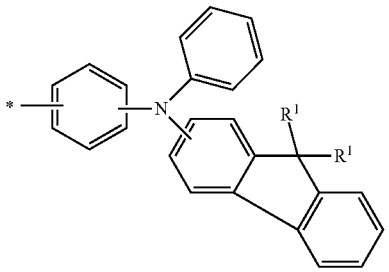
formula (A-II-24)
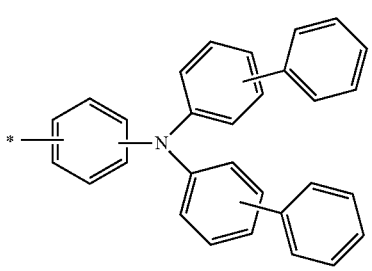
formula (A-II-25)
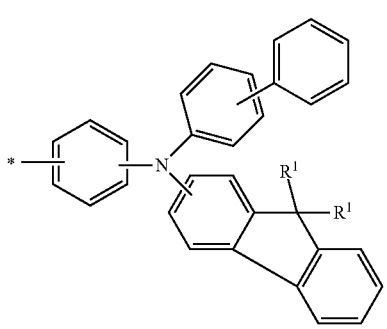
formula (A-II-26)
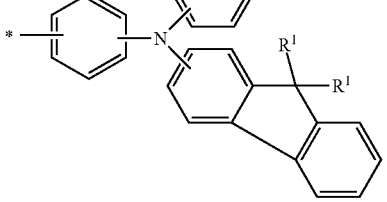

formula (A-II-27)
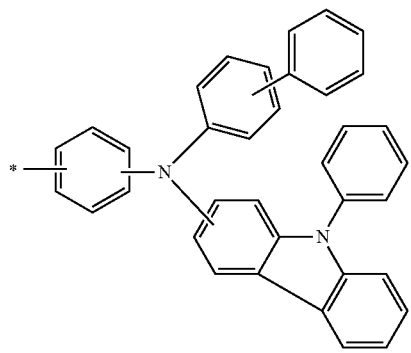
formula (A-II-28)
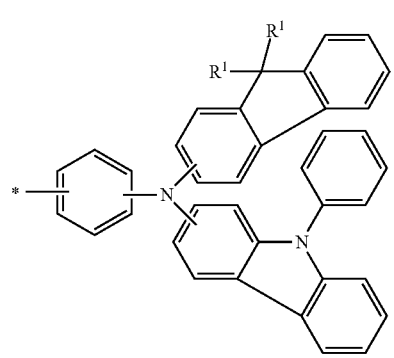
formula (A-II-29)
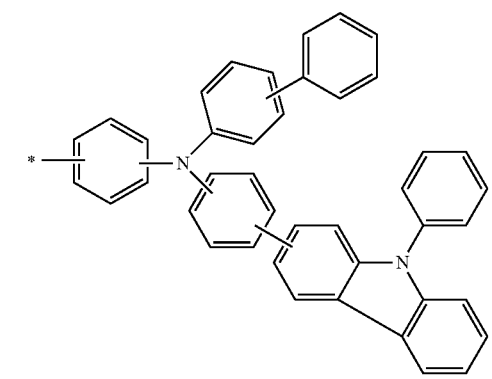
formula (A-II-30)
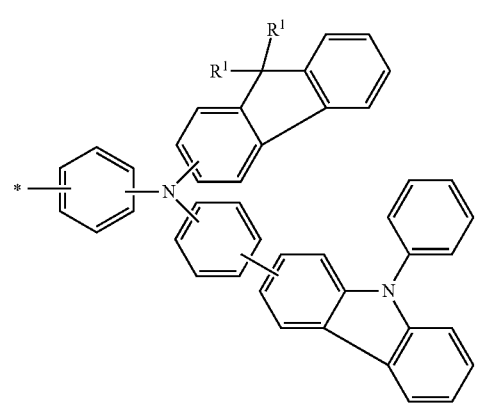
formula (A-II-31)
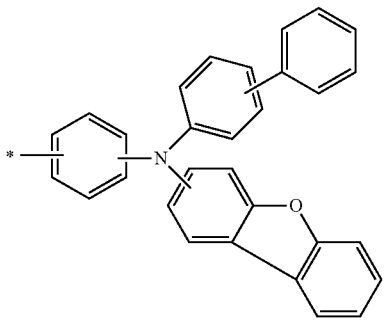
formula (A-II-32)
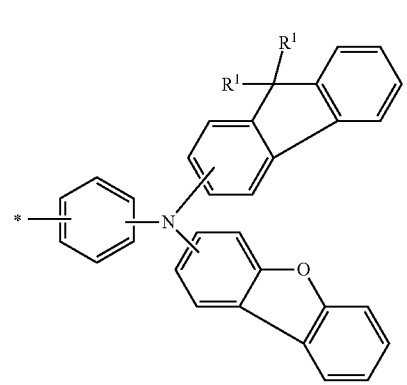
formula (A-II-33)
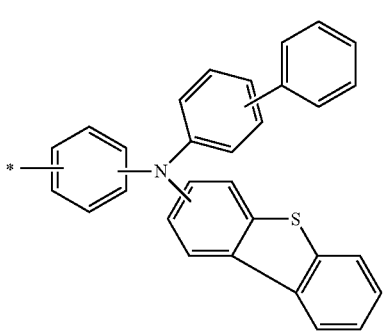
formula (A-II-34)
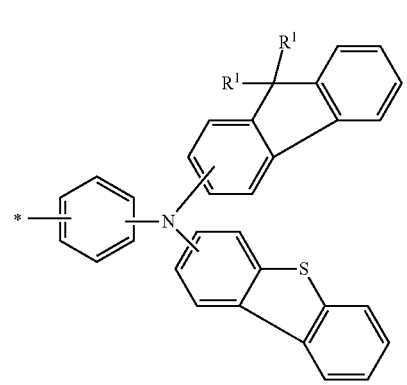

formula (A-II-35)
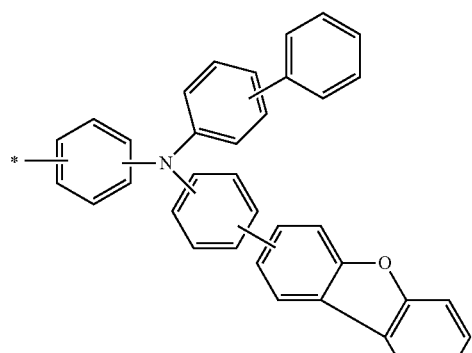
formula (A-II-36)
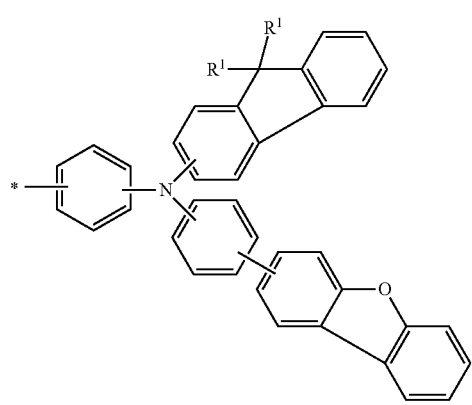
formula (A-II-37)
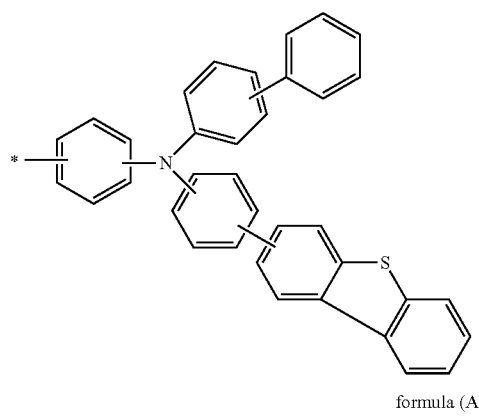
formula (A-II-38)
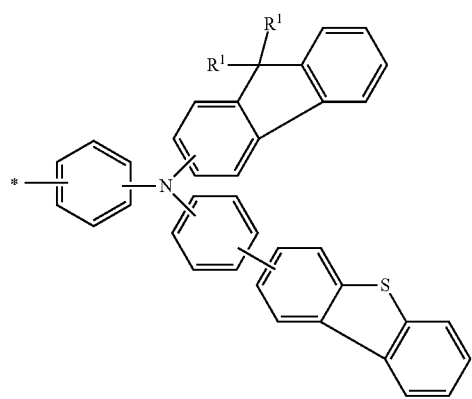
formula (A-II-39)
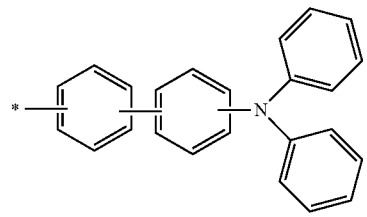
formula (A-II-40)
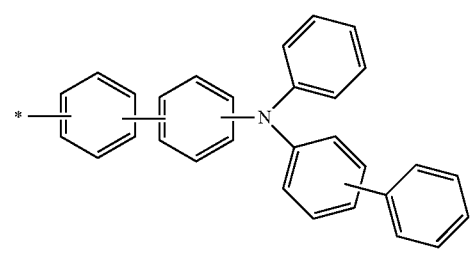
formula (A-II-41)
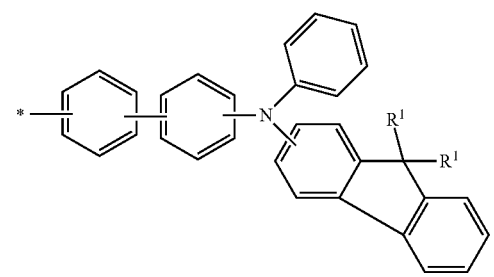
formula (A-II-42)
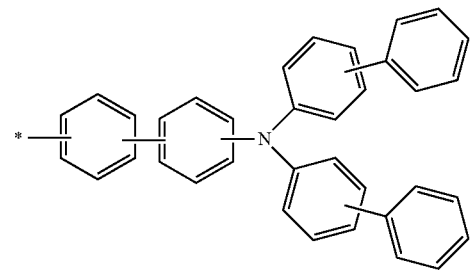
formula (A-II-43)

formula (A-II-44)
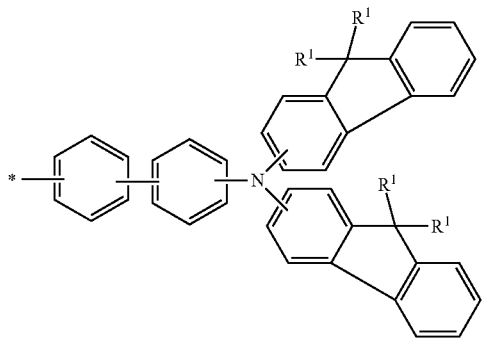

formula (A-II-45)
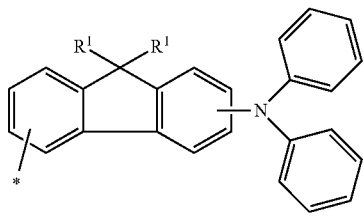

formula (A-II-46)
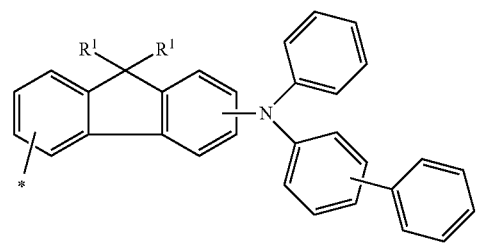

formula (A-II-47)
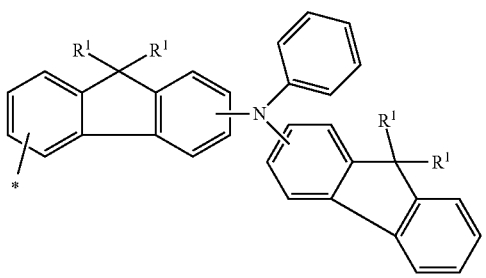

formula (A-II-48)
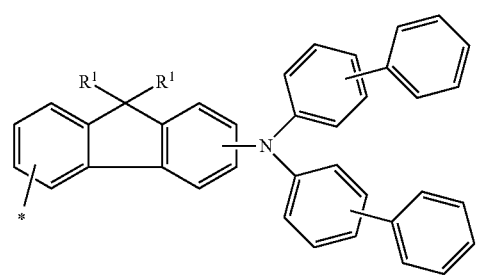

formula (A-II-49)
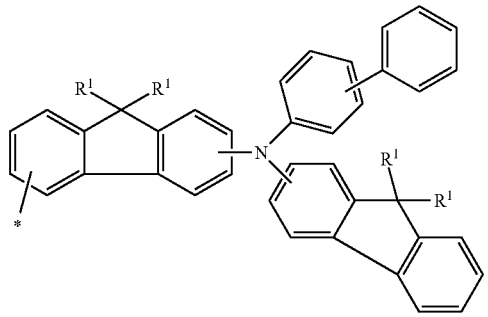

formula (A-II-50)
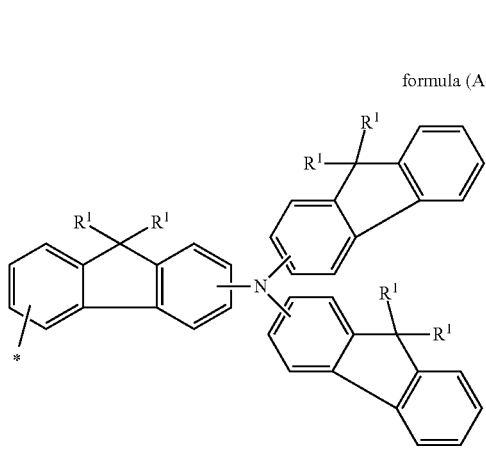

where the groups may be substituted by one or more radicals $R^1$, as defined above, at all free positions. It is preferred for radicals $R^1$ to be defined here in accordance with their preferred embodiments.

The possible bonding positions of the groups A in the following formula (I-num) are indicated by numbers.

formula (I-num)
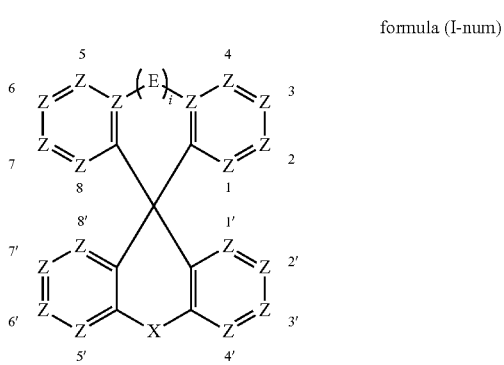

In accordance with the above numbering, it is preferred for the group A to be bonded in position 2, 4, 2', 4', 5, 7, 5' or 7'. The group A is particularly preferably bonded in position 2, 2', 7 or 7'. i here can be equal to 0 or 1. Furthermore, X here is preferably equal to O.

Preferred embodiments of the compounds of the formula (I) thus conform to one of the formulae (I-1) to (I-8):

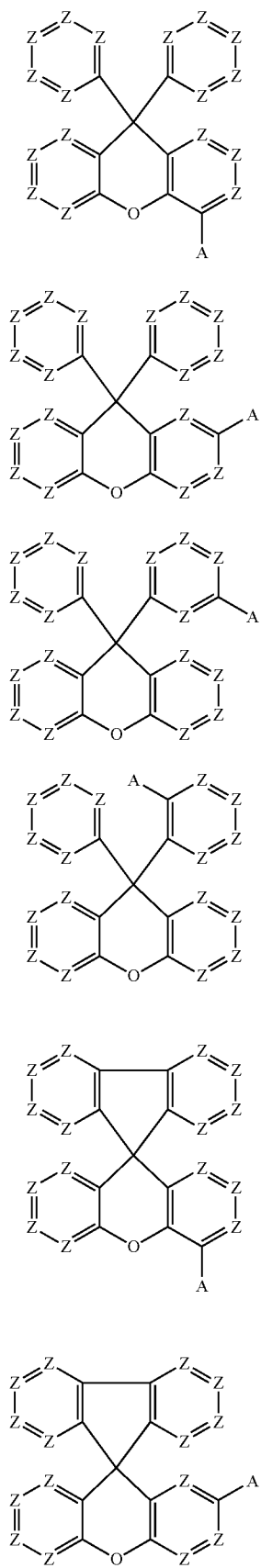

formula (I-1)
formula (I-2)
formula (I-3)
formula (I-4)
formula (I-5)
formula (I-6)

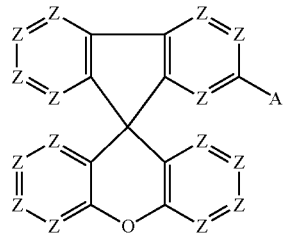

formula (I-7)

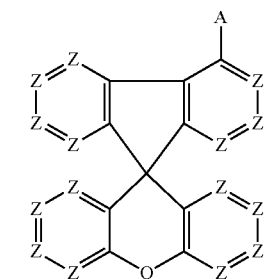

formula (I-8)

where the symbols occurring are as defined above.

The preferred embodiments of the variable groups indicated above apply to the compounds of the formulae (I-1) to (I-8). It is particularly preferred for these compounds for Z to be equal to $CR^1$. It is furthermore particularly preferred for these compounds for A to conform to formula (A-II), as defined above.

Particularly preferred embodiments of compounds of the formula (I) are the structures of the formulae (I-1-1) to (I-8-50) indicated in the following table.

They are composed of a basic structure selected from basic structures of the formulae (I-1) to (I-8) and from groups A selected from the preferred embodiments of the formulae (A-II-1) to (A-II-50).

| | Basic structure | Group A |
|---|---|---|
| (I-1-1) | (I-1) | (A-II-1) |
| (I-1-2) | " | (A-II-2) |
| (I-1-3) | " | (A-II-3) |
| (I-1-4) | " | (A-II-4) |
| (I-1-5) | " | (A-II-5) |
| (I-1-6) | " | (A-II-6) |
| (I-1-7) | " | (A-II-7) |
| (I-1-8) | " | (A-II-8) |
| (I-1-9) | " | (A-II-9) |
| (I-1-10) | " | (A-II-10) |
| (I-1-11) | " | (A-II-11) |
| (I-1-12) | " | (A-II-12) |
| (I-1-13) | " | (A-II-13) |
| (I-1-14) | " | (A-II-14) |
| (I-1-15) | " | (A-II-15) |
| (I-1-16) | " | (A-II-16) |
| (I-1-17) | " | (A-II-17) |
| (I-1-18) | " | (A-II-18) |
| (I-1-19) | " | (A-II-19) |
| (I-1-20) | " | (A-II-20) |
| (I-1-21) | " | (A-II-21) |
| (I-1-22) | " | (A-II-22) |
| (I-1-23) | " | (A-II-23) |
| (I-1-24) | " | (A-II-24) |
| (I-1-25) | " | (A-II-25) |
| (I-1-26) | " | (A-II-26) |
| (I-1-27) | " | (A-II-27) |
| (I-1-28) | " | (A-II-28) |
| (I-1-29) | " | (A-II-29) |
| (I-1-30) | " | (A-II-30) |
| (I-1-31) | " | (A-II-31) |

| | Basic structure | Group A |
|---|---|---|
| (I-1-32) | " | (A-II-32) |
| (I-1-33) | " | (A-II-33) |
| (I-1-34) | " | (A-II-34) |
| (I-1-35) | " | (A-II-35) |
| (I-1-36) | " | (A-II-36) |
| (I-1-37) | " | (A-II-37) |
| (I-1-38) | " | (A-II-38) |
| (I-1-39) | " | (A-II-39) |
| (I-1-40) | " | (A-II-40) |
| (I-1-41) | " | (A-II-41) |
| (I-1-42) | " | (A-II-42) |
| (I-1-43) | " | (A-II-43) |
| (I-1-44) | " | (A-II-44) |
| (I-1-45) | " | (A-II-45) |
| (I-1-46) | " | (A-II-46) |
| (I-1-47) | " | (A-II-47) |
| (I-1-48) | " | (A-II-48) |
| (I-1-49) | " | (A-II-49) |
| (I-1-50) | " | (A-II-50) |
| (I-2-1) | (I-2) | (A-II-1) |
| (I-2-2) | " | (A-II-2) |
| (I-2-3) | " | (A-II-3) |
| (I-2-4) | " | (A-II-4) |
| (I-2-5) | " | (A-II-5) |
| (I-2-6) | " | (A-II-6) |
| (I-2-7) | " | (A-II-7) |
| (I-2-8) | " | (A-II-8) |
| (I-2-9) | " | (A-II-9) |
| (I-2-10) | " | (A-II-10) |
| (I-2-11) | " | (A-II-11) |
| (I-2-12) | " | (A-II-12) |
| (I-2-13) | " | (A-II-13) |
| (I-2-14) | " | (A-II-14) |
| (I-2-15) | " | (A-II-15) |
| (I-2-16) | " | (A-II-16) |
| (I-2-17) | " | (A-II-17) |
| (I-2-18) | " | (A-II-18) |
| (I-2-19) | " | (A-II-19) |
| (I-2-20) | " | (A-II-20) |
| (I-2-21) | " | (A-II-21) |
| (I-2-22) | " | (A-II-22) |
| (I-2-23) | " | (A-II-23) |
| (I-2-24) | " | (A-II-24) |
| (I-2-25) | " | (A-II-25) |
| (I-2-26) | " | (A-II-26) |
| (I-2-27) | " | (A-II-27) |
| (I-2-28) | " | (A-II-28) |
| (I-2-29) | " | (A-II-29) |
| (I-2-30) | " | (A-II-30) |
| (I-2-31) | " | (A-II-31) |
| (I-2-32) | " | (A-II-32) |
| (I-2-33) | " | (A-II-33) |
| (I-2-34) | " | (A-II-34) |
| (I-2-35) | " | (A-II-35) |
| (I-2-36) | " | (A-II-36) |
| (I-2-37) | " | (A-II-37) |
| (I-2-38) | " | (A-II-38) |
| (I-2-39) | " | (A-II-39) |
| (I-2-40) | " | (A-II-40) |
| (I-2-41) | " | (A-II-41) |
| (I-2-42) | " | (A-II-42) |
| (I-2-43) | " | (A-II-43) |
| (I-2-44) | " | (A-II-44) |
| (I-2-45) | " | (A-II-45) |
| (I-2-46) | " | (A-II-46) |
| (I-2-47) | " | (A-II-47) |
| (I-2-48) | " | (A-II-48) |
| (I-2-49) | " | (A-II-49) |
| (I-2-50) | " | (A-II-50) |
| (I-3-1) | (I-3) | (A-II-1) |
| (I-3-2) | " | (A-II-2) |
| (I-3-3) | " | (A-II-3) |
| (I-3-4) | " | (A-II-4) |
| (I-3-5) | " | (A-II-5) |
| (I-3-6) | " | (A-II-6) |
| (I-3-7) | " | (A-II-7) |
| (I-3-8) | " | (A-II-8) |
| (I-3-9) | " | (A-II-9) |
| (I-3-10) | " | (A-II-10) |
| (I-3-11) | " | (A-II-11) |
| (I-3-12) | " | (A-II-12) |
| (I-3-13) | " | (A-II-13) |
| (I-3-14) | " | (A-II-14) |
| (I-3-15) | " | (A-II-15) |
| (I-3-16) | " | (A-II-16) |
| (I-3-17) | " | (A-II-17) |
| (I-3-18) | " | (A-II-18) |
| (I-3-19) | " | (A-II-19) |
| (I-3-20) | " | (A-II-20) |
| (I-3-21) | " | (A-II-21) |
| (I-3-22) | " | (A-II-22) |
| (I-3-23) | " | (A-II-23) |
| (I-3-24) | " | (A-II-24) |
| (I-3-25) | " | (A-II-25) |
| (I-3-26) | " | (A-II-26) |
| (I-3-27) | " | (A-II-27) |
| (I-3-28) | " | (A-II-28) |
| (I-3-29) | " | (A-II-29) |
| (I-3-30) | " | (A-II-30) |
| (I-3-31) | " | (A-II-31) |
| (I-3-32) | " | (A-II-32) |
| (I-3-33) | " | (A-II-33) |
| (I-3-34) | " | (A-II-34) |
| (I-3-35) | " | (A-II-35) |
| (I-3-36) | " | (A-II-36) |
| (I-3-37) | " | (A-II-37) |
| (I-3-38) | " | (A-II-38) |
| (I-3-39) | " | (A-II-39) |
| (I-3-40) | " | (A-II-40) |
| (I-3-41) | " | (A-II-41) |
| (I-3-42) | " | (A-II-42) |
| (I-3-43) | " | (A-II-43) |
| (I-3-44) | " | (A-II-44) |
| (I-3-45) | " | (A-II-45) |
| (I-3-46) | " | (A-II-46) |
| (I-3-47) | " | (A-II-47) |
| (I-3-48) | " | (A-II-48) |
| (I-3-49) | " | (A-II-49) |
| (I-3-50) | " | (A-II-50) |
| (I-4-1) | (I-4) | (A-II-1) |
| (I-4-2) | " | (A-II-2) |
| (I-4-3) | " | (A-II-3) |
| (I-4-4) | " | (A-II-4) |
| (I-4-5) | " | (A-II-5) |
| (I-4-6) | " | (A-II-6) |
| (I-4-7) | " | (A-II-7) |
| (I-4-8) | " | (A-II-8) |
| (I-4-9) | " | (A-II-9) |
| (I-4-10) | " | (A-II-10) |
| (I-4-11) | " | (A-II-11) |
| (I-4-12) | " | (A-II-12) |
| (I-4-13) | " | (A-II-13) |
| (I-4-14) | " | (A-II-14) |
| (I-4-15) | " | (A-II-15) |
| (I-4-16) | " | (A-II-16) |
| (I-4-17) | " | (A-II-17) |
| (I-4-18) | " | (A-II-18) |
| (I-4-19) | " | (A-II-19) |
| (I-4-20) | " | (A-II-20) |
| (I-4-21) | " | (A-II-21) |
| (I-4-22) | " | (A-II-22) |
| (I-4-23) | " | (A-II-23) |
| (I-4-24) | " | (A-II-24) |
| (I-4-25) | " | (A-II-25) |
| (I-4-26) | " | (A-II-26) |
| (I-4-27) | " | (A-II-27) |
| (I-4-28) | " | (A-II-28) |
| (I-4-29) | " | (A-II-29) |
| (I-4-30) | " | (A-II-30) |
| (I-4-31) | " | (A-II-31) |
| (I-4-32) | " | (A-II-32) |
| (I-4-33) | " | (A-II-33) |
| (I-4-34) | " | (A-II-34) |
| (I-4-35) | " | (A-II-35) |

-continued

|  | Basic structure | Group A |
|---|---|---|
| (I-4-36) | " | (A-II-36) |
| (I-4-37) | " | (A-II-37) |
| (I-4-38) | " | (A-II-38) |
| (I-4-39) | " | (A-II-39) |
| (I-4-40) | " | (A-II-40) |
| (I-4-41) | " | (A-II-41) |
| (I-4-42) | " | (A-II-42) |
| (I-4-43) | " | (A-II-43) |
| (I-4-44) | " | (A-II-44) |
| (I-4-45) | " | (A-II-45) |
| (I-4-46) | " | (A-II-46) |
| (I-4-47) | " | (A-II-47) |
| (I-4-48) | " | (A-II-48) |
| (I-4-49) | " | (A-II-49) |
| (I-4-50) | " | (A-II-50) |
| (I-5-1) | (I-5) | (A-II-1) |
| (I-5-2) | " | (A-II-2) |
| (I-5-3) | " | (A-II-3) |
| (I-5-4) | " | (A-II-4) |
| (I-5-5) | " | (A-II-5) |
| (I-5-6) | " | (A-II-6) |
| (I-5-7) | " | (A-II-7) |
| (I-5-8) | " | (A-II-8) |
| (I-5-9) | " | (A-II-9) |
| (I-5-10) | " | (A-II-10) |
| (I-5-11) | " | (A-II-11) |
| (I-5-12) | " | (A-II-12) |
| (I-5-13) | " | (A-II-13) |
| (I-5-14) | " | (A-II-14) |
| (I-5-15) | " | (A-II-15) |
| (I-5-16) | " | (A-II-16) |
| (I-5-17) | " | (A-II-17) |
| (I-5-18) | " | (A-II-18) |
| (I-5-19) | " | (A-II-19) |
| (I-5-20) | " | (A-II-20) |
| (I-5-21) | " | (A-II-21) |
| (I-5-22) | " | (A-II-22) |
| (I-5-23) | " | (A-II-23) |
| (I-5-24) | " | (A-II-24) |
| (I-5-25) | " | (A-II-25) |
| (I-5-26) | " | (A-II-26) |
| (I-5-27) | " | (A-II-27) |
| (I-5-28) | " | (A-II-28) |
| (I-5-29) | " | (A-II-29) |
| (I-5-30) | " | (A-II-30) |
| (I-5-31) | " | (A-II-31) |
| (I-5-32) | " | (A-II-32) |
| (I-5-33) | " | (A-II-33) |
| (I-5-34) | " | (A-II-34) |
| (I-5-35) | " | (A-II-35) |
| (I-5-36) | " | (A-II-36) |
| (I-5-37) | " | (A-II-37) |
| (I-5-38) | " | (A-II-38) |
| (I-5-39) | " | (A-II-39) |
| (I-5-40) | " | (A-II-40) |
| (I-5-41) | " | (A-II-41) |
| (I-5-42) | " | (A-II-42) |
| (I-5-43) | " | (A-II-43) |
| (I-5-44) | " | (A-II-44) |
| (I-5-45) | " | (A-II-45) |
| (I-5-46) | " | (A-II-46) |
| (I-5-47) | " | (A-II-47) |
| (I-5-48) | " | (A-II-48) |
| (I-5-49) | " | (A-II-49) |
| (I-5-50) | " | (A-II-50) |
| (I-6-1) | (I-6) | (A-II-1) |
| (I-6-2) | " | (A-II-2) |
| (I-6-3) | " | (A-II-3) |
| (I-6-4) | " | (A-II-4) |
| (I-6-5) | " | (A-II-5) |
| (I-6-6) | " | (A-II-6) |
| (I-6-7) | " | (A-II-7) |
| (I-6-8) | " | (A-II-8) |
| (I-6-9) | " | (A-II-9) |
| (I-6-10) | " | (A-II-10) |
| (I-6-11) | " | (A-II-11) |
| (I-6-12) | " | (A-II-12) |
| (I-6-13) | " | (A-II-13) |
| (I-6-14) | " | (A-II-14) |
| (I-6-15) | " | (A-II-15) |
| (I-6-16) | " | (A-II-16) |
| (I-6-17) | " | (A-II-17) |
| (I-6-18) | " | (A-II-18) |
| (I-6-19) | " | (A-II-19) |
| (I-6-20) | " | (A-II-20) |
| (I-6-21) | " | (A-II-21) |
| (I-6-22) | " | (A-II-22) |
| (I-6-23) | " | (A-II-23) |
| (I-6-24) | " | (A-II-24) |
| (I-6-25) | " | (A-II-25) |
| (I-6-26) | " | (A-II-26) |
| (I-6-27) | " | (A-II-27) |
| (I-6-28) | " | (A-II-28) |
| (I-6-29) | " | (A-II-29) |
| (I-6-30) | " | (A-II-30) |
| (I-6-31) | " | (A-II-31) |
| (I-6-32) | " | (A-II-32) |
| (I-6-33) | " | (A-II-33) |
| (I-6-34) | " | (A-II-34) |
| (I-6-35) | " | (A-II-35) |
| (I-6-36) | " | (A-II-36) |
| (I-6-37) | " | (A-II-37) |
| (I-6-38) | " | (A-II-38) |
| (I-6-39) | " | (A-II-39) |
| (I-6-40) | " | (A-II-40) |
| (I-6-41) | " | (A-II-41) |
| (I-6-42) | " | (A-II-42) |
| (I-6-43) | " | (A-II-43) |
| (I-6-44) | " | (A-II-44) |
| (I-6-45) | " | (A-II-45) |
| (I-6-46) | " | (A-II-46) |
| (I-6-47) | " | (A-II-47) |
| (I-6-48) | " | (A-II-48) |
| (I-6-49) | " | (A-II-49) |
| (I-6-50) | " | (A-II-50) |
| (I-7-1) | (I-7) | (A-II-1) |
| (I-7-2) | " | (A-II-2) |
| (I-7-3) | " | (A-II-3) |
| (I-7-4) | " | (A-II-4) |
| (I-7-5) | " | (A-II-5) |
| (I-7-6) | " | (A-II-6) |
| (I-7-7) | " | (A-II-7) |
| (I-7-8) | " | (A-II-8) |
| (I-7-9) | " | (A-II-9) |
| (I-7-10) | " | (A-II-10) |
| (I-7-11) | " | (A-II-11) |
| (I-7-12) | " | (A-II-12) |
| (I-7-13) | " | (A-II-13) |
| (I-7-14) | " | (A-II-14) |
| (I-7-15) | " | (A-II-15) |
| (I-7-16) | " | (A-II-16) |
| (I-7-17) | " | (A-II-17) |
| (I-7-18) | " | (A-II-18) |
| (I-7-19) | " | (A-II-19) |
| (I-7-20) | " | (A-II-20) |
| (I-7-21) | " | (A-II-21) |
| (I-7-22) | " | (A-II-22) |
| (I-7-23) | " | (A-II-23) |
| (I-7-24) | " | (A-II-24) |
| (I-7-25) | " | (A-II-25) |
| (I-7-26) | " | (A-II-26) |
| (I-7-27) | " | (A-II-27) |
| (I-7-28) | " | (A-II-28) |
| (I-7-29) | " | (A-II-29) |
| (I-7-30) | " | (A-II-30) |
| (I-7-31) | " | (A-II-31) |
| (I-7-32) | " | (A-II-32) |
| (I-7-33) | " | (A-II-33) |
| (I-7-34) | " | (A-II-34) |
| (I-7-35) | " | (A-II-35) |
| (I-7-36) | " | (A-II-36) |
| (I-7-37) | " | (A-II-37) |
| (I-7-38) | " | (A-II-38) |
| (I-7-39) | " | (A-II-39) |

| | Basic structure | Group A |
|---|---|---|
| (I-7-40) | " | (A-II-40) |
| (I-7-41) | " | (A-II-41) |
| (I-7-42) | " | (A-II-42) |
| (I-7-43) | " | (A-II-43) |
| (I-7-44) | " | (A-II-44) |
| (I-7-45) | " | (A-II-45) |
| (I-7-46) | " | (A-II-46) |
| (I-7-47) | " | (A-II-47) |
| (I-7-48) | " | (A-II-48) |
| (I-7-49) | " | (A-II-49) |
| (I-7-50) | " | (A-II-50) |
| (I-8-1) | (I-8) | (A-II-1) |
| (I-8-2) | " | (A-II-2) |
| (I-8-3) | " | (A-II-3) |
| (I-8-4) | " | (A-II-4) |
| (I-8-5) | " | (A-II-5) |
| (I-8-6) | " | (A-II-6) |
| (I-8-7) | " | (A-II-7) |
| (I-8-8) | " | (A-II-8) |
| (I-8-9) | " | (A-II-9) |
| (I-8-10) | " | (A-II-10) |
| (I-8-11) | " | (A-II-11) |
| (I-8-12) | " | (A-II-12) |
| (I-8-13) | " | (A-II-13) |
| (I-8-14) | " | (A-II-14) |
| (I-8-15) | " | (A-II-15) |
| (I-8-16) | " | (A-II-16) |
| (I-8-17) | " | (A-II-17) |
| (I-8-18) | " | (A-II-18) |
| (I-8-19) | " | (A-II-19) |
| (I-8-20) | " | (A-II-20) |
| (I-8-21) | " | (A-II-21) |
| (I-8-22) | " | (A-II-22) |
| (I-8-23) | " | (A-II-23) |
| (I-8-24) | " | (A-II-24) |
| (I-8-25) | " | (A-II-25) |
| (I-8-26) | " | (A-II-26) |
| (I-8-27) | " | (A-II-27) |
| (I-8-28) | " | (A-II-28) |
| (I-8-29) | " | (A-II-29) |
| (I-8-30) | " | (A-II-30) |
| (I-8-31) | " | (A-II-31) |
| (I-8-32) | " | (A-II-32) |
| (I-8-33) | " | (A-II-33) |
| (I-8-34) | " | (A-II-34) |
| (I-8-35) | " | (A-II-35) |
| (I-8-36) | " | (A-II-36) |
| (I-8-37) | " | (A-II-37) |
| (I-8-38) | " | (A-II-38) |
| (I-8-39) | " | (A-II-39) |
| (I-8-40) | " | (A-II-40) |
| (I-8-41) | " | (A-II-41) |
| (I-8-42) | " | (A-II-42) |
| (I-8-43) | " | (A-II-43) |
| (I-8-44) | " | (A-II-44) |
| (I-8-45) | " | (A-II-45) |
| (I-8-46) | " | (A-II-46) |
| (I-8-47) | " | (A-II-47) |
| (I-8-48) | " | (A-II-48) |
| (I-8-49) | " | (A-II-49) |
| (I-8-50) | " | (A-II-50) |

The preferred embodiments of the variable groups indicated above, in particular those of Z and $R^1$ to $R^3$, apply to the particularly preferred embodiments shown in the table.

Explicit examples of compounds of the formula (I) are depicted in the following table:

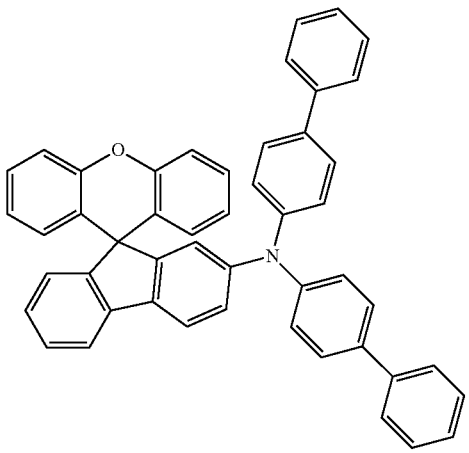 [SMILES: c1ccc(-c2ccc(N(c3ccc(-c4ccccc4)cc3)c3ccc4c(c3)C3(c5ccccc5Oc5ccccc53)c3ccccc3-4)cc2)cc1]

1

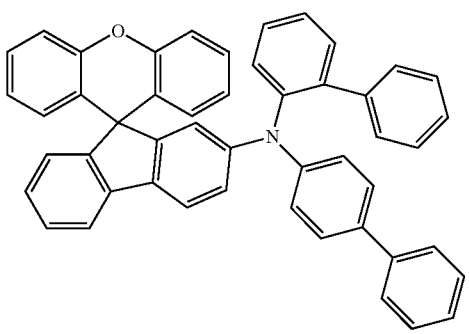 [SMILES: c1ccc(-c2ccc(N(c3ccc4c(c3)C3(c5ccccc5Oc5ccccc53)c3ccccc3-4)c3ccccc3-c3ccccc3)cc2)cc1]

2

-continued
3
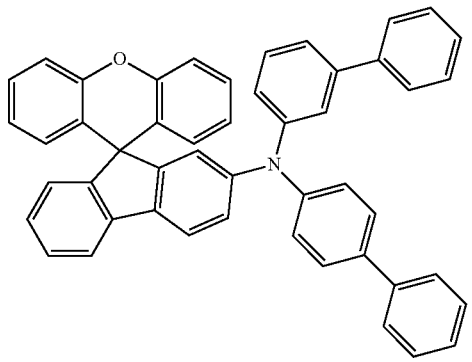 [SMILES: c1ccc(-c2ccc(N(c3cccc(-c4ccccc4)c3)c3ccc4c(c3)C3(c5ccccc5Oc5ccccc53)c3ccccc3-4)cc2)cc1]
4
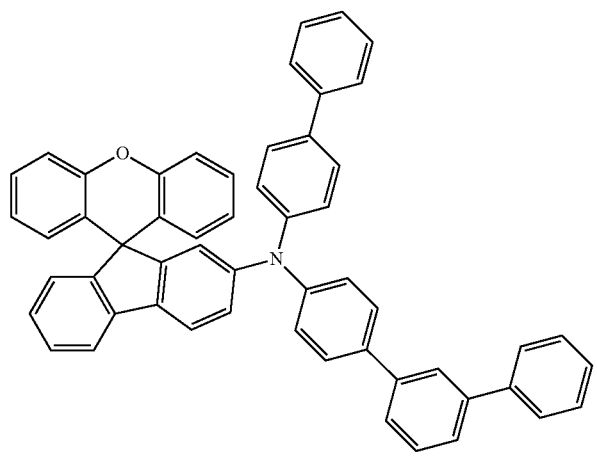 [SMILES: c1ccc(-c2ccc(N(c3ccc(-c4cccc(-c5ccccc5)c4)cc3)c3ccc4c(c3)C3(c5ccccc5Oc5ccccc53)c3ccccc3-4)cc2)cc1]
5
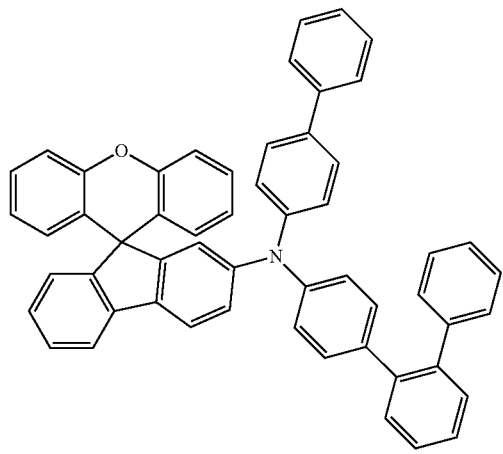 [SMILES: c1ccc(-c2ccc(N(c3ccc(-c4ccccc4-c4ccccc4)cc3)c3ccc4c(c3)C3(c5ccccc5Oc5ccccc53)c3ccccc3-4)cc2)cc1]

6
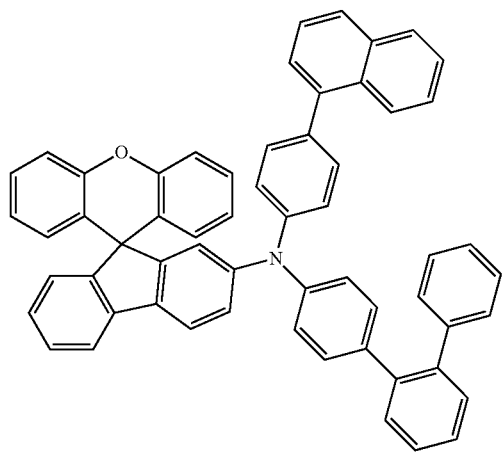 [SMILES: c1ccc(-c2ccccc2-c2ccc(N(c3ccc(-c4cccc5ccccc45)cc3)c3ccc4c(c3)C3(c5ccccc5Oc5ccccc53)c3ccccc3-4)cc2)cc1]
7
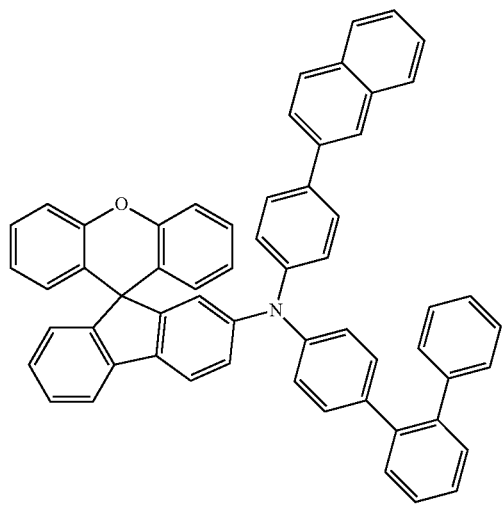 [SMILES: c1ccc(-c2ccccc2-c2ccc(N(c3ccc(-c4ccc5ccccc5c4)cc3)c3ccc4c(c3)C3(c5ccccc5Oc5ccccc53)c3ccccc3-4)cc2)cc1]
8
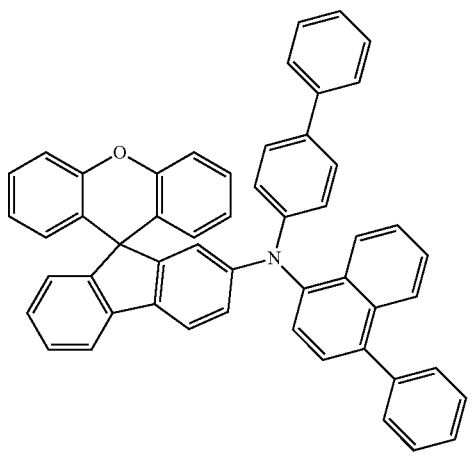 [SMILES: c1ccc(-c2ccc(N(c3ccc4c(c3)C3(c5ccccc5Oc5ccccc53)c3ccccc3-4)c3ccc(-c4ccccc4)c4ccccc34)cc2)cc1]

-continued
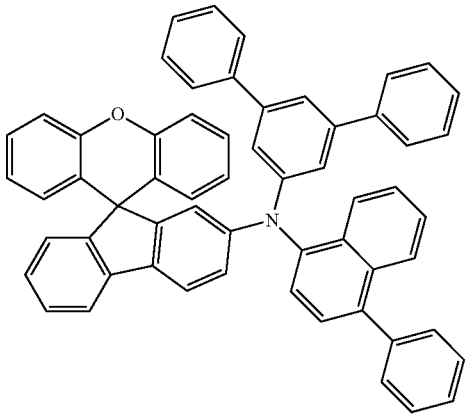 [SMILES: c1ccc(-c2cc(-c3ccccc3)cc(N(c3ccc4c(c3)C3(c5ccccc5Oc5ccccc53)c3ccccc3-4)c3ccc(-c4ccccc4)c4ccccc34)c2)cc1]
9
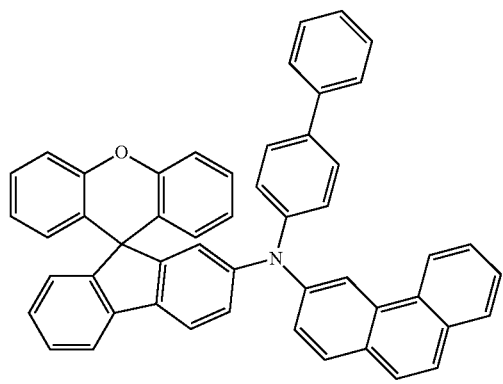 [SMILES: c1ccc(-c2ccc(N(c3ccc4c(c3)C3(c5ccccc5Oc5ccccc53)c3ccccc3-4)c3ccc4ccc5ccccc5c4c3)cc2)cc1]
10
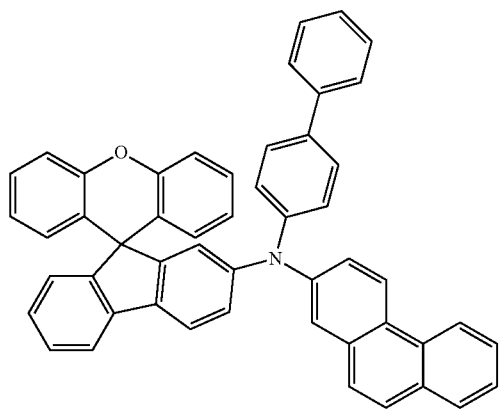 [SMILES: c1ccc(-c2ccc(N(c3ccc4c(c3)C3(c5ccccc5Oc5ccccc53)c3ccccc3-4)c3ccc4c(ccc5ccccc54)c3)cc2)cc1]
11
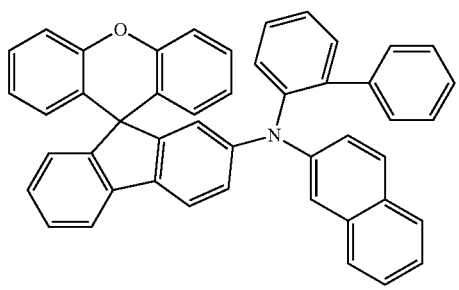 [SMILES: c1ccc(-c2ccccc2N(c2ccc3c(c2)C2(c4ccccc4Oc4ccccc42)c2ccccc2-3)c2ccc3ccccc3c2)cc1]
12

-continued
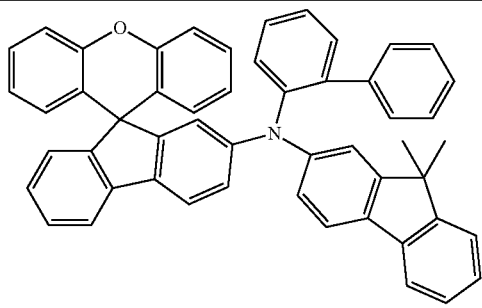
13
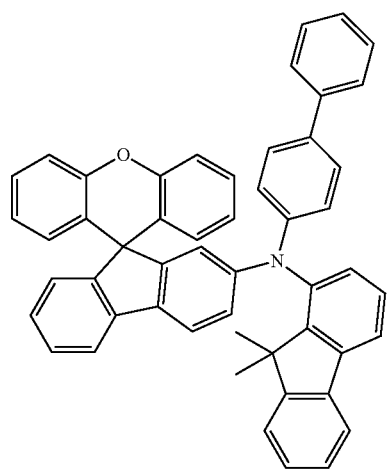 [SMILES: CC1(C)c2ccccc2-c2cccc(N(c3ccc(-c4ccccc4)cc3)c3ccc4c(c3)C3(c5ccccc5Oc5ccccc53)c3ccccc3-4)c21]
14
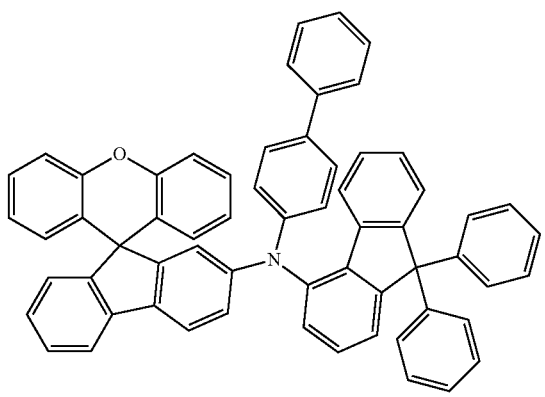 [SMILES: c1ccc(-c2ccc(N(c3ccc4c(c3)C3(c5ccccc5Oc5ccccc53)c3ccccc3-4)c3cccc4c3-c3ccccc3C4(c3ccccc3)c3ccccc3)cc2)cc1]
15
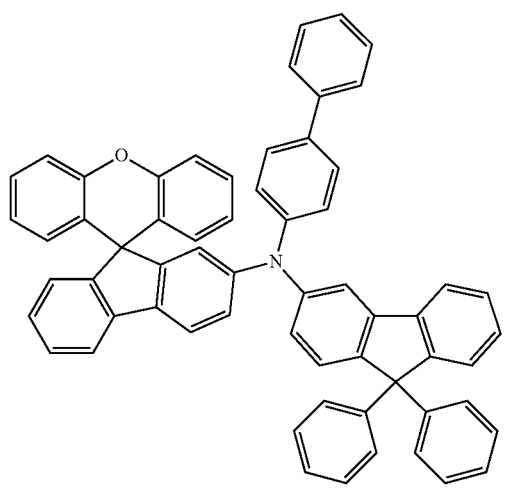 [SMILES: c1ccc(-c2ccc(N(c3ccc4c(c3)-c3ccccc3C4(c3ccccc3)c3ccccc3)c3ccc4c(c3)C3(c5ccccc5Oc5ccccc53)c3ccccc3-4)cc2)cc1]
15

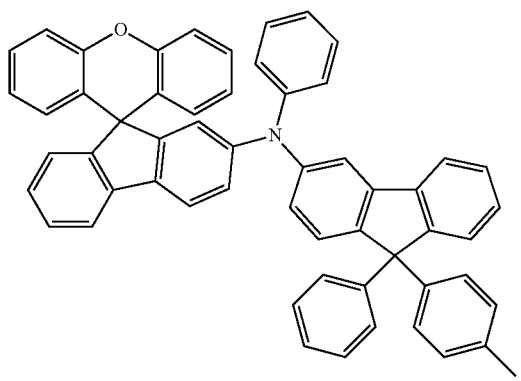 [SMILES: Cc1ccc(C2(c3ccccc3)c3ccccc3-c3cc(N(c4ccccc4)c4ccc5c(c4)C4(c6ccccc6Oc6ccccc64)c4ccccc4-5)ccc32)cc1]
17
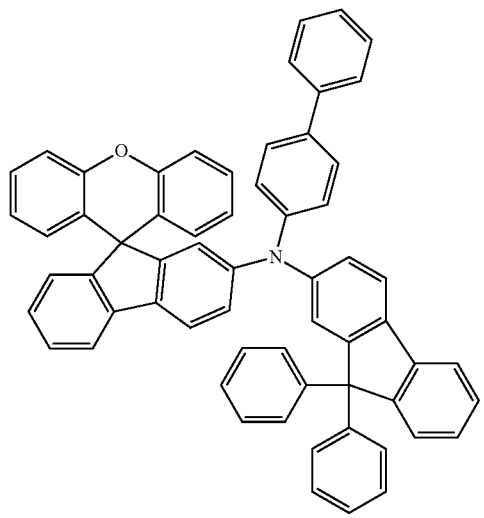 [SMILES: c1ccc(-c2ccc(N(c3ccc4c(c3)C(c3ccccc3)(c3ccccc3)c3ccccc3-4)c3ccc4c(c3)C3(c5ccccc5Oc5ccccc53)c3ccccc3-4)cc2)cc1]
18
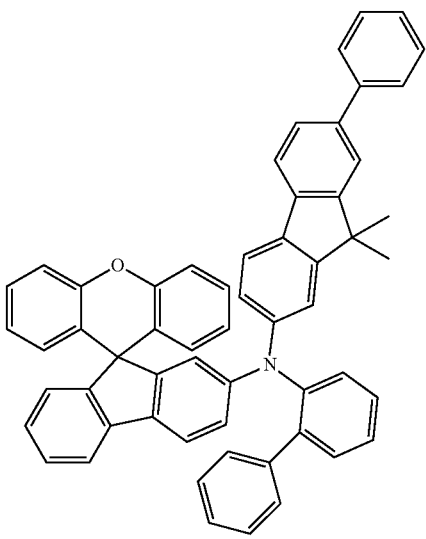 [SMILES: CC1(C)c2cc(-c3ccccc3)ccc2-c2ccc(N(c3ccc4c(c3)C3(c5ccccc5Oc5ccccc53)c3ccccc3-4)c3ccccc3-c3ccccc3)cc21]
19

-continued
20
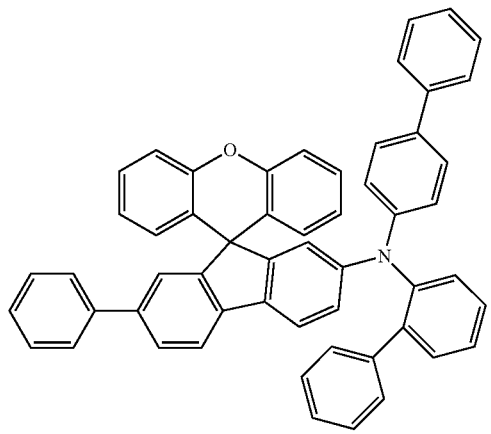 [SMILES: c1ccc(-c2ccc(N(c3ccc4c(c3)C3(c5ccccc5Oc5ccccc53)c3cc(-c5ccccc5)ccc3-4)c3ccccc3-c3ccccc3)cc2)cc1]
21
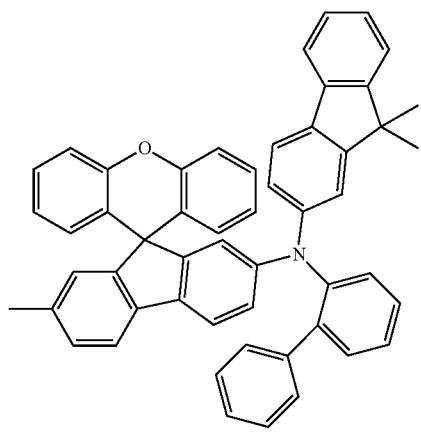
22
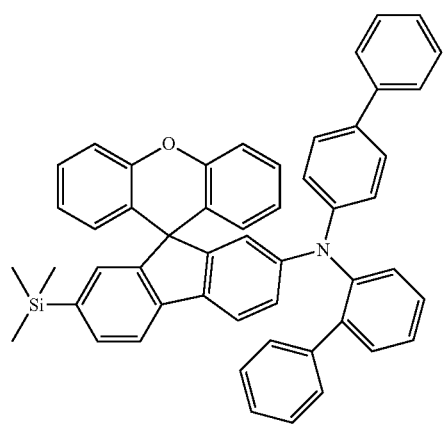 [SMILES: C[Si](C)(C)c1ccc2c(c1)C1(c3ccccc3Oc3ccccc31)c1cc(N(c3ccc(-c4ccccc4)cc3)c3ccccc3-c3ccccc3)ccc1-2]

-continued
23
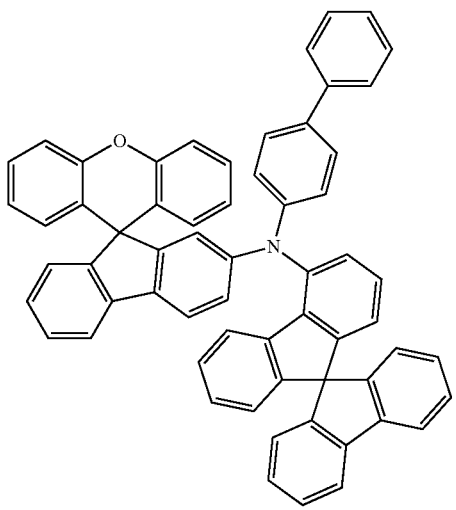 [SMILES: c1ccc(-c2ccc(N(c3ccc4c(c3)C3(c5ccccc5Oc5ccccc53)c3ccccc3-4)c3cccc4c3-c3ccccc3C43c4ccccc4-c4ccccc43)cc2)cc1]
24
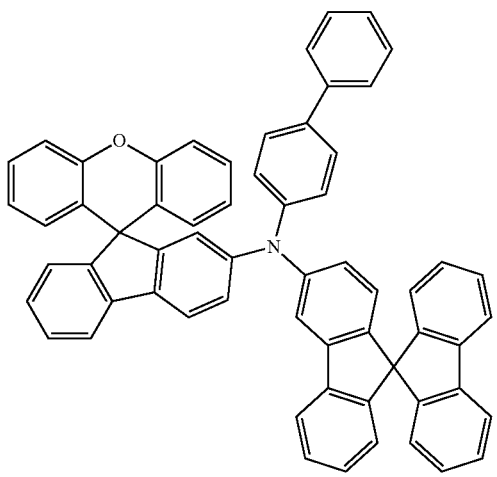 [SMILES: c1ccc(-c2ccc(N(c3ccc4c(c3)-c3ccccc3C43c4ccccc4-c4ccccc43)c3ccc4c(c3)C3(c5ccccc5Oc5ccccc53)c3ccccc3-4)cc2)cc1]
25
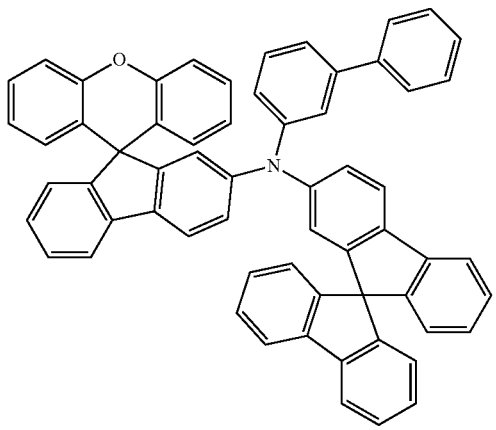 [SMILES: c1ccc(-c2cccc(N(c3ccc4c(c3)C3(c5ccccc5Oc5ccccc53)c3ccccc3-4)c3ccc4c(c3)C3(c5ccccc5-c5ccccc53)c3ccccc3-4)c2)cc1]

-continued
26
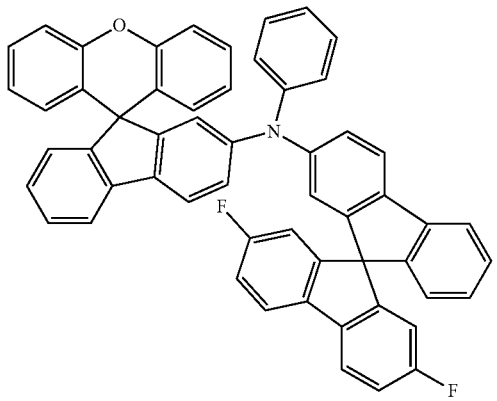 [SMILES: Fc1ccc2c(c1)C1(c3ccccc3-c3ccc(N(c4ccccc4)c4ccc5c(c4)C4(c6ccccc6Oc6ccccc64)c4ccccc4-5)cc31)c1cc(F)ccc1-2]
27
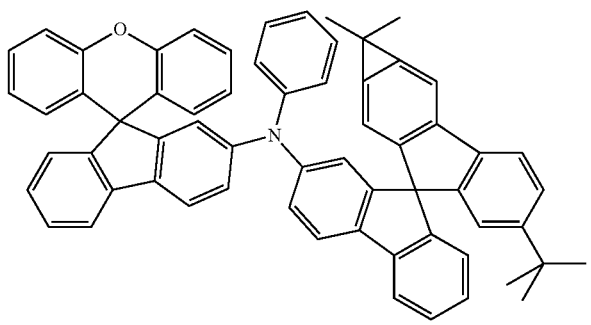 [SMILES: CC(C)(C)c1ccc2c(c1)C1(c3ccccc3-c3ccc(N(c4ccccc4)c4ccc5c(c4)C4(c6ccccc6Oc6ccccc64)c4ccccc4-5)cc31)c1cc3c(cc1-2)C3(C)C]
28
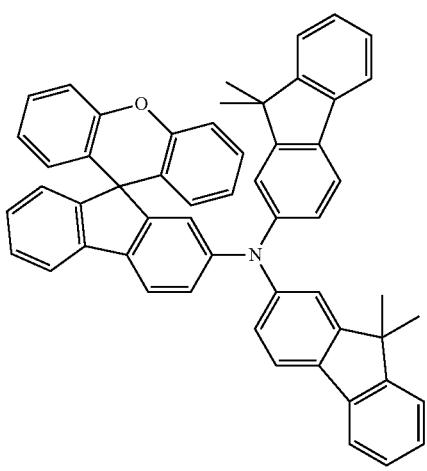 [SMILES: CC1(C)c2ccccc2-c2ccc(N(c3ccc4c(c3)C(C)(C)c3ccccc3-4)c3ccc4c(c3)C3(c5ccccc5Oc5ccccc53)c3ccccc3-4)cc21]

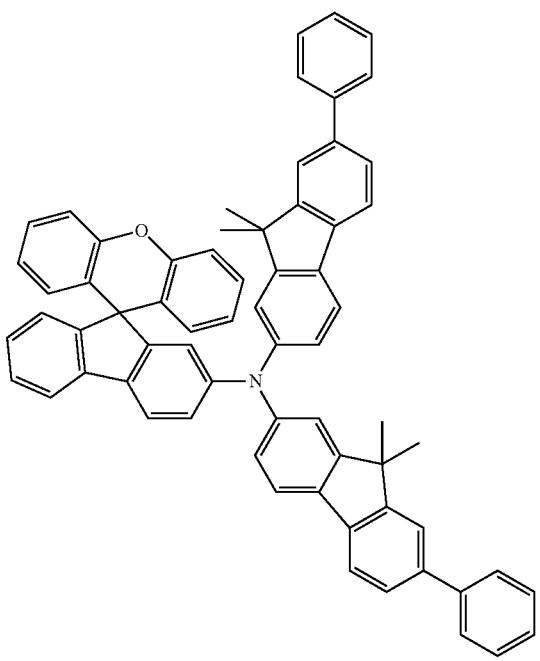 [SMILES: CC1(C)c2cc(-c3ccccc3)ccc2-c2ccc(N(c3ccc4c(c3)C(C)(C)c3cc(-c5ccccc5)ccc3-4)c3ccc4c(c3)C3(c5ccccc5Oc5ccccc53)c3ccccc3-4)cc21]
29
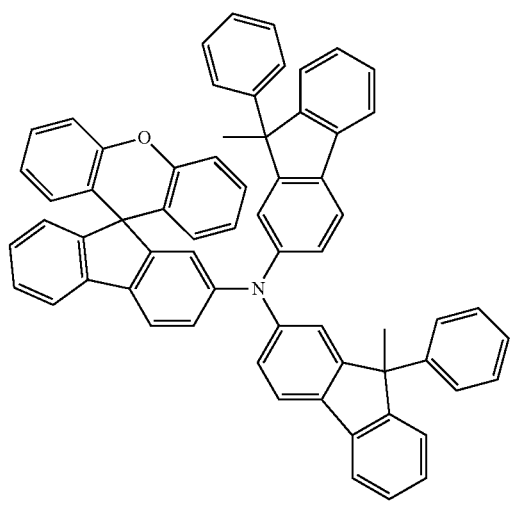 [SMILES: CC1(c2ccccc2)c2ccccc2-c2ccc(N(c3ccc4c(c3)C(C)(c3ccccc3)c3ccccc3-4)c3ccc4c(c3)C3(c5ccccc5Oc5ccccc53)c3ccccc3-4)cc21]
30
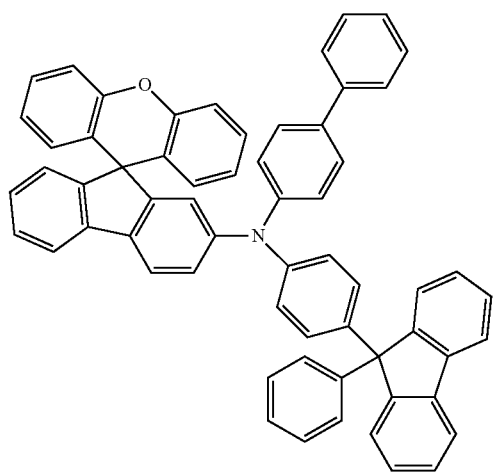 [SMILES: c1ccc(-c2ccc(N(c3ccc(C4(c5ccccc5)c5ccccc5-c5ccccc54)cc3)c3ccc4c(c3)C3(c5ccccc5Oc5ccccc53)c3ccccc3-4)cc2)cc1]
31

-continued
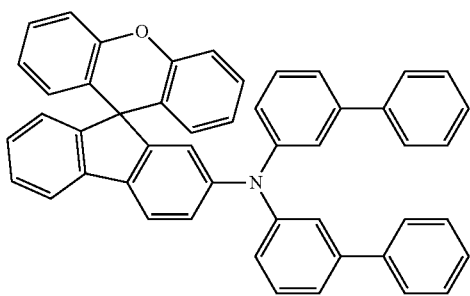 [SMILES: c1ccc(-c2cccc(N(c3cccc(-c4ccccc4)c3)c3ccc4c(c3)C3(c5ccccc5Oc5ccccc53)c3ccccc3-4)c2)cc1]
32
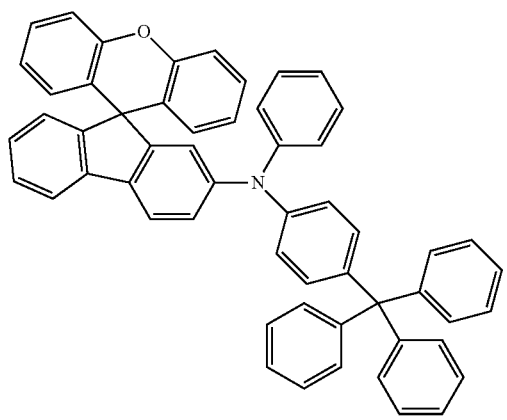 [SMILES: c1ccc(N(c2ccc(C(c3ccccc3)(c3ccccc3)c3ccccc3)cc2)c2ccc3c(c2)C2(c4ccccc4Oc4ccccc42)c2ccccc2-3)cc1]
33
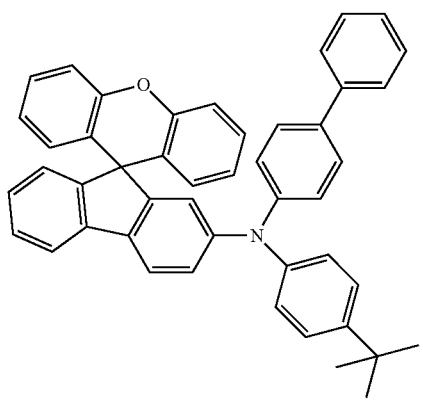 [SMILES: C[Si](C)(C)c1ccc(N(c2ccc(-c3ccccc3)cc2)c2ccc3c(c2)C2(c4ccccc4Oc4ccccc42)c2ccccc2-3)cc1]
34
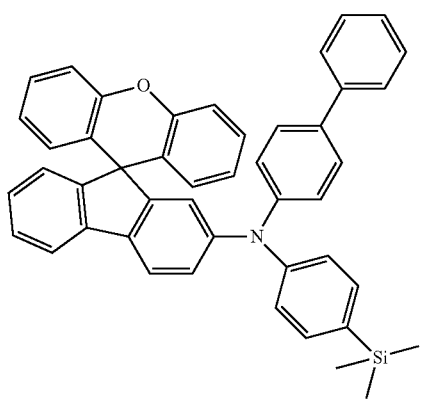
35

36
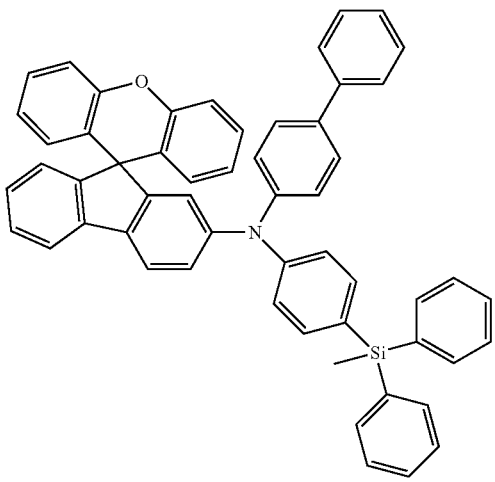 [SMILES: C[Si](c1ccccc1)(c1ccccc1)c1ccc(N(c2ccc(-c3ccccc3)cc2)c2ccc3c(c2)C2(c4ccccc4Oc4ccccc42)c2ccccc2-3)cc1]
37
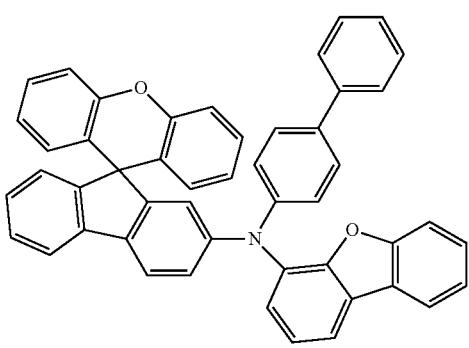 [SMILES: c1ccc(-c2ccc(N(c3ccc4c(c3)C3(c5ccccc5Oc5ccccc53)c3ccccc3-4)c3cccc4c3oc3ccccc34)cc2)cc1]
38
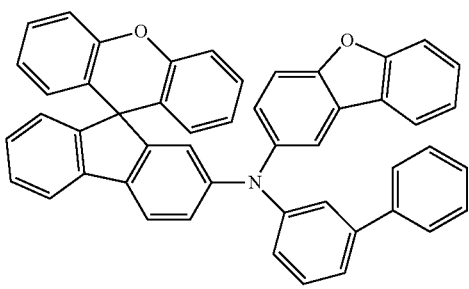 [SMILES: c1ccc(-c2cccc(N(c3ccc4c(c3)C3(c5ccccc5Oc5ccccc53)c3ccccc3-4)c3ccc4oc5ccccc5c4c3)c2)cc1]
39
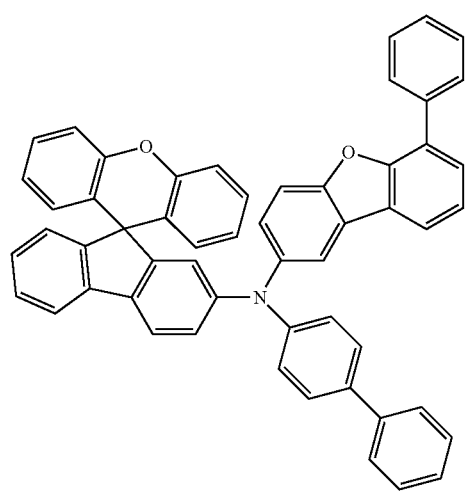 [SMILES: c1ccc(-c2ccc(N(c3ccc4c(c3)C3(c5ccccc5Oc5ccccc53)c3ccccc3-4)c3ccc4oc5c(-c6ccccc6)cccc5c4c3)cc2)cc1]

-continued
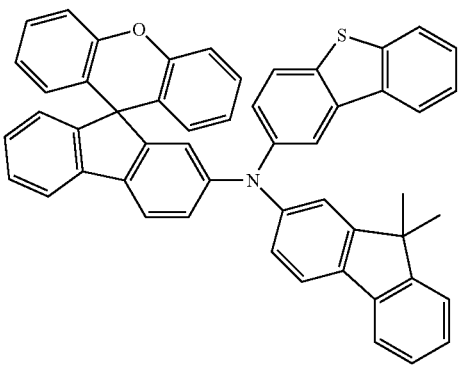 [SMILES: CC1(C)c2ccccc2-c2ccc(N(c3ccc4c(c3)C3(c5ccccc5Oc5ccccc53)c3ccccc3-4)c3ccc4sc5ccccc5c4c3)cc21]
40
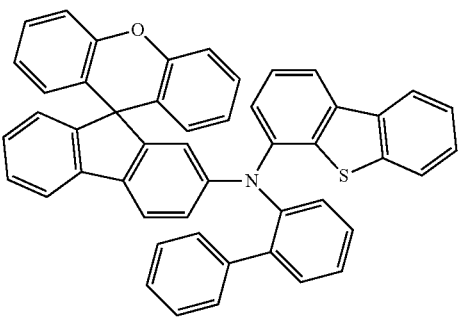 [SMILES: c1ccc(-c2ccccc2N(c2ccc3c(c2)C2(c4ccccc4Oc4ccccc42)c2ccccc2-3)c2cccc3c2sc2ccccc23)cc1]
41
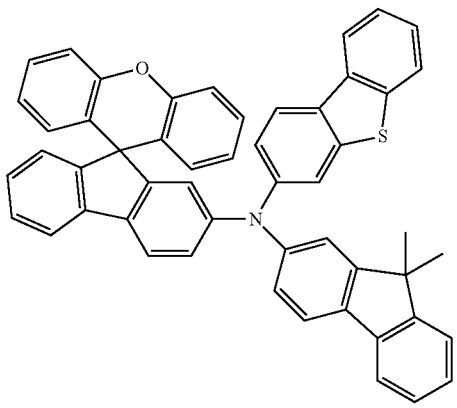 [SMILES: CC1(C)c2ccccc2-c2ccc(N(c3ccc4c(c3)C3(c5ccccc5Oc5ccccc53)c3ccccc3-4)c3ccc4c(c3)sc3ccccc34)cc21]
42
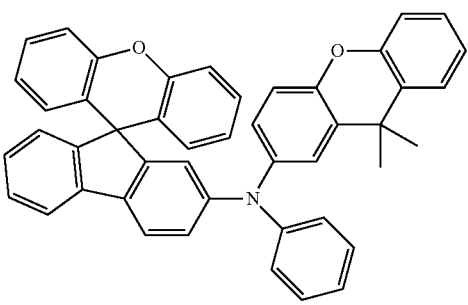 [SMILES: CC1(C)c2ccccc2Oc2ccc(N(c3ccccc3)c3ccc4c(c3)C3(c5ccccc5Oc5ccccc53)c3ccccc3-4)cc21]
43

-continued
44
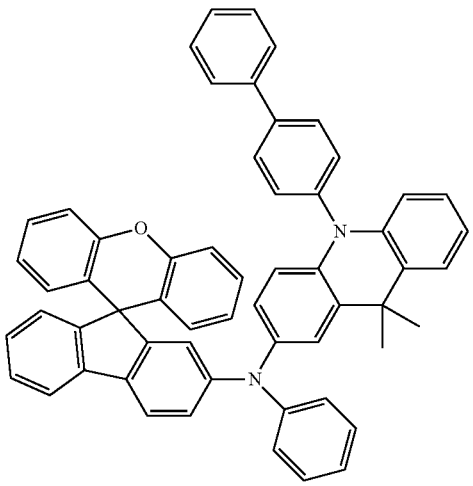 [SMILES: CC1(C)c2ccccc2N(c2ccc(-c3ccccc3)cc2)c2ccc(N(c3ccccc3)c3ccc4c(c3)C3(c5ccccc5Oc5ccccc53)c3ccccc3-4)cc21]
45
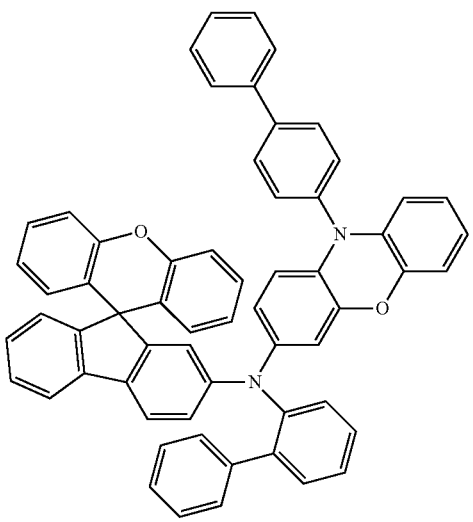 [SMILES: c1ccc(-c2ccc(N3c4ccccc4Oc4cc(N(c5ccc6c(c5)C5(c7ccccc7Oc7ccccc75)c5ccccc5-6)c5ccccc5-c5ccccc5)ccc43)cc2)cc1]
46
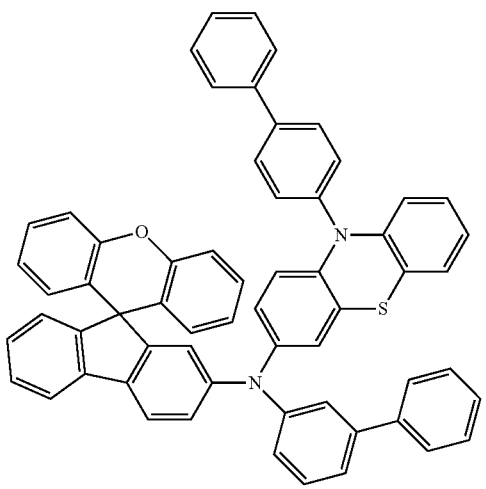 [SMILES: c1ccc(-c2ccc(N3c4ccccc4Sc4cc(N(c5cccc(-c6ccccc6)c5)c5ccc6c(c5)C5(c7ccccc7Oc7ccccc75)c5ccccc5-6)ccc43)cc2)cc1]

47
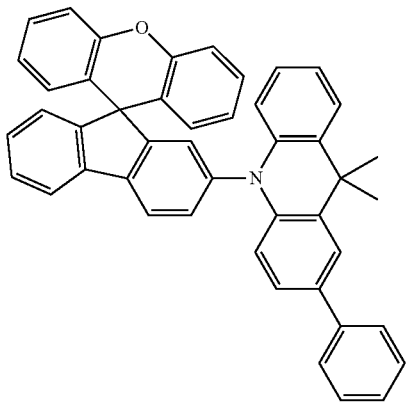 [SMILES: CC1(C)c2ccccc2N(c2ccc3c(c2)C2(c4ccccc4Oc4ccccc42)c2ccccc2-3)c2ccc(-c3ccccc3)cc21]
48
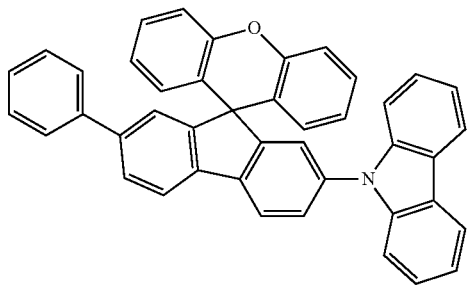 [SMILES: c1ccc(-c2ccc3c(c2)C2(c4ccccc4Oc4ccccc42)c2cc(-n4c5ccccc5c5ccccc54)ccc2-3)cc1]
49
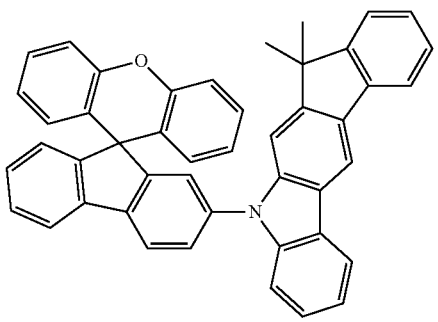 [SMILES: CC1(C)c2ccccc2-c2cc3c4ccccc4n(-c4ccc5c(c4)C4(c6ccccc6Oc6ccccc64)c4ccccc4-5)c3cc21]
50
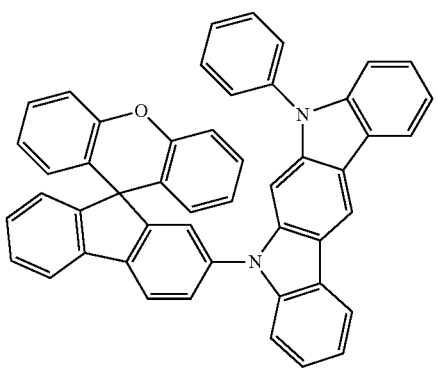 [SMILES: c1ccc(-n2c3ccccc3c3cc4c5ccccc5n(-c5ccc6c(c5)C5(c7ccccc7Oc7ccccc75)c5ccccc5-6)c4cc32)cc1]

-continued
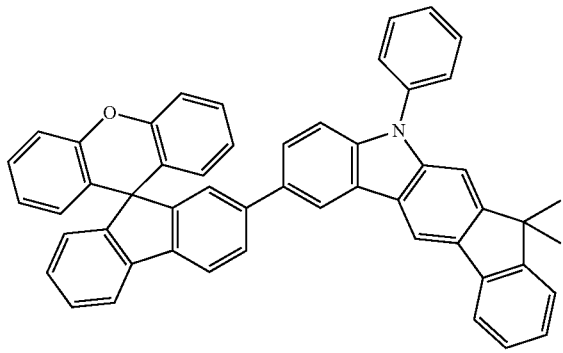 [SMILES: CC1(C)c2ccccc2-c2cc3c4cc(-c5ccc6c(c5)C5(c7ccccc7Oc7ccccc75)c5ccccc5-6)ccc4n(-c4ccccc4)c3cc21]
51
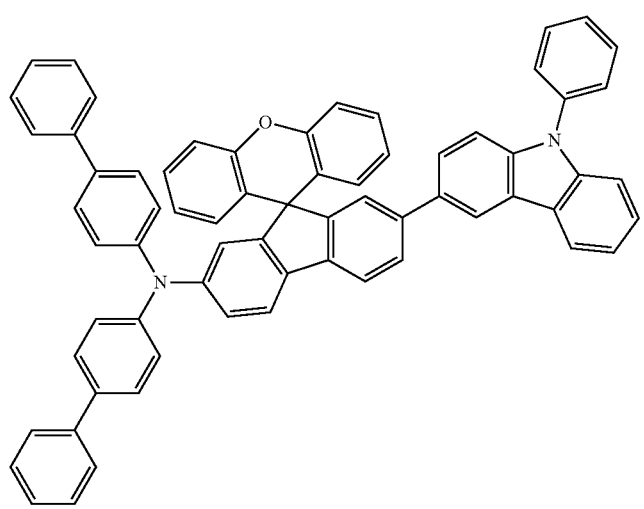 [SMILES: c1ccc(-c2ccc(N(c3ccc(-c4ccccc4)cc3)c3ccc4c(c3)C3(c5ccccc5Oc5ccccc53)c3cc(-c5ccc6c(c5)c5ccccc5n6-c5ccccc5)ccc3-4)cc2)cc1]
52
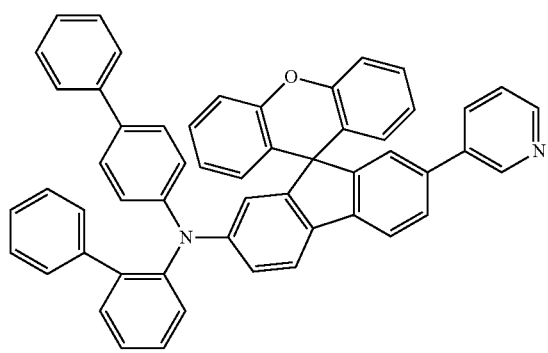 [SMILES: c1ccc(-c2ccc(N(c3ccc4c(c3)C3(c5ccccc5Oc5ccccc53)c3cc(-c5cccnc5)ccc3-4)c3ccccc3-c3ccccc3)cc2)cc1]
53
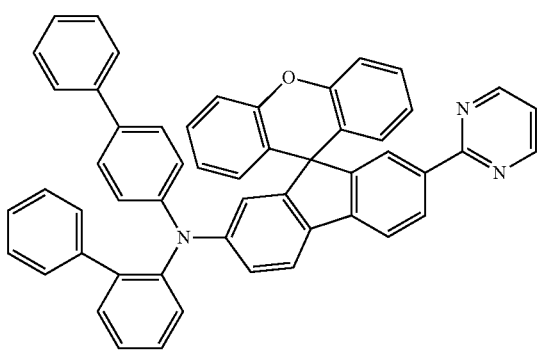 [SMILES: c1ccc(-c2ccc(N(c3ccc4c(c3)C3(c5ccccc5Oc5ccccc53)c3cc(-c5ncccn5)ccc3-4)c3ccccc3-c3ccccc3)cc2)cc1]
54

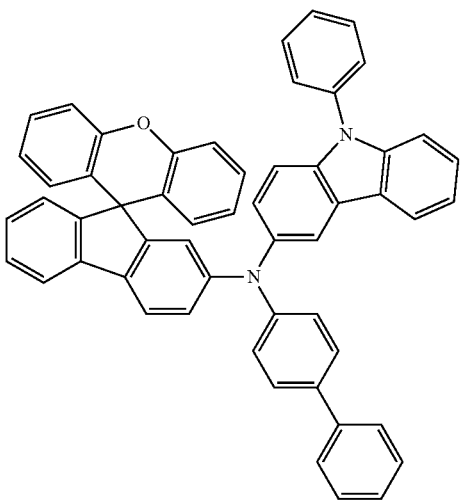 [SMILES: c1ccc(-c2ccc(N(c3ccc4c(c3)C3(c5ccccc5Oc5ccccc53)c3ccccc3-4)c3ccc4c(c3)c3ccccc3n4-c3ccccc3)cc2)cc1]
55
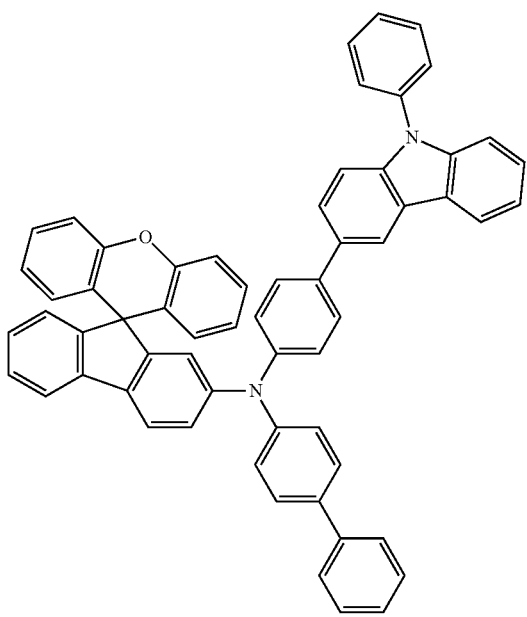 [SMILES: c1ccc(-c2ccc(N(c3ccc(-c4ccc5c(c4)c4ccccc4n5-c4ccccc4)cc3)c3ccc4c(c3)C3(c5ccccc5Oc5ccccc53)c3ccccc3-4)cc2)cc1]
56
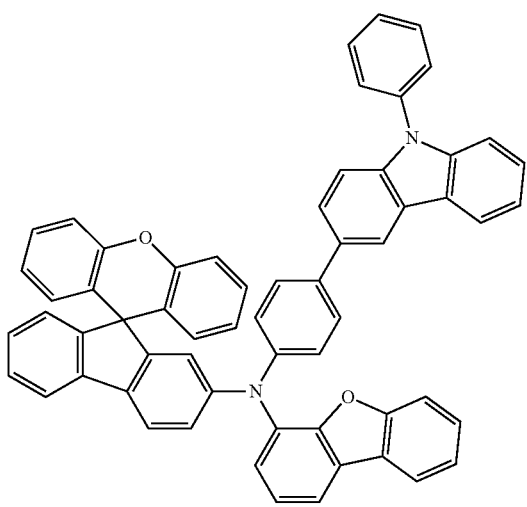 [SMILES: c1ccc(-n2c3ccccc3c3cc(-c4ccc(N(c5ccc6c(c5)C5(c7ccccc7Oc7ccccc75)c5ccccc5-6)c5cccc6c5oc5ccccc56)cc4)ccc32)cc1]
57

58
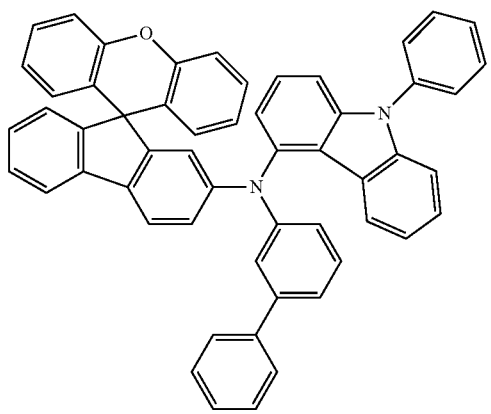 [SMILES: c1ccc(-c2cccc(N(c3ccc4c(c3)C3(c5ccccc5Oc5ccccc53)c3ccccc3-4)c3cccc4c3c3ccccc3n4-c3ccccc3)c2)cc1]
59
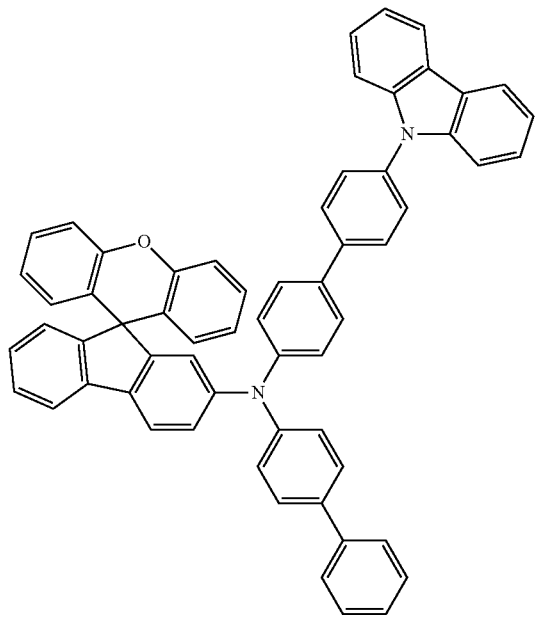 [SMILES: c1ccc(-c2ccc(N(c3ccc(-c4ccc(-n5c6ccccc6c6ccccc65)cc4)cc3)c3ccc4c(c3)C3(c5ccccc5Oc5ccccc53)c3ccccc3-4)cc2)cc1]
60
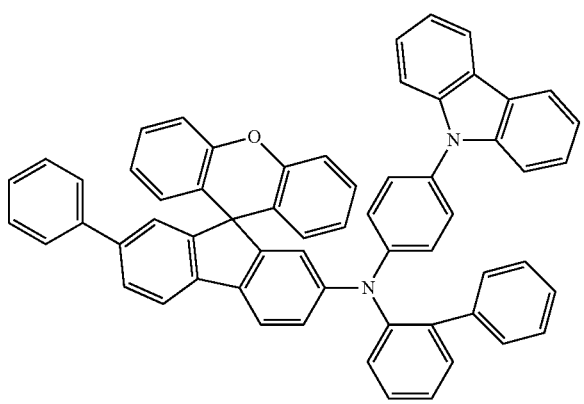 [SMILES: c1ccc(-c2ccc3c(c2)C2(c4ccccc4Oc4ccccc42)c2cc(N(c4ccc(-n5c6ccccc6c6ccccc65)cc4)c4ccccc4-c4ccccc4)ccc2-3)cc1]

-continued
61
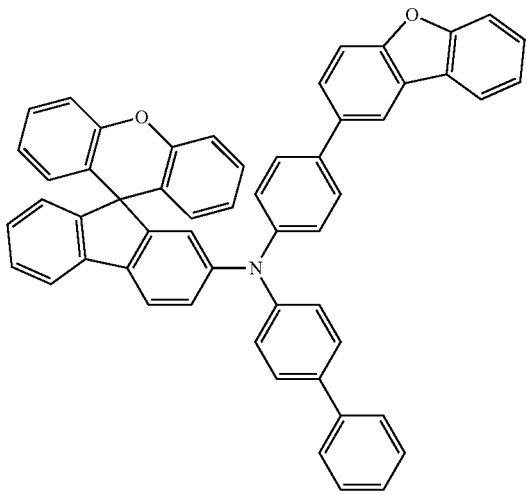 [SMILES: c1ccc(-c2ccc(N(c3ccc(-c4ccc5oc6ccccc6c5c4)cc3)c3ccc4c(c3)C3(c5ccccc5Oc5ccccc53)c3ccccc3-4)cc2)cc1]
62
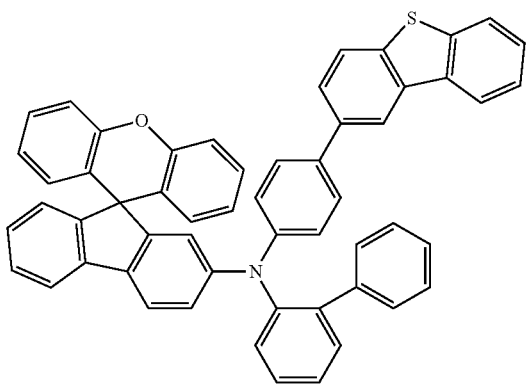 [SMILES: c1ccc(-c2ccccc2N(c2ccc(-c3ccc4sc5ccccc5c4c3)cc2)c2ccc3c(c2)C2(c4ccccc4Oc4ccccc42)c2ccccc2-3)cc1]
63
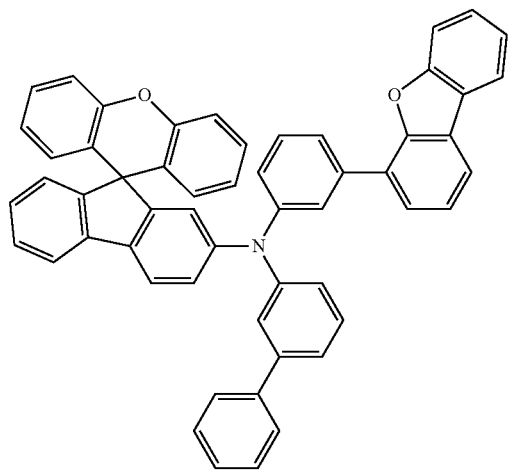 [SMILES: c1ccc(-c2cccc(N(c3cccc(-c4cccc5c4oc4ccccc45)c3)c3ccc4c(c3)C3(c5ccccc5Oc5ccccc53)c3ccccc3-4)c2)cc1]

-continued
64
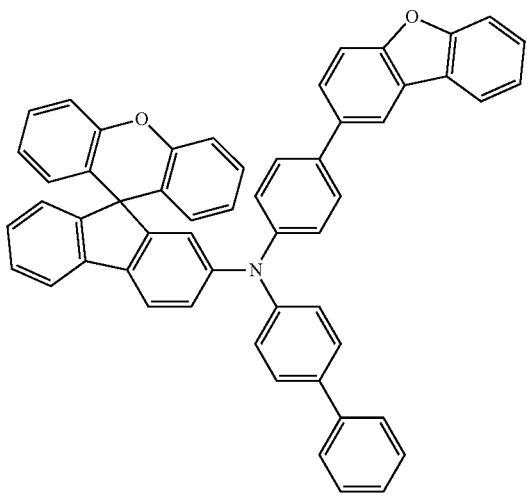 [SMILES: c1ccc(-c2ccc(N(c3ccc(-c4ccc5oc6ccccc6c5c4)cc3)c3ccc4c(c3)C3(c5ccccc5Oc5ccccc53)c3ccccc3-4)cc2)cc1]
65
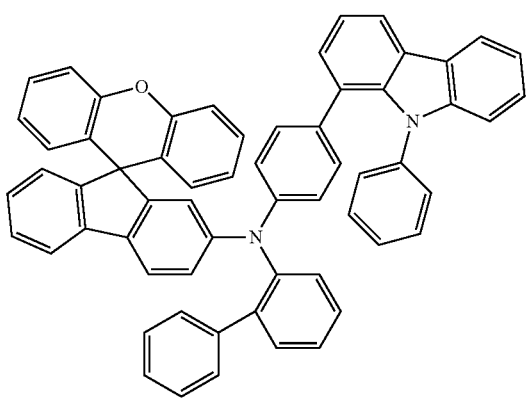 [SMILES: c1ccc(-c2ccccc2N(c2ccc(-c3cccc4c5ccccc5n(-c5ccccc5)c34)cc2)c2ccc3c(c2)C2(c4ccccc4Oc4ccccc42)c2ccccc2-3)cc1]
66
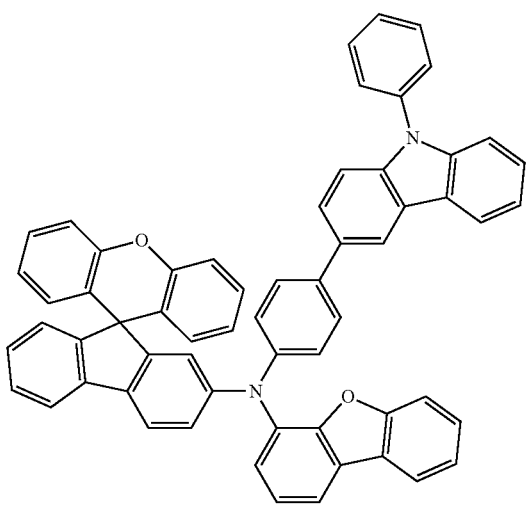 [SMILES: c1ccc(-n2c3ccccc3c3cc(-c4ccc(N(c5ccc6c(c5)C5(c7ccccc7Oc7ccccc75)c5ccccc5-6)c5cccc6c5oc5ccccc56)cc4)ccc32)cc1]

-continued
67
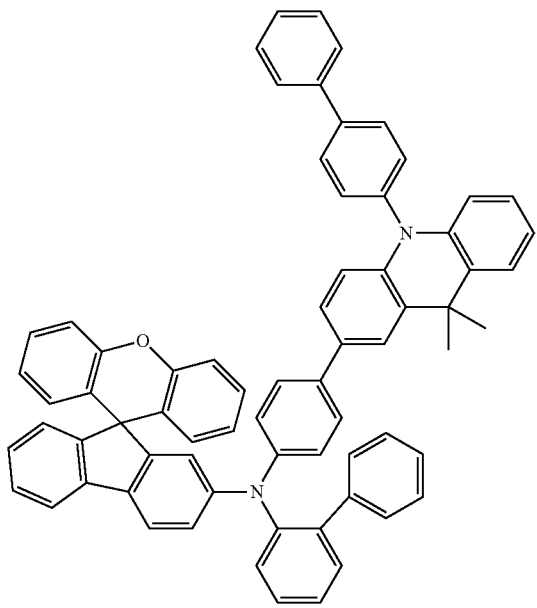 [SMILES: CC1(C)c2ccccc2N(c2ccc(-c3ccccc3)cc2)c2ccc(-c3ccc(N(c4ccc5c(c4)C4(c6ccccc6Oc6ccccc64)c4ccccc4-5)c4ccccc4-c4ccccc4)cc3)cc21]
68
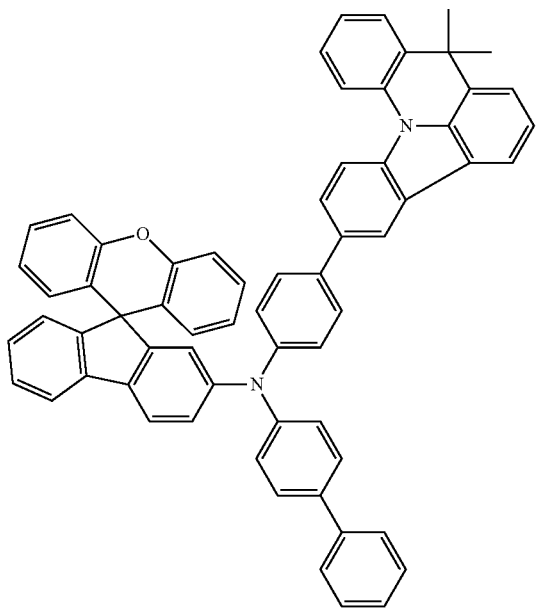 [SMILES: CC1(C)c2ccccc2-n2c3ccc(-c4ccc(N(c5ccc(-c6ccccc6)cc5)c5ccc6c(c5)C5(c7ccccc7Oc7ccccc75)c5ccccc5-6)cc4)cc3c3cccc1c32]

69
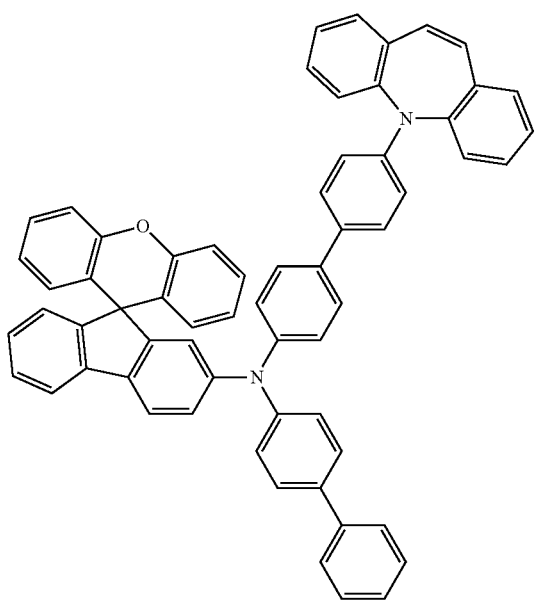 [SMILES: C1=Cc2ccccc2N(c2ccc(-c3ccc(N(c4ccc(-c5ccccc5)cc4)c4ccc5c(c4)C4(c6ccccc6Oc6ccccc64)c4ccccc4-5)cc3)cc2)c2ccccc21]
70
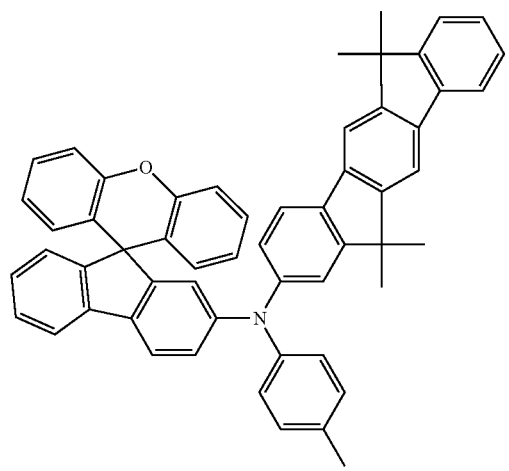 [SMILES: Cc1ccc(N(c2ccc3c(c2)C(C)(C)c2cc4c(cc2-3)C(C)(C)c2ccccc2-4)c2ccc3c(c2)C2(c4ccccc4Oc4ccccc42)c2ccccc2-3)cc1]
71
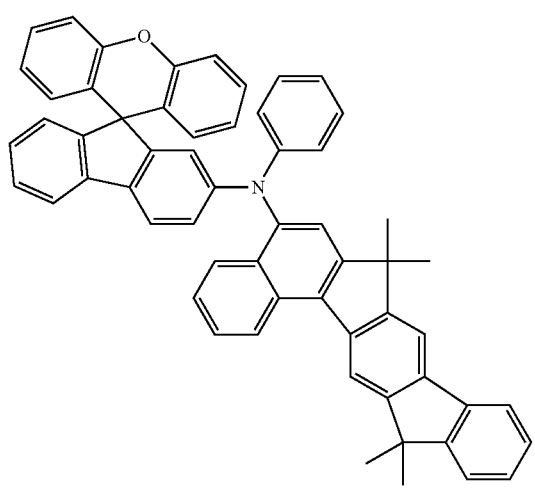 [SMILES: CC1(C)c2ccccc2-c2cc3c(cc21)-c1c(cc(N(c2ccccc2)c2ccc4c(c2)C2(c5ccccc5Oc5ccccc52)c2ccccc2-4)c2ccccc12)C3(C)C]

72
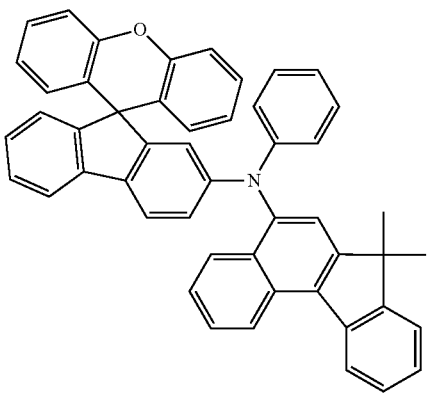 [SMILES: CC1(C)c2ccccc2-c2c1cc(N(c1ccccc1)c1ccc3c(c1)C1(c4ccccc4Oc4ccccc41)c1ccccc1-3)c1ccccc21]
73
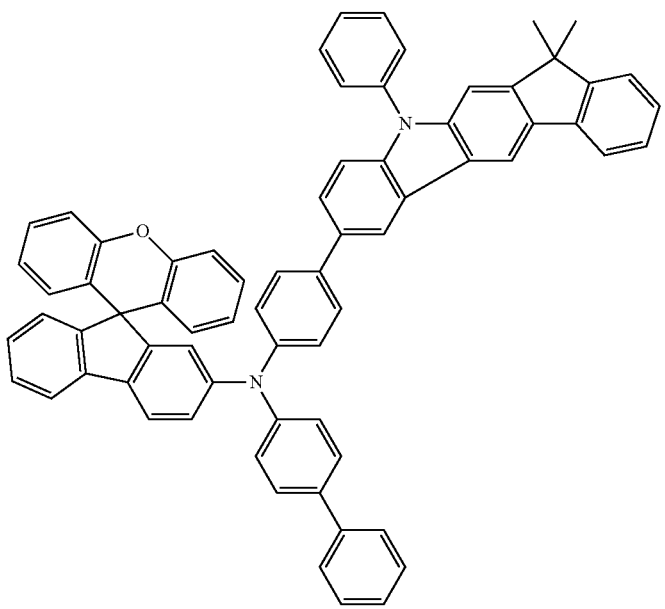 [SMILES: CC1(C)c2ccccc2-c2cc3c4cc(-c5ccc(N(c6ccc(-c7ccccc7)cc6)c6ccc7c(c6)C6(c8ccccc8Oc8ccccc86)c6ccccc6-7)cc5)ccc4n(-c4ccccc4)c3cc21]
74
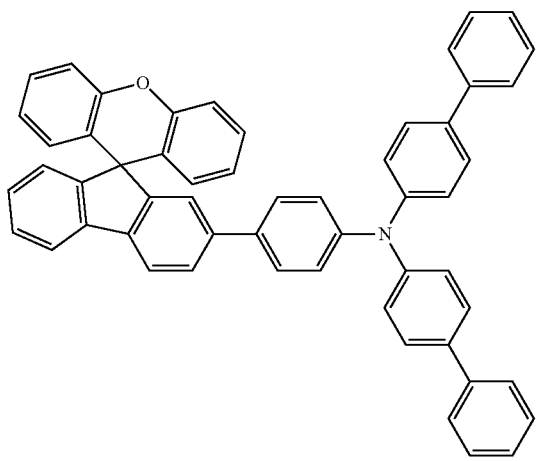 [SMILES: c1ccc(-c2ccc(N(c3ccc(-c4ccccc4)cc3)c3ccc(-c4ccc5c(c4)C4(c6ccccc6Oc6ccccc64)c4ccccc4-5)cc3)cc2)cc1]

-continued
75
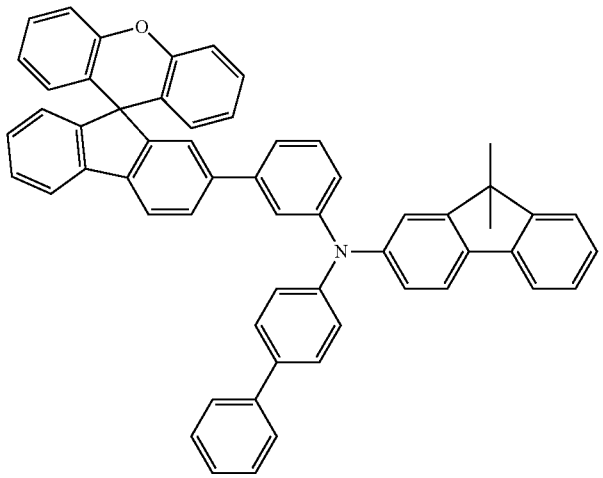
76
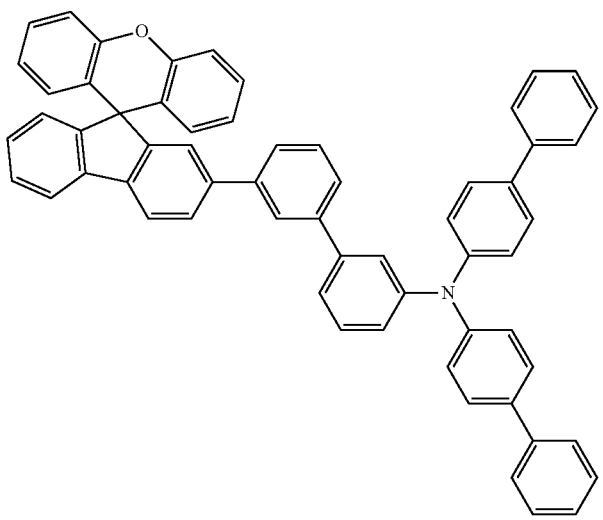 [SMILES: c1ccc(-c2ccc(N(c3ccc(-c4ccccc4)cc3)c3cccc(-c4cccc(-c5ccc6c(c5)C5(c7ccccc7Oc7ccccc75)c5ccccc5-6)c4)c3)cc2)cc1]
77
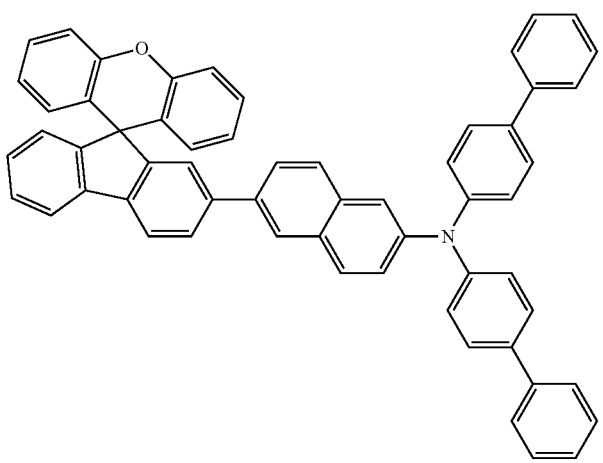 [SMILES: c1ccc(-c2ccc(N(c3ccc(-c4ccccc4)cc3)c3ccc4cc(-c5ccc6c(c5)C5(c7ccccc7Oc7ccccc75)c5ccccc5-6)ccc4c3)cc2)cc1]

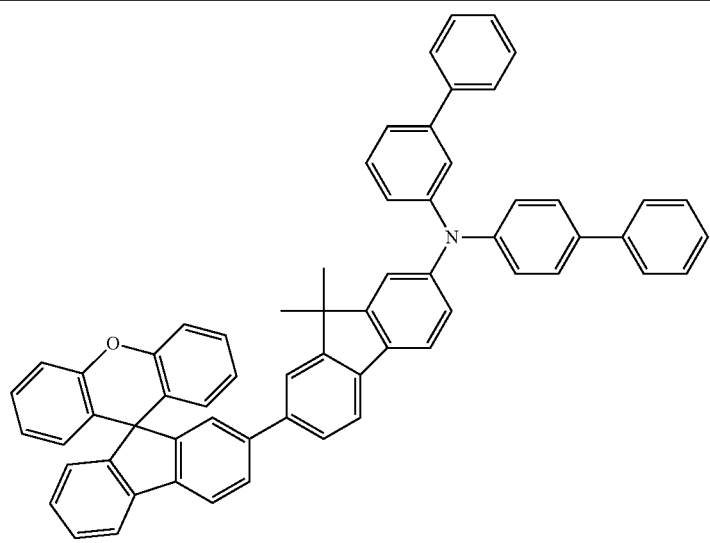
78
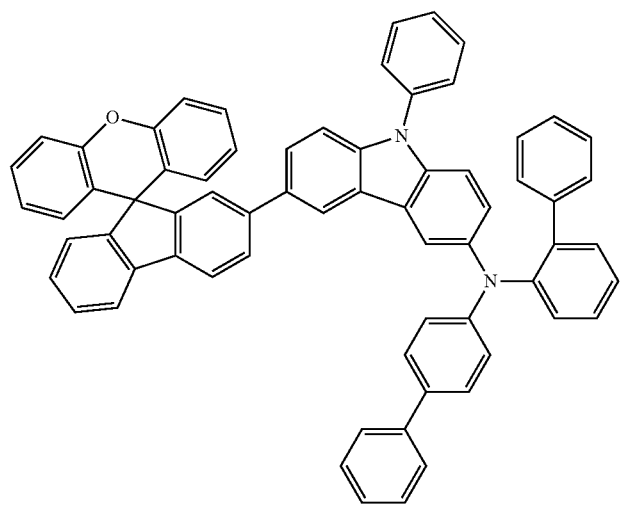 [SMILES: c1ccc(-c2ccc(N(c3ccc4c(c3)c3cc(-c5ccc6c(c5)C5(c7ccccc7Oc7ccccc75)c5ccccc5-6)ccc3n4-c3ccccc3)c3ccccc3-c3ccccc3)cc2)cc1]
79
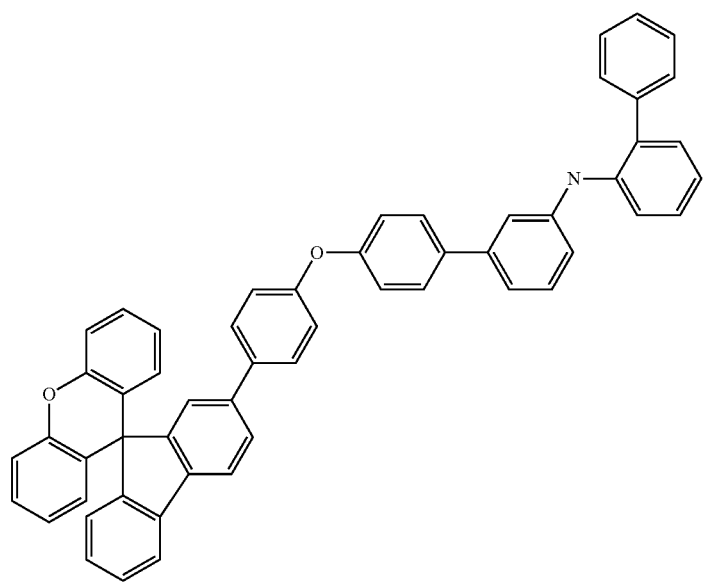 [SMILES: c1ccc(-c2ccccc2Nc2cccc(-c3ccc(Oc4ccc(-c5ccc6c(c5)C5(c7ccccc7Oc7ccccc75)c5ccccc5-6)cc4)cc3)c2)cc1]
80

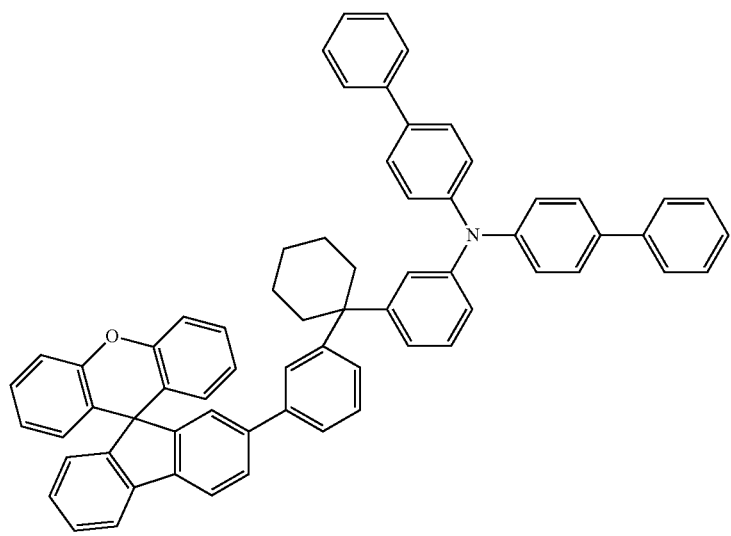 [SMILES: c1ccc(-c2ccc(N(c3ccc(-c4ccccc4)cc3)c3cccc(C4(c5cccc(-c6ccc7c(c6)C6(c8ccccc8Oc8ccccc86)c6ccccc6-7)c5)CCCCC4)c3)cc2)cc1]
81
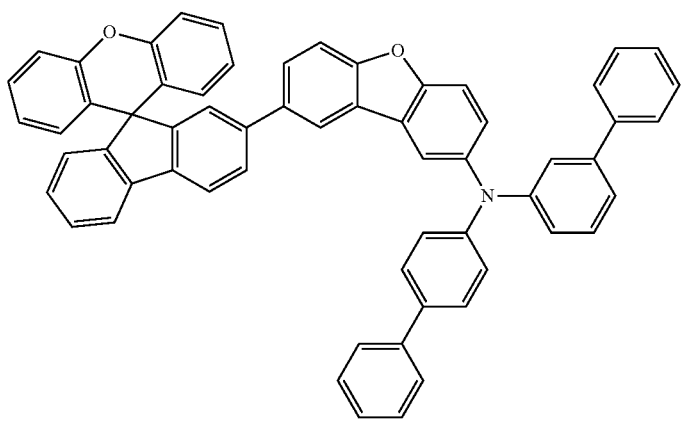 [SMILES: c1ccc(-c2ccc(N(c3cccc(-c4ccccc4)c3)c3ccc4oc5ccc(-c6ccc7c(c6)C6(c8ccccc8Oc8ccccc86)c6ccccc6-7)cc5c4c3)cc2)cc1]
82
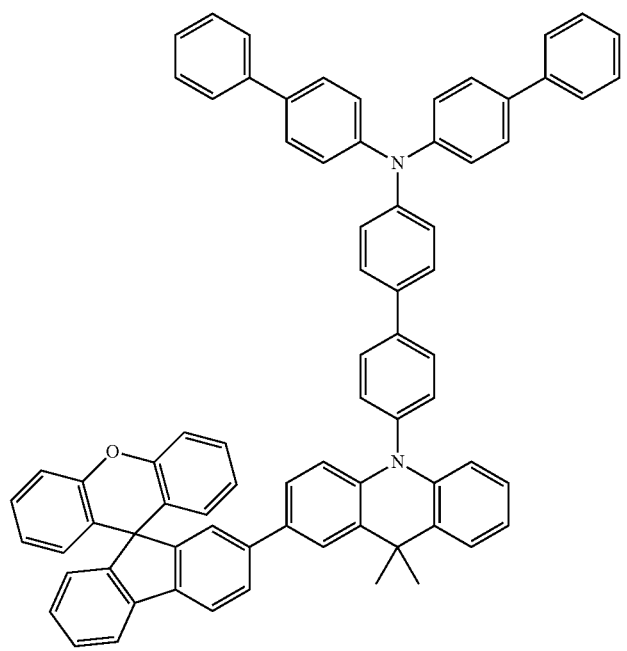 [SMILES: CC1(C)c2ccccc2N(c2ccc(-c3ccc(N(c4ccc(-c5ccccc5)cc4)c4ccc(-c5ccccc5)cc4)cc3)cc2)c2ccc(-c3ccc4c(c3)C3(c5ccccc5Oc5ccccc53)c3ccccc3-4)cc21]
83

-continued
84
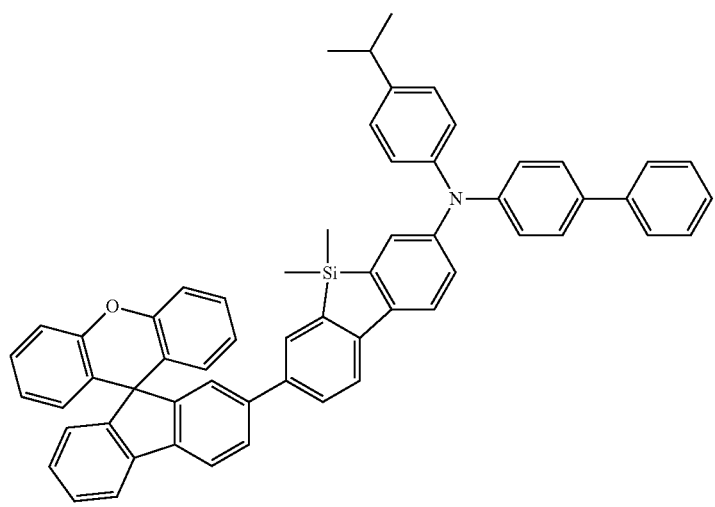 [SMILES: CC(C)c1ccc(N(c2ccc(-c3ccccc3)cc2)c2ccc3c(c2)[Si](C)(C)c2cc(-c4ccc5c(c4)C4(c6ccccc6Oc6ccccc64)c4ccccc4-5)ccc2-3)cc1]
85
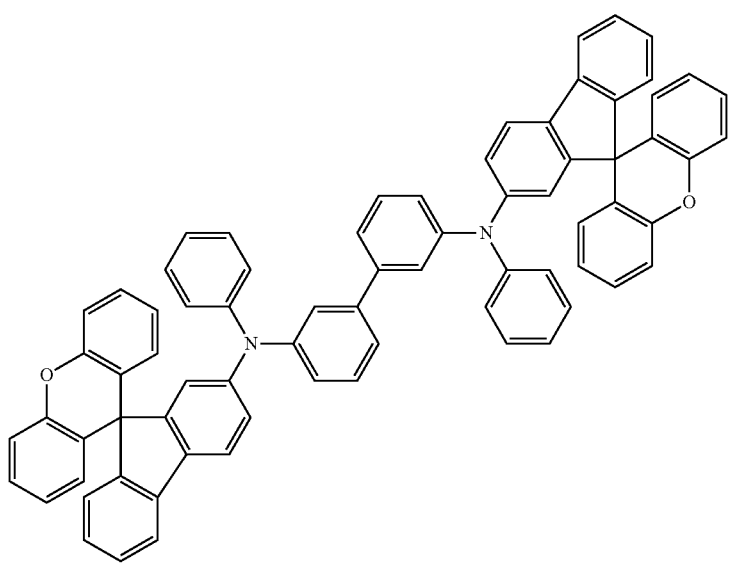 [SMILES: c1ccc(N(c2cccc(-c3cccc(N(c4ccccc4)c4ccc5c(c4)C4(c6ccccc6Oc6ccccc64)c4ccccc4-5)c3)c2)c2ccc3c(c2)C2(c4ccccc4Oc4ccccc42)c2ccccc2-3)cc1]
86
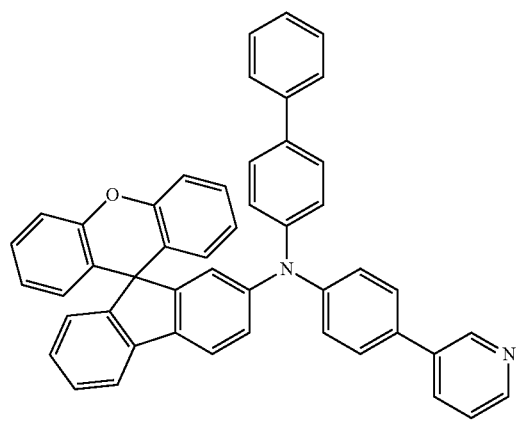 [SMILES: c1ccc(-c2ccc(N(c3ccc(-c4cccnc4)cc3)c3ccc4c(c3)C3(c5ccccc5Oc5ccccc53)c3ccccc3-4)cc2)cc1]

87
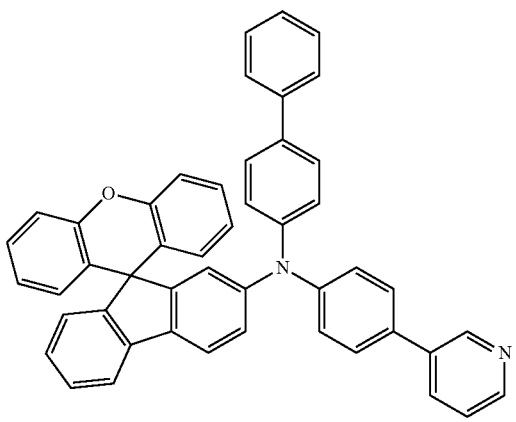 [SMILES: c1ccc(-c2ccc(N(c3ccc(-c4cccnc4)cc3)c3ccc4c(c3)C3(c5ccccc5Oc5ccccc53)c3ccccc3-4)cc2)cc1]
88
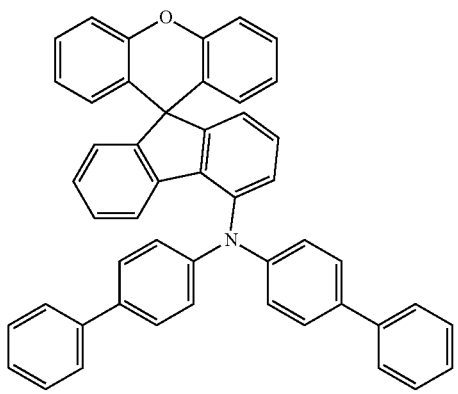 [SMILES: c1ccc(-c2ccc(N(c3ccc(-c4ccccc4)cc3)c3cccc4c3-c3ccccc3C43c4ccccc4Oc4ccccc43)cc2)cc1]
89
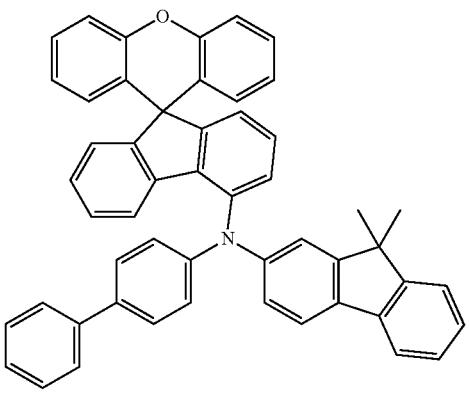 [SMILES: CC1(C)c2ccccc2-c2ccc(N(c3ccc(-c4ccccc4)cc3)c3cccc4c3-c3ccccc3C43c4ccccc4Oc4ccccc43)cc21]
90
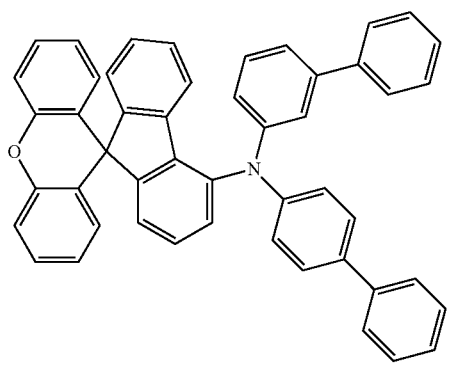 [SMILES: c1ccc(-c2ccc(N(c3cccc(-c4ccccc4)c3)c3cccc4c3-c3ccccc3C43c4ccccc4Oc4ccccc43)cc2)cc1]

91
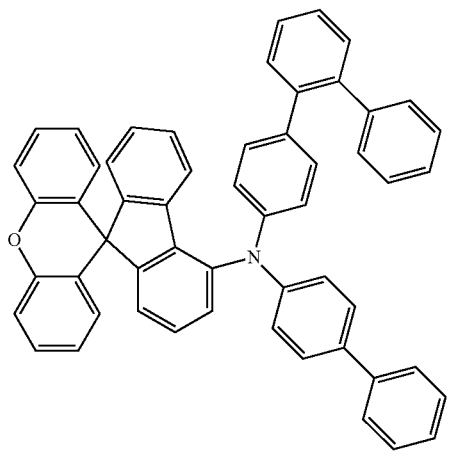 [SMILES: c1ccc(-c2ccc(N(c3ccc(-c4ccccc4-c4ccccc4)cc3)c3cccc4c3-c3ccccc3C43c4ccccc4Oc4ccccc43)cc2)cc1]
92
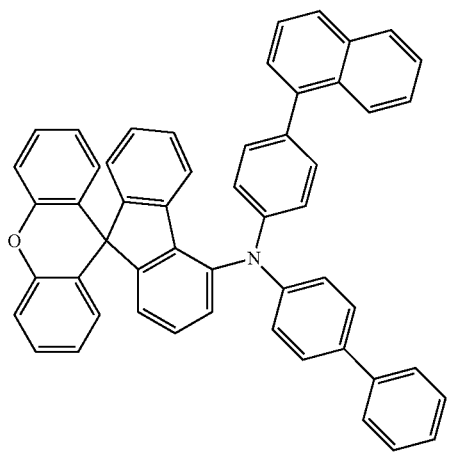 [SMILES: c1ccc(-c2ccc(N(c3ccc(-c4cccc5ccccc45)cc3)c3cccc4c3-c3ccccc3C43c4ccccc4Oc4ccccc43)cc2)cc1]
93
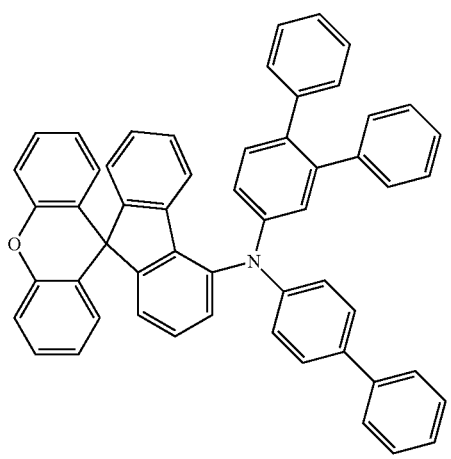 [SMILES: c1ccc(-c2ccc(N(c3ccc(-c4ccccc4)c(-c4ccccc4)c3)c3cccc4c3-c3ccccc3C43c4ccccc4Oc4ccccc43)cc2)cc1]

-continued
94
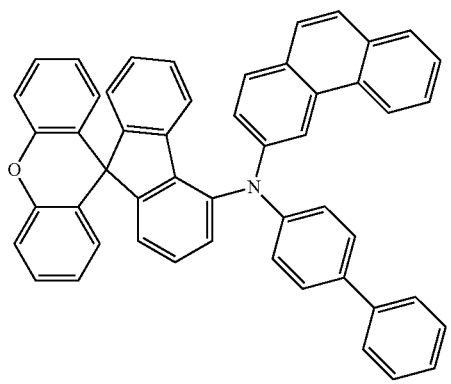 [SMILES: c1ccc(-c2ccc(N(c3ccc4ccc5ccccc5c4c3)c3cccc4c3-c3ccccc3C43c4ccccc4Oc4ccccc43)cc2)cc1]
95
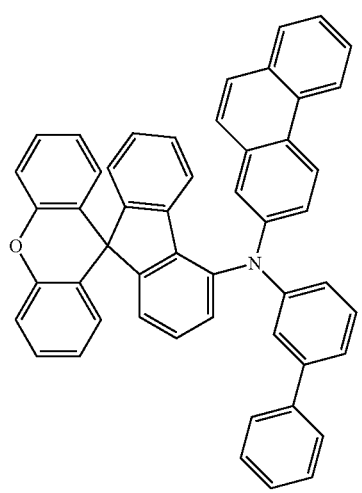 [SMILES: c1ccc(-c2cccc(N(c3ccc4c(ccc5ccccc54)c3)c3cccc4c3-c3ccccc3C43c4ccccc4Oc4ccccc43)c2)cc1]
96
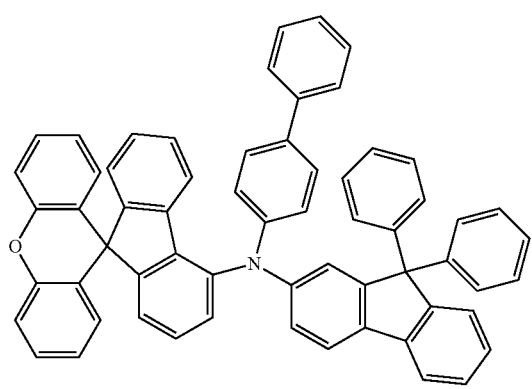 [SMILES: c1ccc(-c2ccc(N(c3ccc4c(c3)C(c3ccccc3)(c3ccccc3)c3ccccc3-4)c3cccc4c3-c3ccccc3C43c4ccccc4Oc4ccccc43)cc2)cc1]

97
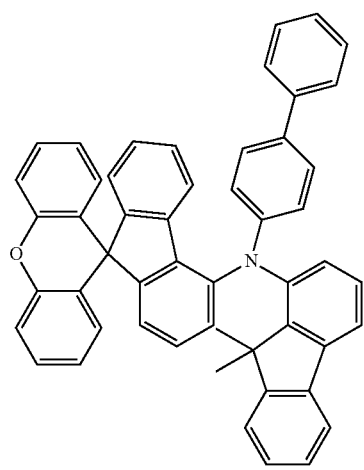 [SMILES: CC1(C)c2ccccc2-c2cccc(N(c3ccc(-c4ccccc4)cc3)c3cccc4c3-c3ccccc3C43c4ccccc4Oc4ccccc43)c21]
98
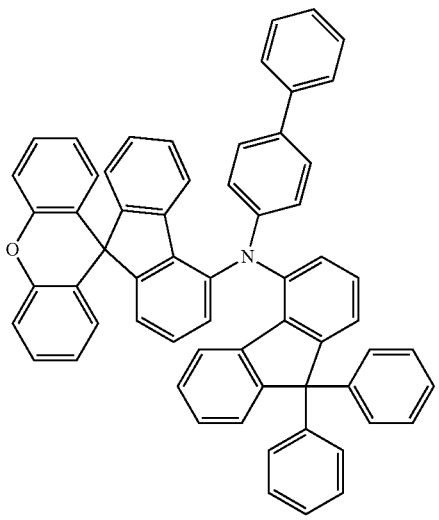 [SMILES: c1ccc(-c2ccc(N(c3cccc4c3-c3ccccc3C4(c3ccccc3)c3ccccc3)c3cccc4c3-c3ccccc3C43c4ccccc4Oc4ccccc43)cc2)cc1]
99
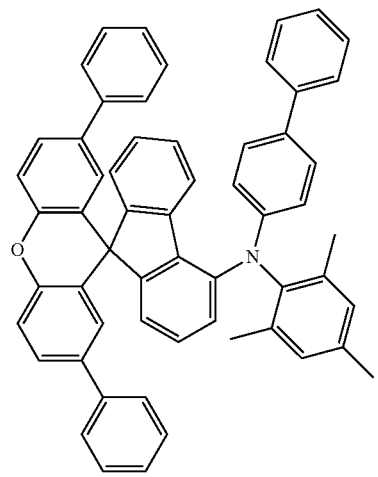 [SMILES: Cc1cc(C)c(N(c2ccc(-c3ccccc3)cc2)c2cccc3c2-c2ccccc2C32c3cc(-c4ccccc4)ccc3Oc3ccc(-c4ccccc4)cc32)c(C)c1]

-continued
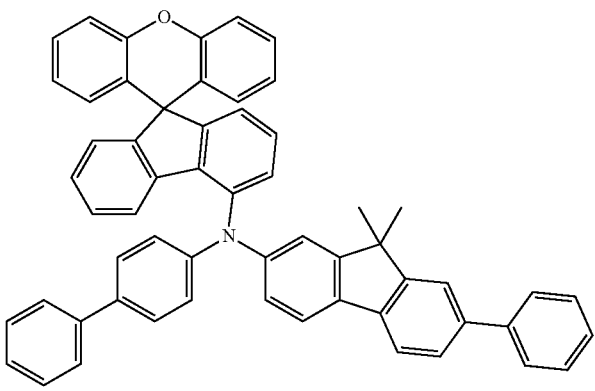 [SMILES: CC1(C)c2cc(-c3ccccc3)ccc2-c2ccc(N(c3ccc(-c4ccccc4)cc3)c3cccc4c3-c3ccccc3C43c4ccccc4Oc4ccccc43)cc21]
100
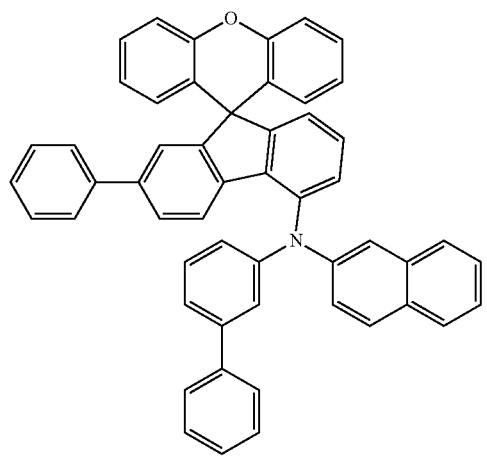 [SMILES: c1ccc(-c2cccc(N(c3ccc4ccccc4c3)c3cccc4c3-c3ccc(-c5ccccc5)cc3C43c4ccccc4Oc4ccccc43)c2)cc1]
101
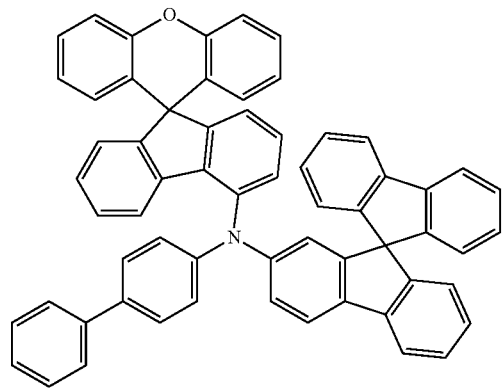 [SMILES: c1ccc(-c2ccc(N(c3ccc4c(c3)C3(c5ccccc5-c5ccccc53)c3ccccc3-4)c3cccc4c3-c3ccccc3C43c4ccccc4Oc4ccccc43)cc2)cc1]
102
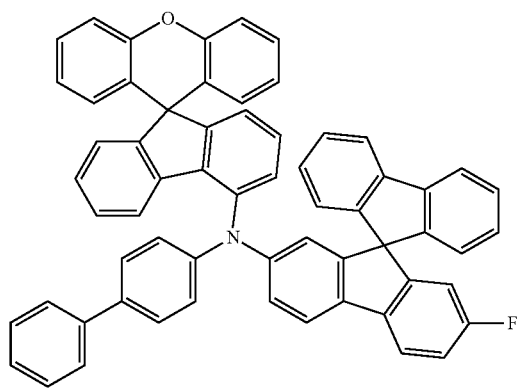 [SMILES: Fc1ccc2c(c1)C1(c3ccccc3-c3ccccc31)c1cc(N(c3ccc(-c4ccccc4)cc3)c3cccc4c3-c3ccccc3C43c4ccccc4Oc4ccccc43)ccc1-2]
103

104
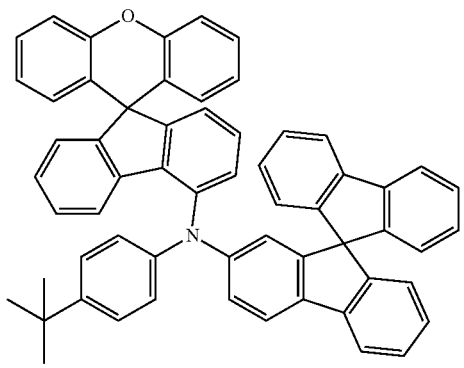 [SMILES: CC(C)(C)c1ccc(N(c2ccc3c(c2)C2(c4ccccc4-c4ccccc42)c2ccccc2-3)c2cccc3c2-c2ccccc2C32c3ccccc3Oc3ccccc32)cc1]
105
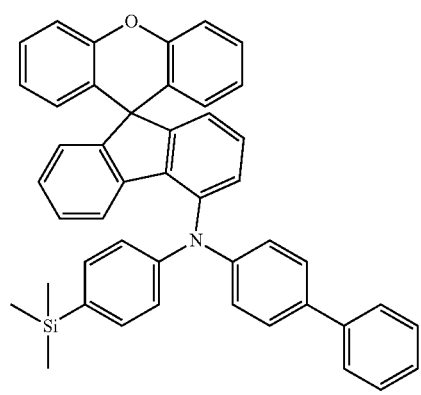 [SMILES: C[Si](C)(C)c1ccc(N(c2ccc(-c3ccccc3)cc2)c2cccc3c2-c2ccccc2C32c3ccccc3Oc3ccccc32)cc1]
106
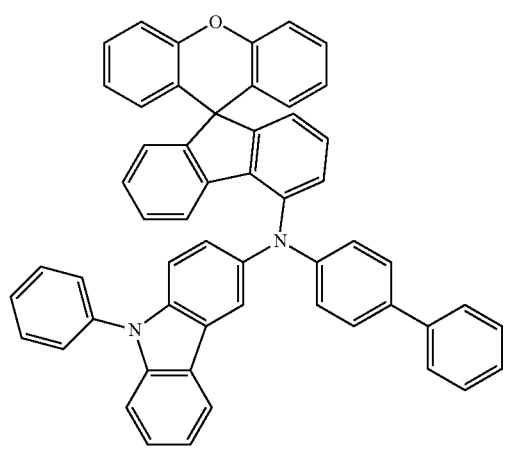 [SMILES: c1ccc(-c2ccc(N(c3ccc4c(c3)c3ccccc3n4-c3ccccc3)c3cccc4c3-c3ccccc3C43c4ccccc4Oc4ccccc43)cc2)cc1]

-continued
107
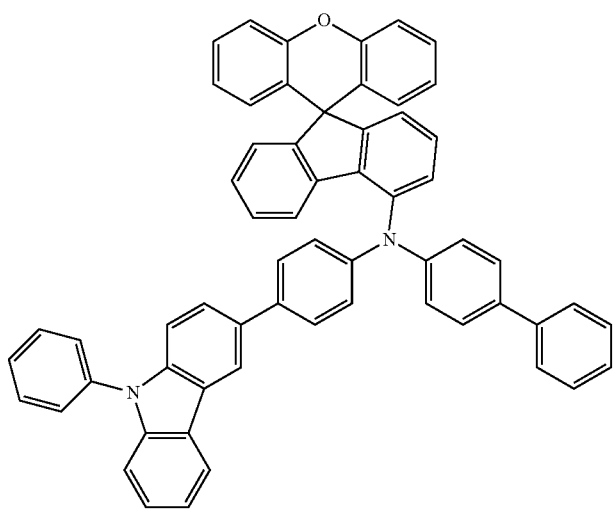 [SMILES: c1ccc(-c2ccc(N(c3ccc(-c4ccc5c(c4)c4ccccc4n5-c4ccccc4)cc3)c3cccc4c3-c3ccccc3C43c4ccccc4Oc4ccccc43)cc2)cc1]
108
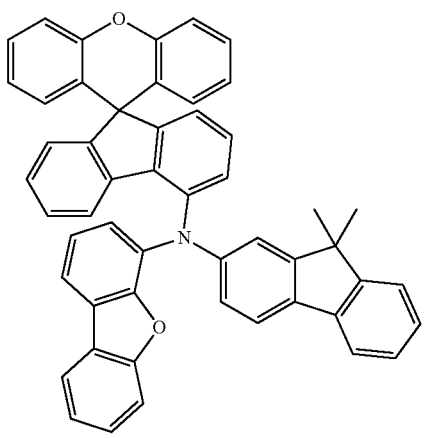 [SMILES: CC1(C)c2ccccc2-c2ccc(N(c3cccc4c3-c3ccccc3C43c4ccccc4Oc4ccccc43)c3cccc4c3oc3ccccc34)cc21]
109
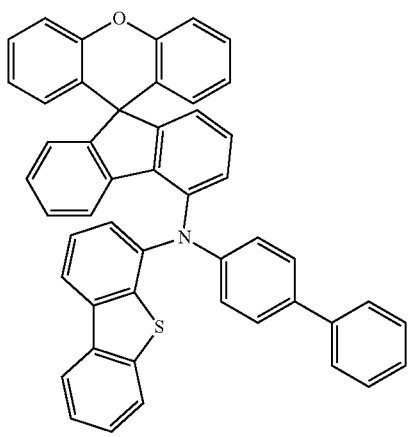 [SMILES: c1ccc(-c2ccc(N(c3cccc4c3-c3ccccc3C43c4ccccc4Oc4ccccc43)c3cccc4c3sc3ccccc34)cc2)cc1]

-continued
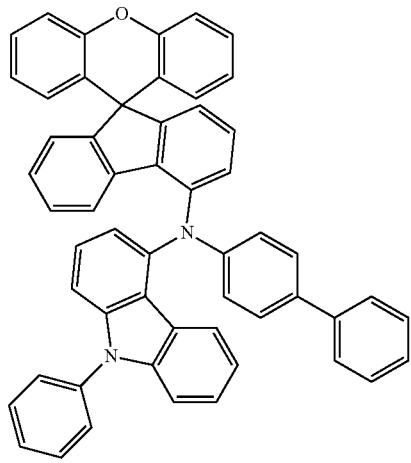 [SMILES: c1ccc(-c2ccc(N(c3cccc4c3-c3ccccc3C43c4ccccc4Oc4ccccc43)c3cccc4c3c3ccccc3n4-c3ccccc3)cc2)cc1]
110
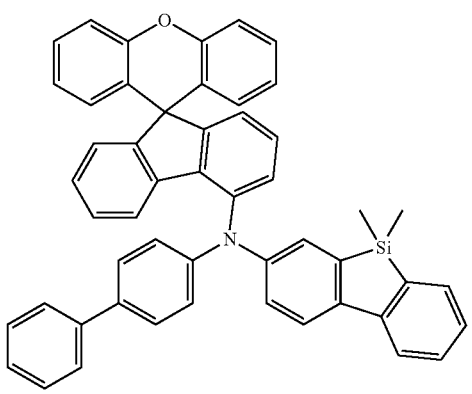 [SMILES: C[Si]1(C)c2ccccc2-c2ccc(N(c3ccc(-c4ccccc4)cc3)c3cccc4c3-c3ccccc3C43c4ccccc4Oc4ccccc43)cc21]
111
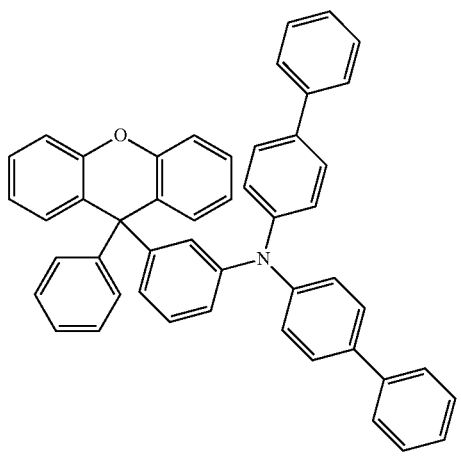 [SMILES: c1ccc(-c2ccc(N(c3ccc(-c4ccccc4)cc3)c3cccc(C4(c5ccccc5)c5ccccc5Oc5ccccc54)c3)cc2)cc1]
112
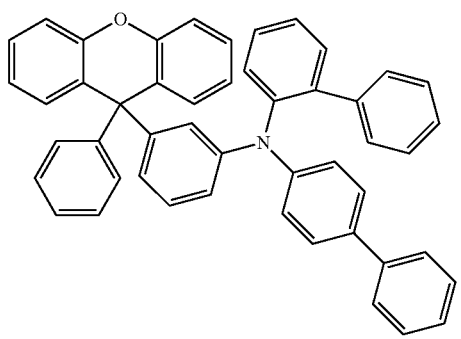 [SMILES: c1ccc(-c2ccc(N(c3cccc(C4(c5ccccc5)c5ccccc5Oc5ccccc54)c3)c3ccccc3-c3ccccc3)cc2)cc1]
113

114
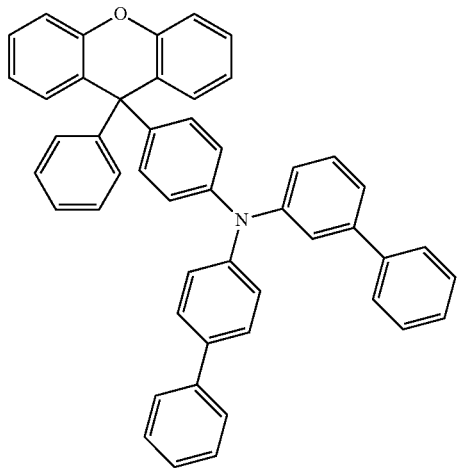 [SMILES: c1ccc(-c2ccc(N(c3ccc(C4(c5ccccc5)c5ccccc5Oc5ccccc54)cc3)c3cccc(-c4ccccc4)c3)cc2)cc1]
115
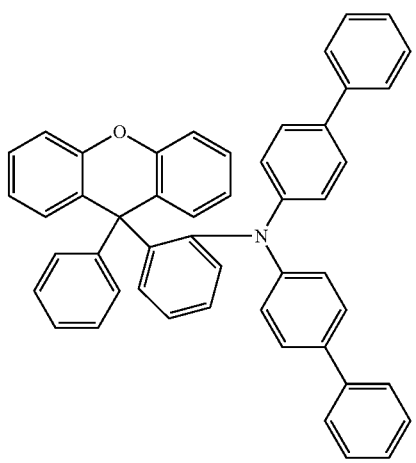 [SMILES: c1ccc(-c2ccc(N(c3ccc(-c4ccccc4)cc3)c3ccccc3C3(c4ccccc4)c4ccccc4Oc4ccccc43)cc2)cc1]
116
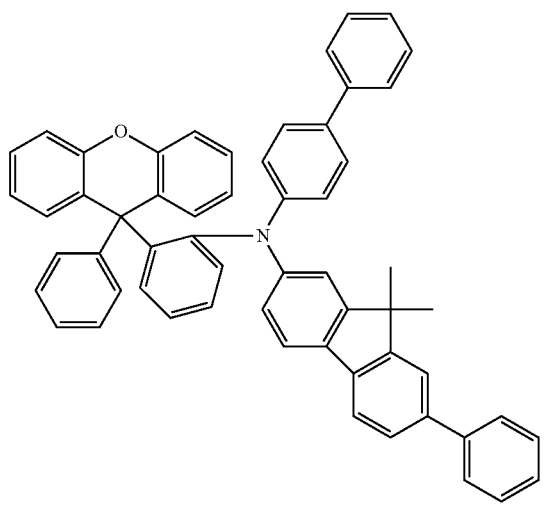 [SMILES: CC1(C)c2cc(-c3ccccc3)ccc2-c2ccc(N(c3ccc(-c4ccccc4)cc3)c3ccccc3C3(c4ccccc4)c4ccccc4Oc4ccccc43)cc21]

117
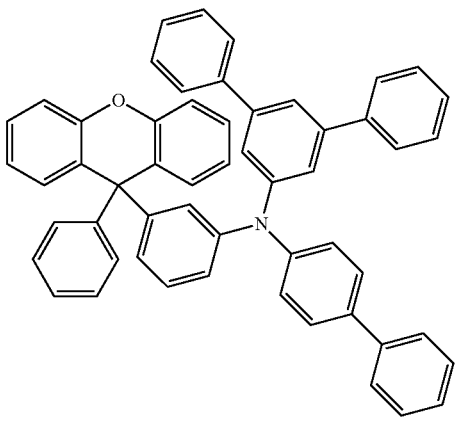 [SMILES: c1ccc(-c2ccc(N(c3cc(-c4ccccc4)cc(-c4ccccc4)c3)c3cccc(C4(c5ccccc5)c5ccccc5Oc5ccccc54)c3)cc2)cc1]
118
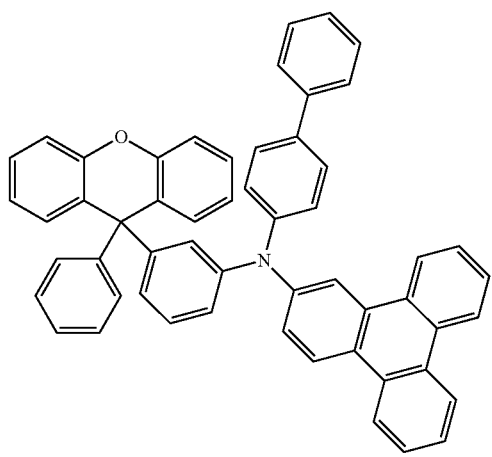 [SMILES: c1ccc(-c2ccc(N(c3cccc(C4(c5ccccc5)c5ccccc5Oc5ccccc54)c3)c3ccc4c5ccccc5c5ccccc5c4c3)cc2)cc1]
119
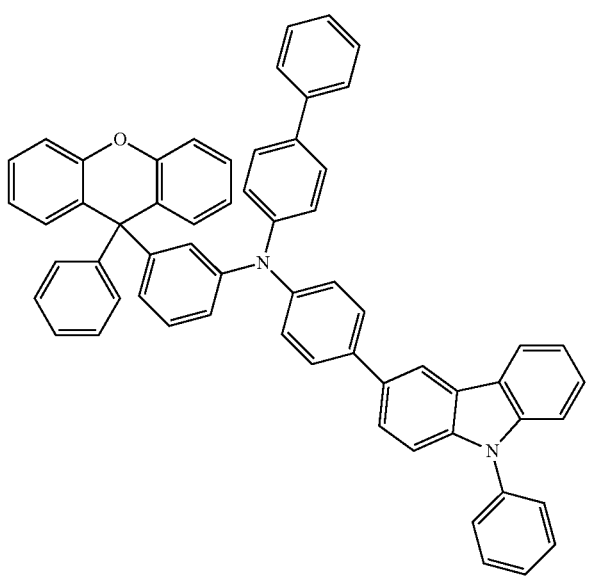 [SMILES: c1ccc(-c2ccc(N(c3ccc(-c4ccc5c(c4)c4ccccc4n5-c4ccccc4)cc3)c3cccc(C4(c5ccccc5)c5ccccc5Oc5ccccc54)c3)cc2)cc1]

-continued
120
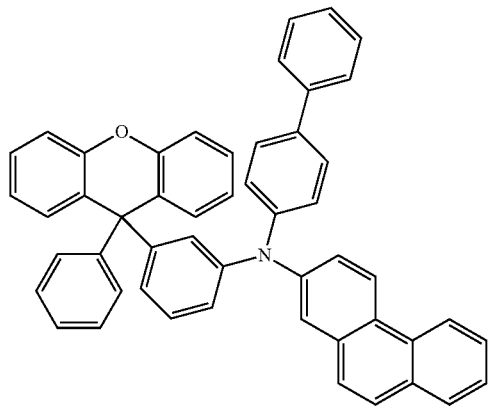 [SMILES: c1ccc(-c2ccc(N(c3cccc(C4(c5ccccc5)c5ccccc5Oc5ccccc54)c3)c3ccc4c(ccc5ccccc54)c3)cc2)cc1]
121
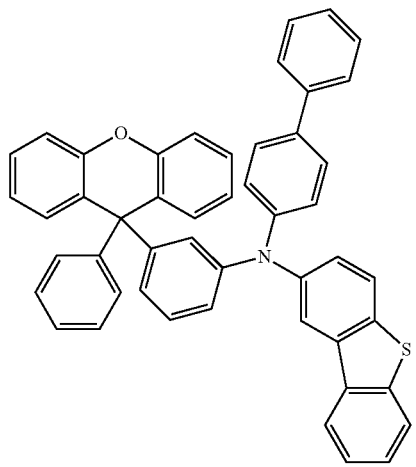 [SMILES: c1ccc(-c2ccc(N(c3cccc(C4(c5ccccc5)c5ccccc5Oc5ccccc54)c3)c3ccc4sc5ccccc5c4c3)cc2)cc1]
122
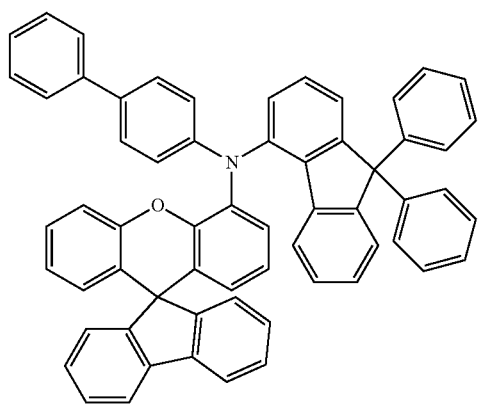 [SMILES: c1ccc(-c2ccc(N(c3cccc4c3Oc3ccccc3C43c4ccccc4-c4ccccc43)c3cccc4c3-c3ccccc3C4(c3ccccc3)c3ccccc3)cc2)cc1]

123
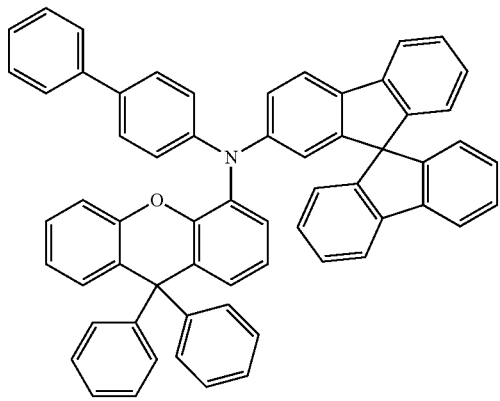 [SMILES: c1ccc(-c2ccc(N(c3ccc4c(c3)C3(c5ccccc5-c5ccccc53)c3ccccc3-4)c3cccc4c3Oc3ccccc3C4(c3ccccc3)c3ccccc3)cc2)cc1]
124
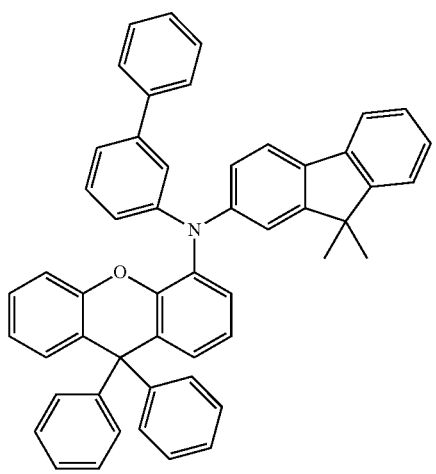 [SMILES: CC1(C)c2ccccc2-c2ccc(N(c3cccc(-c4ccccc4)c3)c3cccc4c3Oc3ccccc3C4(c3ccccc3)c3ccccc3)cc21]
125
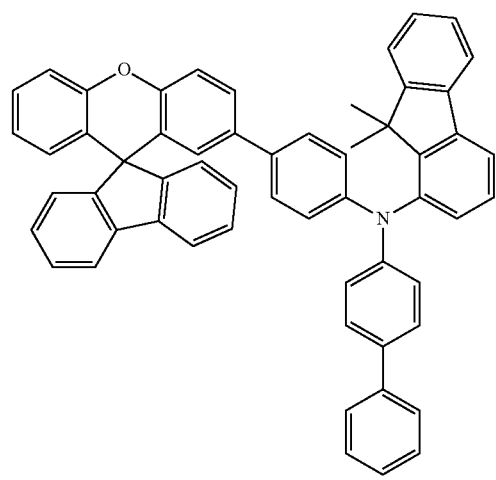 [SMILES: CC1(C)c2ccccc2-c2cccc(N(c3ccc(-c4ccccc4)cc3)c3ccc(-c4ccc5c(c4)C4(c6ccccc6O5)c5ccccc5-c5ccccc54)cc3)c21]

126
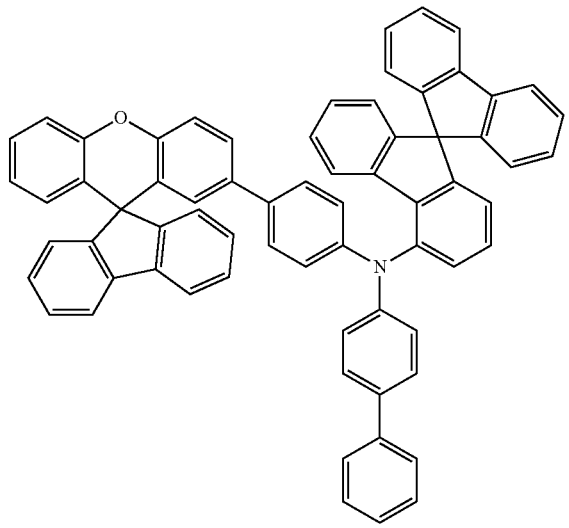 [SMILES: c1ccc(-c2ccc(N(c3ccc(-c4ccc5c(c4)C4(c6ccccc6O5)c5ccccc5-c5ccccc54)cc3)c3cccc4c3-c3ccccc3C43c4ccccc4-c4ccccc43)cc2)cc1]
127
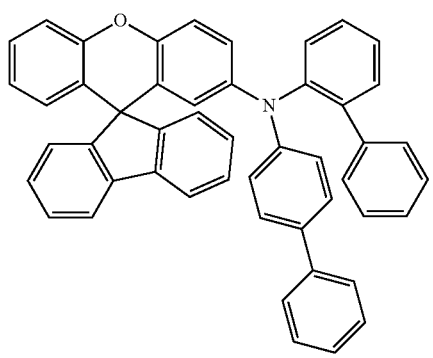 [SMILES: c1ccc(-c2ccc(N(c3ccc4c(c3)C3(c5ccccc5O4)c4ccccc4-c4ccccc43)c3ccccc3-c3ccccc3)cc2)cc1]
128
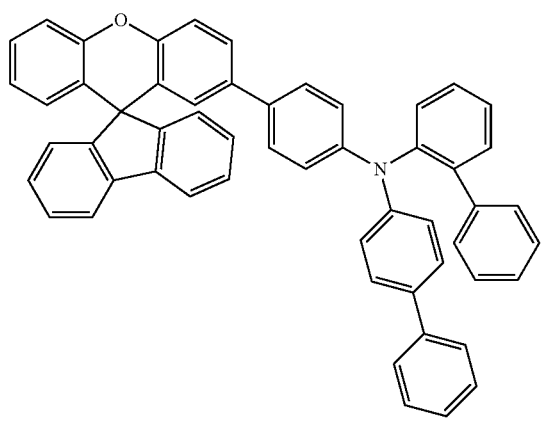 [SMILES: c1ccc(-c2ccc(N(c3ccc(-c4ccc5c(c4)C4(c6ccccc6O5)c5ccccc5-c5ccccc54)cc3)c3ccccc3-c3ccccc3)cc2)cc1]

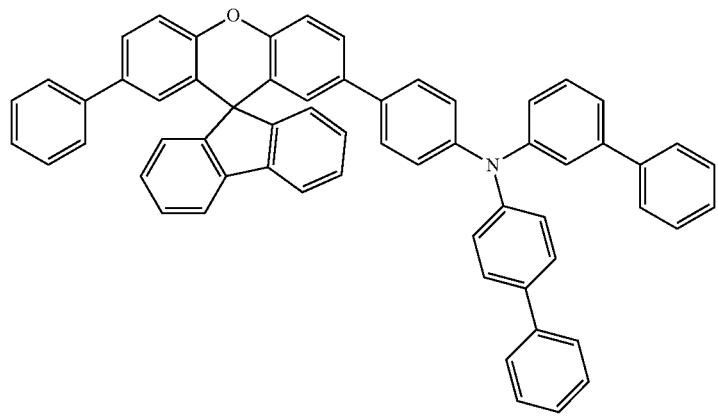 [SMILES: c1ccc(-c2ccc(N(c3ccc(-c4ccc5c(c4)C4(c6cc(-c7ccccc7)ccc6O5)c5ccccc5-c5ccccc54)cc3)c3cccc(-c4ccccc4)c3)cc2)cc1]
129
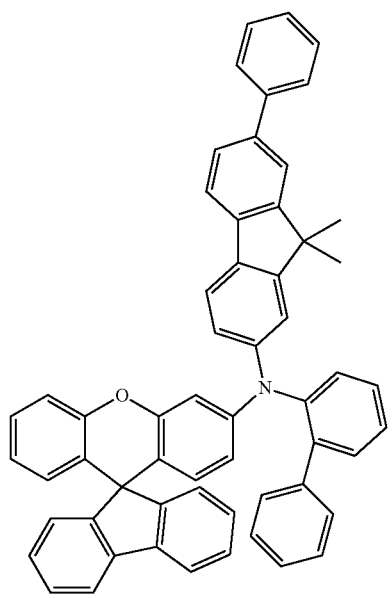 [SMILES: CC1(C)c2cc(-c3ccccc3)ccc2-c2ccc(N(c3ccc4c(c3)Oc3ccccc3C43c4ccccc4-c4ccccc43)c3ccccc3-c3ccccc3)cc21]
130
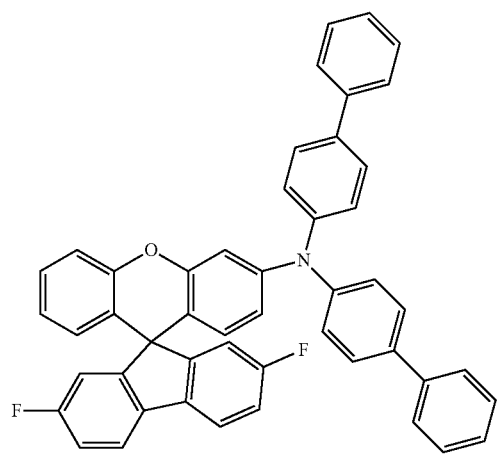 [SMILES: Fc1ccc2c(c1)C1(c3ccccc3Oc3cc(N(c4ccc(-c5ccccc5)cc4)c4ccc(-c5ccccc5)cc4)ccc31)c1cc(F)ccc1-2]
131

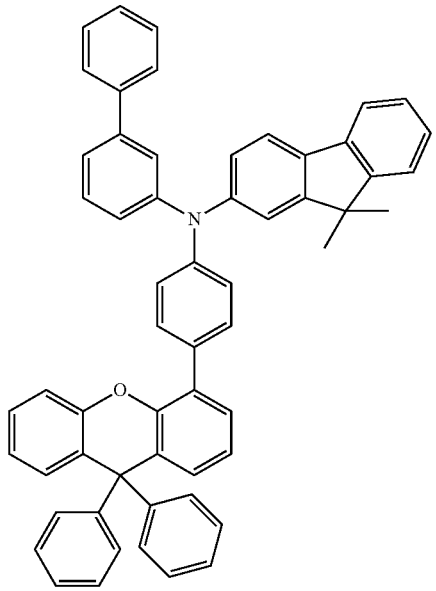 [SMILES: CC1(C)c2ccccc2-c2ccc(N(c3ccc(-c4cccc5c4Oc4ccccc4C5(c4ccccc4)c4ccccc4)cc3)c3cccc(-c4ccccc4)c3)cc21]

132

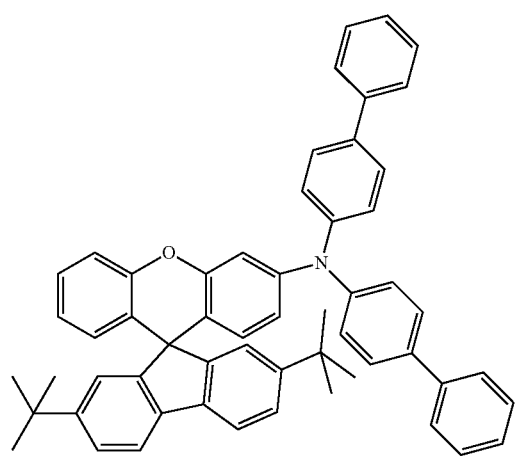 [SMILES: CC(C)(C)c1ccc2c(c1)C1(c3ccccc3Oc3cc(N(c4ccc(-c5ccccc5)cc4)c4ccc(-c5ccccc5)cc4)ccc31)c1cc(C(C)(C)C)ccc1-2]

133

The compounds according to the invention can be synthesised by processes and reaction types known from the prior art, for example halogenation, organometallic addition reaction, Buchwald coupling and Suzuki coupling.

Schemes 1 to 3 show possible synthetic routes for the preparation of the compounds according to the invention. They serve to explain the invention to the person skilled in the art and should not be regarded as restrictive. The person skilled in the art will be able to modify the synthetic routes shown within the bounds of his general expert knowledge or develop completely different routes if this appears more advantageous.

Scheme 1 shows a preferred synthetic route for the preparation of compounds according to the invention which have a diarylxanthene basic structure (index i=0 in formula (I)).

The metallation of a 2-halogen-substituted diaryl ether (A) using reactive metals (for example magnesium by the Grignard method) or using organolithium compounds and subsequent addition onto monohalogenated benzophenone (B) and subsequent acid-catalysed cyclisation of the intermediate alcoholate results in the corresponding halogen-substituted xanthenes (C). The halides (C) formed in this way can subsequently be converted further into compounds D and E according to the invention by methods which are familiar to the person skilled in the art (C—C coupling, such as Suzuki, Negishi, Yamamoto, Grignard-Cross, Stille, Heck coupling, etc.; C—N coupling, such as Buchwald or Ullmann coupling).

Scheme 1

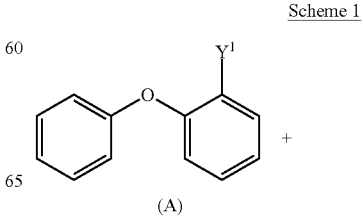

(A)

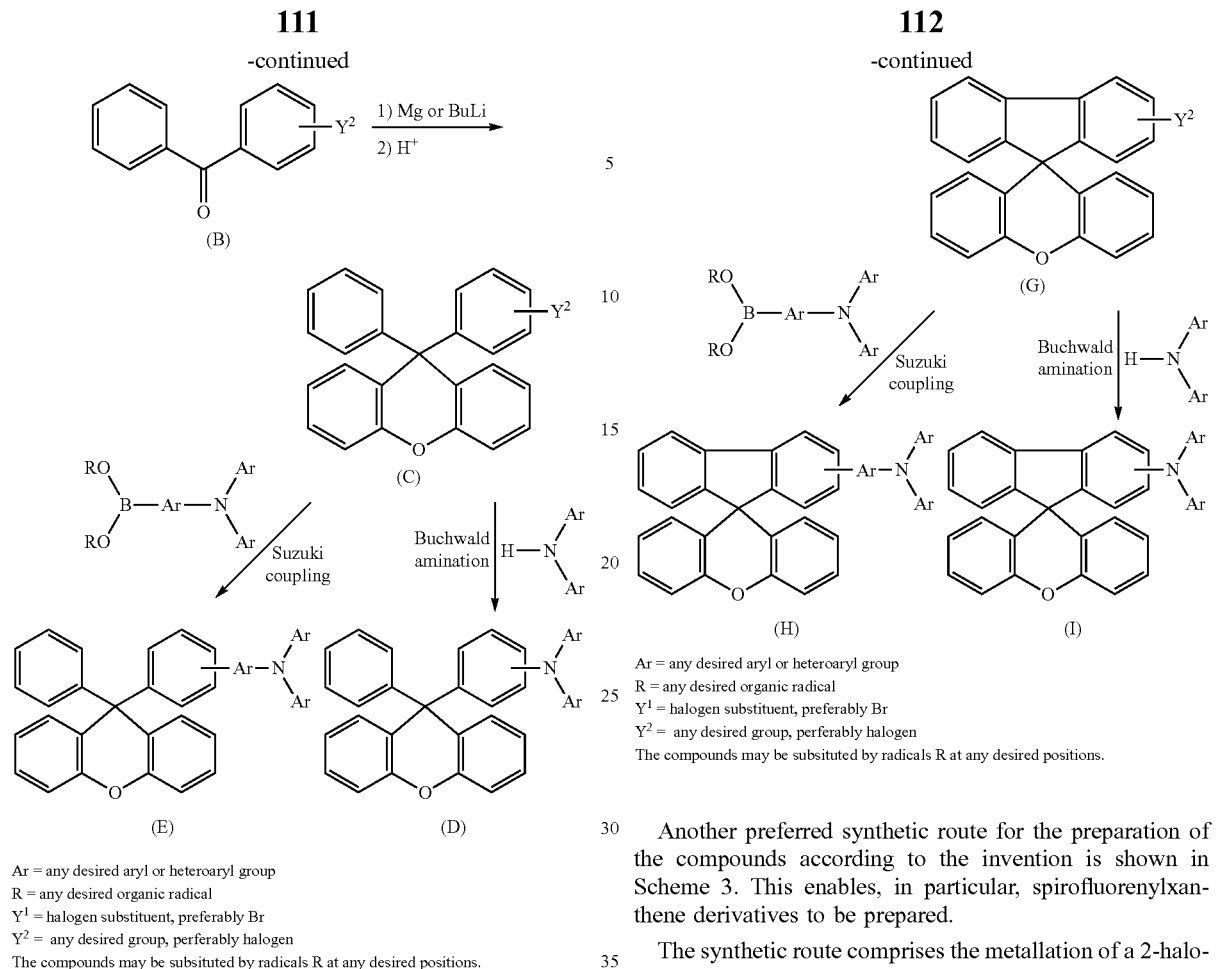

Ar = any desired aryl or heteroaryl group
R = any desired organic radical
Y¹ = halogen substituent, preferably Br
Y² = any desired group, perferably halogen
The compounds may be subsituted by radicals R at any desired positions.

Scheme 2 shows how the corresponding spirobifluorenyixanthene compounds (compounds H and I) can be prepared analogously to the diarylxanthenes shown in Scheme 1. To this end, a fluorenone derivative (compound F) is employed instead of the benzophenone derivative in the first step, the addition onto the carbonyl compound and cyclisation.

Another preferred synthetic route for the preparation of the compounds according to the invention is shown in Scheme 3. This enables, in particular, spirofluorenylxanthene derivatives to be prepared.

The synthetic route comprises the metallation of a 2-halogen-substituted diaryl compound (K) using reactive metals (for example magnesium by the Grignard method) or using organolithium compounds. An addition onto monohalogenated xanthenone (J) and an acid-catalysed cyclisation of the intermediate alcoholate are subsequently carried out. The corresponding halogen-substituted spirofluorenylxanthenes (L) are thus obtained.

The halides (L) formed in this way can subsequently be converted further into compounds (M) and (N) according to the invention by methods which are familiar to the person skilled in the art (C—C coupling, such as Suzuki, Negishi, Yamamoto, Grignard-Cross, Stille, Heck coupling, etc.; C—N coupling, such as Buchwald or Ullmann coupling).

Scheme 2

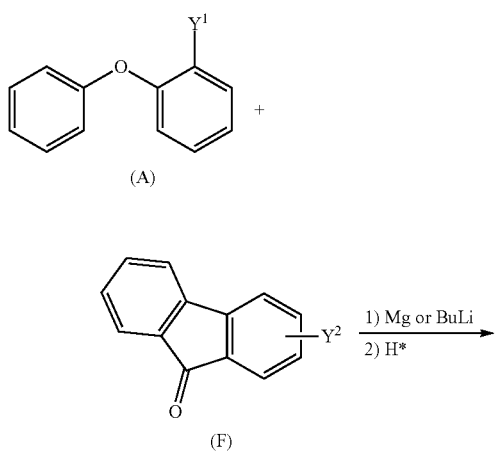

Scheme 3

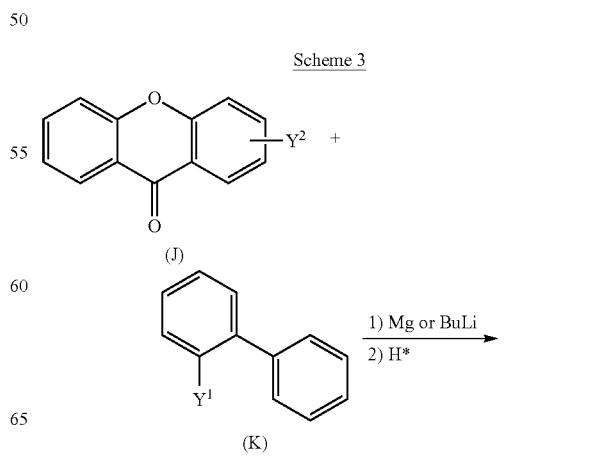

-continued

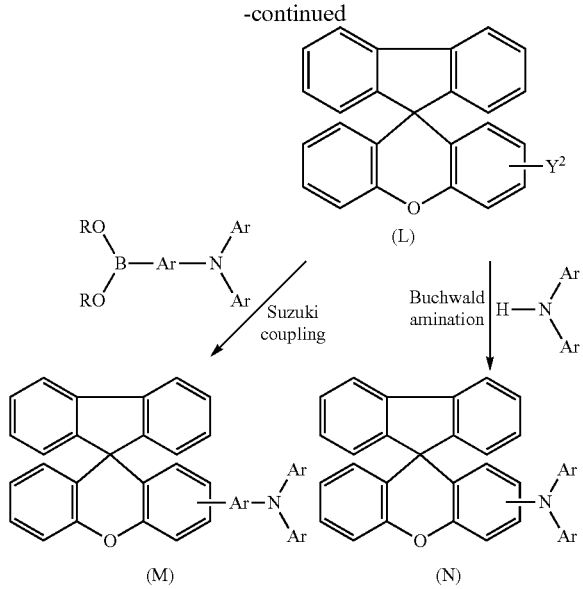

Ar = any desired aryl or heteroaryl group
R = any desired organic radical
$Y^1$ = halogen substituent, preferably Br
$Y^2$ = any desired group, perferably halogen
The compounds may be subsituted by radicals R at any desired positions.

Synthetic routes for the starting compounds (for example (A), (B), (F) and (K)) which are employed in the synthesis of the compounds according to the invention are known to the person skilled in the art. The coupling reactions here are preferably Buchwald couplings and Suzuki couplings.

The compounds obtained can optionally be reacted further and functionalised after the synthetic steps shown above if this is necessary in order to obtain the desired compounds according to the invention.

The invention thus furthermore relates to a process for the preparation of a compound of the formula (I), characterised in that the basic structure is prepared by addition of an organometallic nucleophile onto a carbonyl group.

The carbonyl group here is preferably a diarylcarbonyl group. The organometallic nucleophile here is preferably a diaryl ether or a diaryl thioether, particularly preferably a diaryl ether.

The arylamino group is preferably introduced in a further step by a coupling reaction, particularly preferably Buchwald coupling or Suzuki coupling.

Synthetic processes described in detail, in which, inter alia, precise reaction conditions are indicated, are shown in the working examples. They supplement the general processes indicated above through specific examples.

The compounds described above, in particular compounds which are substituted by reactive leaving groups, such as bromine, iodine, chlorine, boronic acid or boronic acid ester, can be used as monomers for the production of corresponding oligomers, dendrimers or polymers. Suitable reactive leaving groups are, for example, bromine, iodine, chlorine, boronic acids, boronic acid esters, amines, alkenyl or alkynyl groups having a terminal C—C double bond or C—C triple bond, oxiranes, oxetanes, groups which undergo a cycloaddition, for example a 1,3-dipolar cycloaddition, such as, for example, dienes or azides, carboxylic acid derivatives, alcohols and silanes.

The invention therefore furthermore relates to oligomers, polymers or dendrimers containing one or more compounds of the formula (I), where the bond(s) to the polymer, oligomer or dendrimer may be localised at any desired positions in formula (I) which are substituted by $R^1$ or $R^2$. Depending on the linking of the compound of the formula (I) the compound is a constituent of a side chain of the oligomer or polymer or a constituent of the main chain. An oligomer in the sense of this invention is taken to mean a compound which is built up from at least three monomer units. A polymer in the sense of the invention is taken to mean a compound which is built up from at least ten monomer units. The polymers, oligomers or dendrimers according to the invention may be conjugated, partially conjugated or non-conjugated. The oligomers or polymers according to the invention may be linear, branched or dendritic. In the structures linked in a linear manner, the units of the formula (I) may be linked directly to one another or they may be linked to one another via a divalent group, for example via a substituted or unsubstituted alkylene group, via a heteroatom or via a divalent aromatic or heteroaromatic group. In branched and dendritic structures, for example, three or more units of the formula (I) may be linked via a trivalent or polyvalent group, for example via a trivalent or polyvalent aromatic or heteroaromatic group, to form a branched or dendritic oligomer or polymer.

The same preferences as described above for compounds of the formula (I) apply to the recurring units of the formula (I) in oligomers, dendrimers and polymers.

For the preparation of the oligomers or polymers, the monomers according to the invention are homopolymerised or copolymerised with further monomers. Suitable and preferred comonomers are selected from fluorenes (for example in accordance with EP 842208 or WO 2000/22026), spirobifluorenes (for example in accordance with EP 707020, EP 894107 or WO 2006/061181), para-phenylenes (for example in accordance with WO 1992/18552), carbazoles (for example in accordance with WO 2004/070772 or WO 2004/113468), thiophenes (for example in accordance with EP 1028136), dihydrophenanthrenes (for example in accordance with WO 2005/014689 or WO 2007/006383), cis- and trans-indenofluorenes (for example in accordance with WO 2004/041901 or WO 2004/113412), ketones (for example in accordance with WO 2005/040302), phenanthrenes (for example in accordance with WO 2005/104264 or WO 2007/017066) or also a plurality of these units. The polymers, oligomers and dendrimers usually also contain further units, for example emitting (fluorescent or phosphorescent) units, such as, for example, vinyltriarylamines (for example in accordance with WO 2007/068325) or phosphorescent metal complexes (for example in accordance with WO 2006/003000), and/or charge-transport units, in particular those based on triarylamines.

The polymers, oligomers and dendrimers according to the invention have advantageous properties, in particular long lifetimes, high efficiencies and good colour coordinates.

The polymers and oligomers according to the invention are generally prepared by polymerisation of one or more types of monomer, at least one monomer of which results in recurring units of the formula ((I) in the polymer. Suitable polymerisation reactions are known to the person skilled in the art and are described in the literature. Particularly suitable and preferred polymerisation reactions which result in C—C or C—N links are the following:

(A) SUZUKI polymerisation;
(B) YAMAMOTO polymerisation;
(C) STILLE polymerisation; and
(D) HARTWIG-BUCHWALD polymerisation.

The way in which the polymerisation can be carried out by these methods and the way in which the polymers can then be separated off from the reaction medium and purified is known to the person skilled in the art and is described in detail in the literature, for example in WO 2003/048225, WO 2004/037887 and WO 2004/037887.

For the processing of the compounds according to the invention from the liquid phase, for example by spin coating or by printing processes, formulations of the compounds according to the invention are necessary. These formulations can be, for example, solutions, dispersions or emulsions. It may be preferred to use mixtures of two or more solvents for this purpose. Suitable and preferred solvents are, for example, toluene, anisole, o-, m- or p-xylene, methyl benzoate, mesitylene, tetralin, veratrol, THF, methyl-THF, THP, chlorobenzene, dioxane, phenoxytoluene, in particular 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecyl-benzene, ethyl benzoate, indane, methyl benzoate, NMP, p-cymene, phenetol, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane or mixtures of these solvents.

The invention therefore furthermore relates to a formulation, in particular a solution, dispersion or emulsion, comprising at least one compound of the formula (I) or at least one polymer, oligomer or dendrimer containing at least one unit of the formula (I), and at least one solvent, preferably an organic solvent. The way in which solutions of this type can be prepared is known to the person skilled in the art and is described, for example, in WO 2002/072714, WO 2003/019694 and the literature cited therein.

The compounds according to the invention are suitable for use in electronic devices, in particular in organic electroluminescent devices (OLEDs). Depending on the substitution, the compounds are employed in different functions and layers.

The invention therefore furthermore relates to the use of the compound of the formula (I) in an electronic device. The electronic device here is preferably selected from the group consisting of organic integrated circuits (OICs), organic field-effect transistors (OFETs), organic thin-film transistors (OTFTs), organic light-emitting transistors (OLETs), organic solar cells (OSCs), organic optical detectors, organic photoreceptors, organic field-quench devices (OFQDs), organic light-emitting electrochemical cells (OLECs), organic laser diodes (O-lasers) and particularly preferably organic electroluminescent devices (OLEDs).

The invention furthermore relates, as already indicated above, to an electronic device comprising at least one compound of the formula (I). The electronic device here is preferably selected from the devices mentioned above.

It is particularly preferably an organic electroluminescent device (OLED) comprising anode, cathode and at least one emitting layer, characterised in that at least one organic layer, which may be an emitting layer, a hole-transport layer or another layer, comprises at least one compound of the formula (I).

Apart from cathode, anode and the emitting layer, the organic electroluminescent device may also comprise further layers. These are selected, for example, from in each case one or more hole-injection layers, hole-transport layers, hole-blocking layers, electron-transport layers, electron-injection layers, electron-blocking layers, exciton-blocking layers, interlayers, charge-generation layers (IDMC 2003, Taiwan; Session 21 OLED (5), T. Matsumoto, T. Nakada, J. Endo, K. Mori, N. Kawamura, A. Yokoi, J. Kido, *Multiphoton Organic EL Device Having Charge Generation Layer*) and/or organic or in-organic p/n junctions. However, it should be pointed out that each of these layers does not necessarily have to be present and the choice of layers is always dependent on the compounds used and in particular also on whether the electroluminescent device is fluorescent or phosphorescent.

The sequence of the layers of the organic electroluminescent device is preferably the following: anode-hole-injection layer-hole-transport layer-emitting layer-electron-transport layer-electron-injection layer-cathode.

It should again be pointed out here that not all the said layers have to be present, and/or that further layers may additionally be present.

The organic electroluminescent device according to the invention may comprise a plurality of emitting layers. These emission layers in this case particularly preferably have in total a plurality of emission maxima between 380 nm and 750 nm, resulting overall in white emission, i.e. various emitting compounds which are able to fluoresce or phosphoresce and which emit blue or yellow or orange or red light are used in the emitting layers. Particular preference is given to three-layer systems, i.e. systems having three emitting layers, where at least one of these layers preferably comprises at least one compound of the formula (I) and where the three layers exhibit blue, green and orange or red emission (for the basic structure see, for example, WO 2005/011013). The compounds according to the invention may alternatively and/or additionally also be present in the hole-transport layer or in another layer.

It should be noted that, for the generation of white light, an emitter compound used individually which emits in a broad wavelength range may also be suitable instead of a plurality of emitter compounds emitting in colour.

It is preferred in accordance with the invention for the compound of the formula (I) to be employed in an electronic device comprising one or more emitters. The compound may be present in various layers here, preferably in a hole-transport layer, an electron-blocking layer, a hole-injection layer or in an emitting layer.

The term phosphorescent emitters typically encompasses compounds in which the light emission takes place through a spin-forbidden transition, for example a transition from an excited triplet state or a state having a higher spin quantum number, for example a quintet state.

Suitable phosphorescent emitters (=triplet emitters) are, in particular, compounds which emit light, preferably in the visible region, on suitable excitation and in addition contain at least one atom having an atomic number greater than 20, preferably greater than 38 and less than 84, particularly preferably greater than 56 and less than 80. The phosphorescent emitters used are preferably compounds which contain copper, molybdenum, tungsten, rhenium, ruthenium, osmium, rhodium, iridium, palladium, platinum, silver, gold or europium, in particular compounds which contain iridium, platinum or copper.

For the purposes of the present invention, all luminescent iridium, platinum or copper complexes are regarded as phosphorescent compounds.

Examples of the emitters described above are revealed by the applications WO 00/70655, WO 01/41512, WO 02/02714, WO 02/15645, EP 1191613, EP 1191612, EP 1191614, WO 05/033244, WO 05/019373 and US 2005/0258742, In general, all phosphorescent complexes as used in accordance with the prior art for phosphorescent OLEDs and as are known to the person skilled in the art in the area of organic electroluminescent devices are suitable. The person skilled in the art will also be able, without inventive step, to employ further phosphorescent complexes in combination with the compounds of the formula (I) in organic electroluminescent devices.

Explicit examples of suitable phosphorescent emitter compounds can be obtained from a table below containing generally preferred phosphorescent emitters.

However, the compound of the formula (I) can also be employed in accordance with the invention in an electronic device comprising one or more fluorescent emitters.

In a preferred embodiment of the invention, the compounds of the formula (I) are employed as hole-transport material. The compounds are then preferably employed in a hole-transport layer, an electron-blocking layer or a hole-injection layer.

A hole-transport layer in accordance with the present application is a layer having a hole-transporting function which is located between anode and emitting layer.

Hole-injection layers and electron-blocking layers in the sense of the present invention are taken to be specific embodiments of hole-transport layers. In the case of a plurality of hole-transport layers between anode and emitting layer, a hole-injection layer is a hole-transport layer which is directly adjacent to the anode or is only separated therefrom by a single coating of the anode. In the case of a plurality of hole-transport layers between anode and emitting layer, an electron-blocking layer is the hole-transport layer which is directly adjacent to the emitting layer on the anode side.

If the compound of the formula (I) is employed as hole-transport material in a hole-transport layer, a hole-injection layer or an electron-blocking layer, the compound can be employed as pure material, i.e. in a proportion of 100%, in the hole-transport layer, or it can be employed in combination with one or more further compounds. According to a preferred embodiment, the organic layer comprising the compound of the formula (I) then additionally comprises one or more p-dopants. In accordance with the present invention, the p-dopants employed are preferably organic electron-acceptor compounds which are able to oxidise one or more of the other compounds of the mixture.

Particularly preferred embodiments of p-dopants are the compounds disclosed in WO 2011/073149, EP 1968131, EP 2276085, EP 2213662, EP 1722602, EP 2045848, DE 102007031220, U.S. Pat. No. 8,044,390, U.S. Pat. No. 8,057,712, WO 2009/003455, WO 2010/094378, WO 2011/120709, US 2010/0096600 and WO 2012/095143.

In a further preferred embodiment of the invention, the compound of the formula (I) is used as hole-transport material in combination with a hexaazatriphenylene derivative, as described in US 2007/0092755. The hexaazatriphenylene derivative here is particularly preferably employed in a separate layer.

In a further embodiment of the present invention, the compounds of the formula (I) are employed as matrix material in combination with one or more emitters, preferably phosphorescent emitters.

The proportion of the matrix material in the emitting layer is in this case between 50.0 and 99.9% by vol., preferably between 80.0 and 99.5% by vol. and particularly preferably between 92.0 and 99.5% by vol. for fluorescent emitting layers and between 85.0 and 97.0% by vol. for phosphorescent emitting layers.

Correspondingly, the proportion of the emitter is between 0.1 and 50.0% by vol., preferably between 0.5 and 20.0% by vol. and particularly preferably between 0.5 and 8.0% by vol. for fluorescent emitting layers and between 3.0 and 15.0% by vol. for phosphorescent emitting layers.

An emitting layer of an organic electroluminescent device may also comprise systems comprising a plurality of matrix materials (mixed-matrix systems) and/or a plurality of emitters.

In a further preferred embodiment of the invention, the compounds of the formula (I) are used as a component of mixed-matrix systems. The mixed-matrix systems preferably comprise two or three different matrix materials, particularly preferably two different matrix materials. One of the two materials here is preferably a material having hole-transporting properties and the other material is a material having electron-transporting properties. However, the desired electron-transporting and hole-transporting properties of the mixed-matrix components may also be combined principally or completely in a single mixed-matrix components, where the further mixed-matrix component(s) fulfil other functions. The two different matrix materials here may be present in a ratio of 1:50 to 1:1, preferably 1:20 to 1:1, particularly preferably 1:10 to 1:1 and very particularly preferably 1:4 to 1:1. Mixed-matrix systems are preferably employed in phosphorescent organic electroluminescent devices. More precise information on mixed-matrix systems is given, inter alia, in the application WO 2010/108579.

The mixed-matrix systems may comprise one or more emitters, preferably one or more phosphorescent emitters. In general, mixed-matrix systems are preferably employed in phosphorescent organic electroluminescent devices.

Particularly suitable matrix materials which can be used as matrix components of a mixed-matrix system in combination with the compounds according to the invention are selected from the preferred matrix materials for phosphorescent emitters indicated below or the preferred matrix materials for fluorescent emitters, depending on what type of emitter compound is employed in the mixed-matrix system.

Preferred phosphorescent emitters for use in mixed-matrix systems are the phosphorescent emitters shown above and in a following table.

In still a further preferred embodiment of the invention, the compound of the formula (I) is employed as fluorescent emitter in an emitting layer.

If the compound according to the invention is employed as emitting material in an emitting layer, it is preferably employed in combination with one or more matrix materials. Preferred matrix materials for use in combination with the compound of the formula (I) as emitter are indicated in the following sections.

Materials preferably employed in the devices according to the invention are shown below, arranged in accordance with their use and function.

Explicit examples of phosphorescent emitters are shown in the following table.

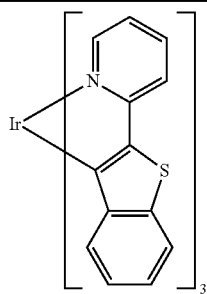
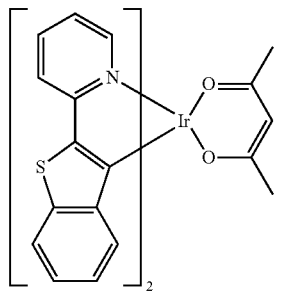
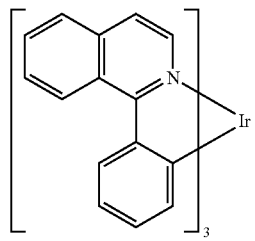
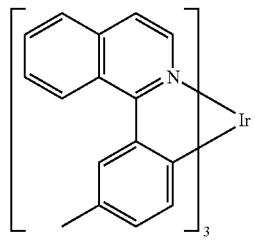
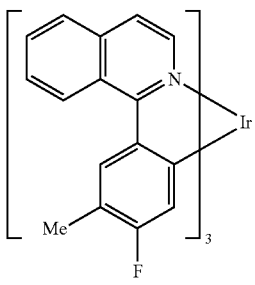
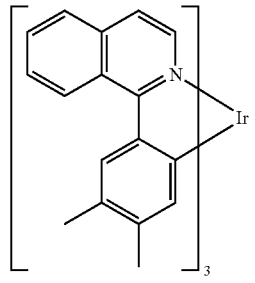
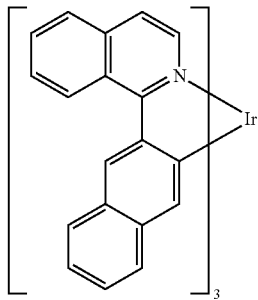
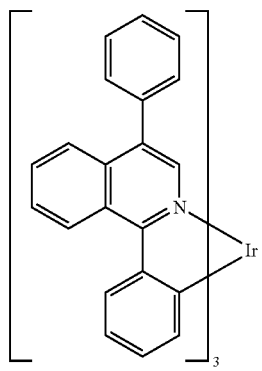
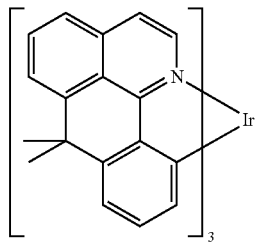
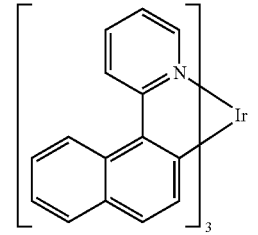
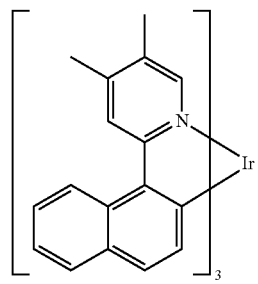

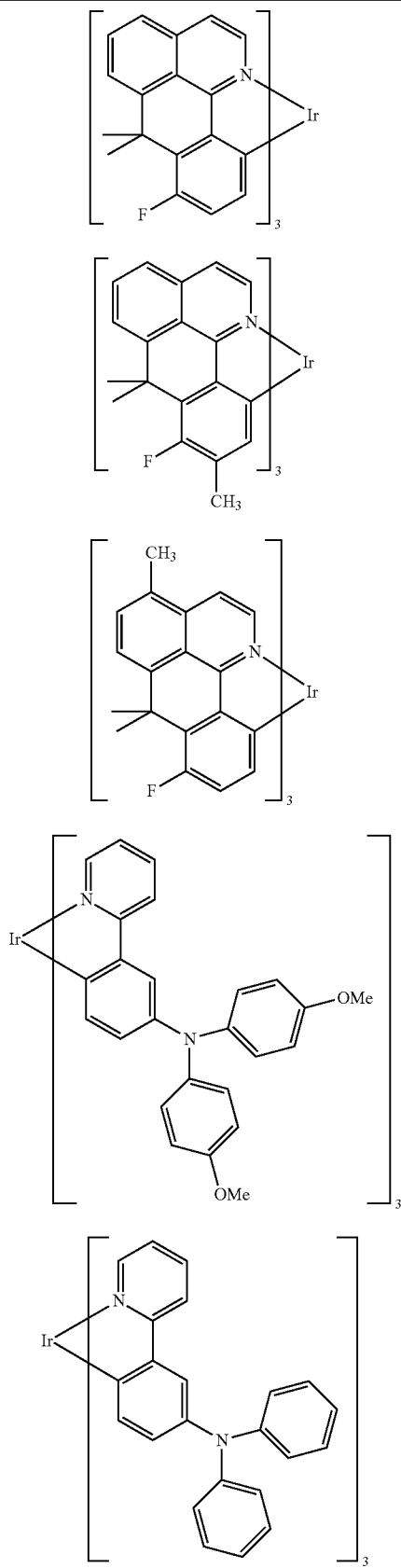
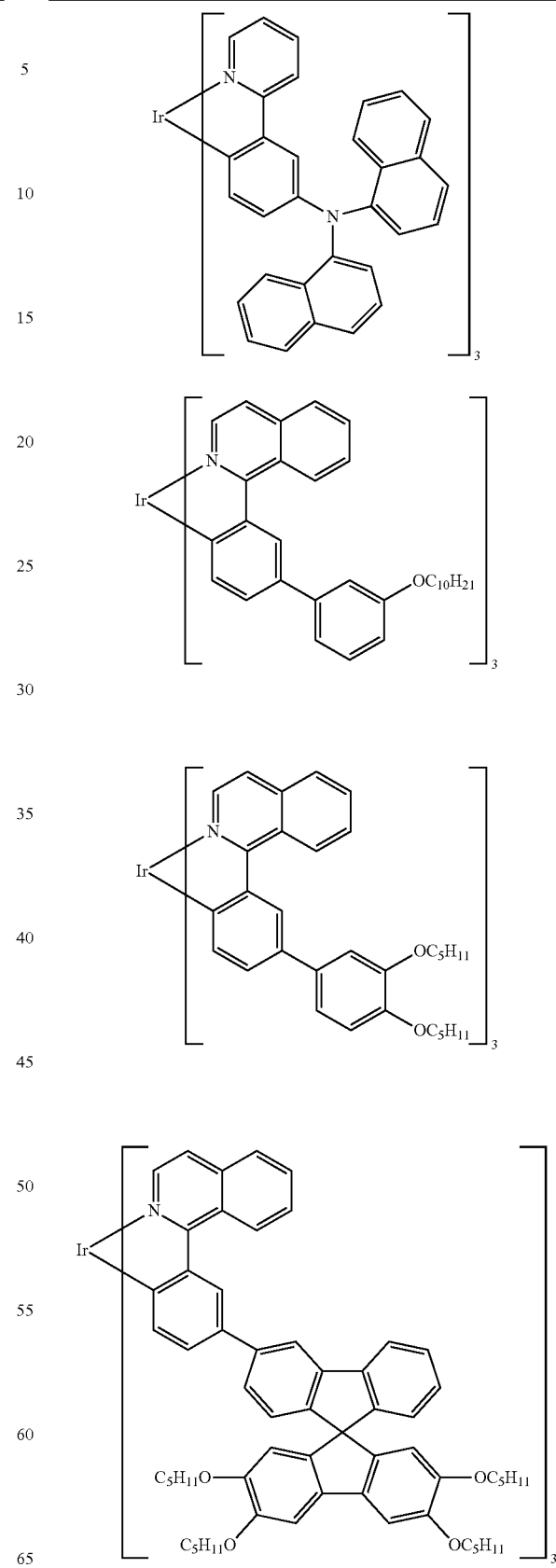

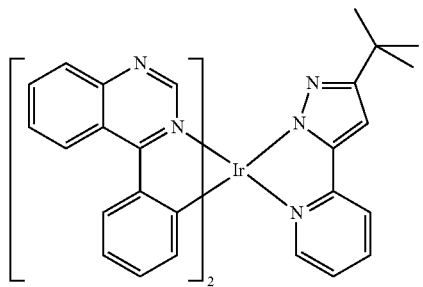
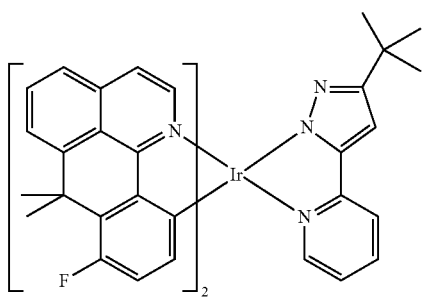
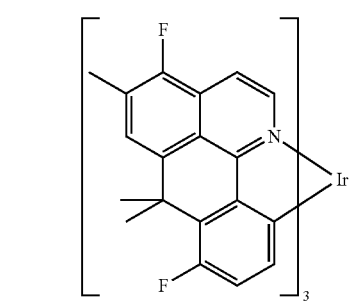
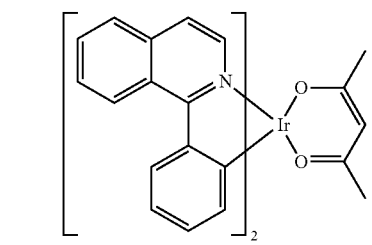
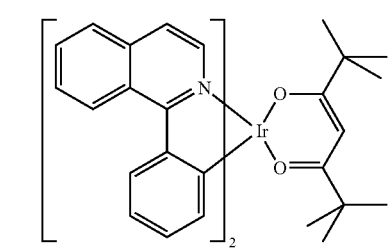
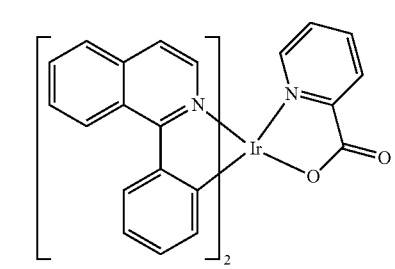
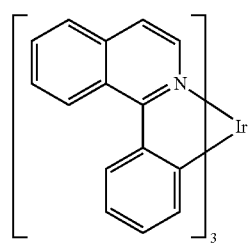
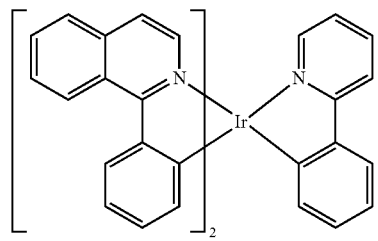
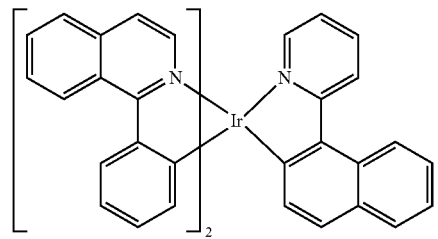
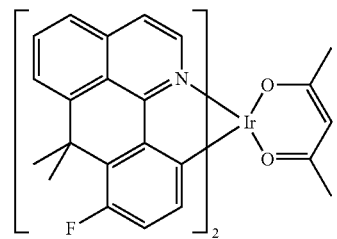
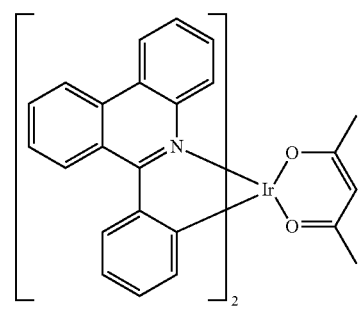
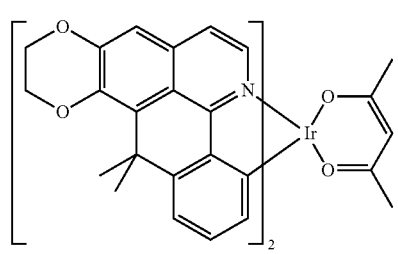

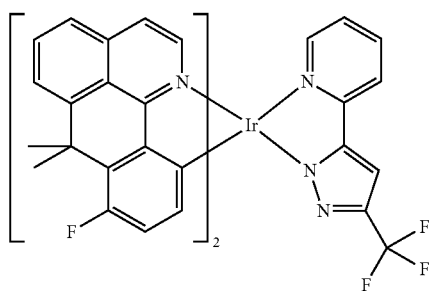
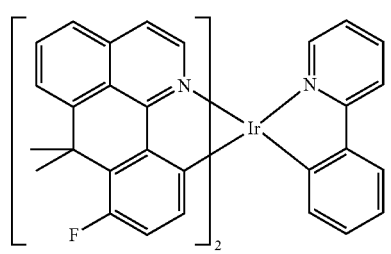
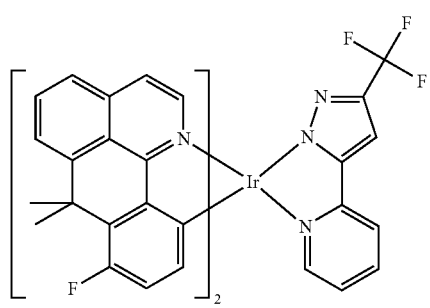
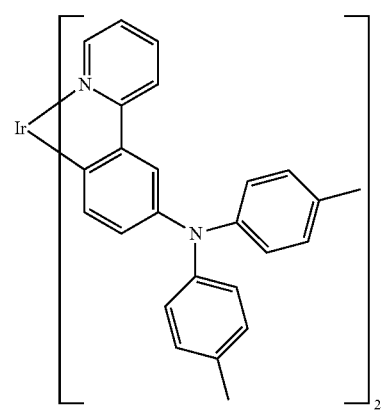
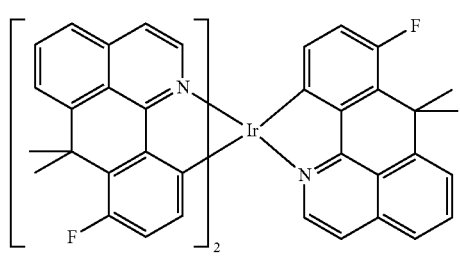
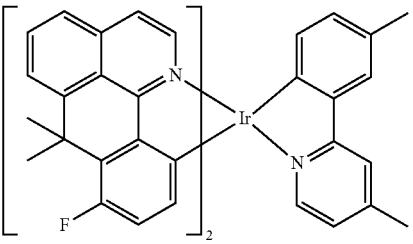
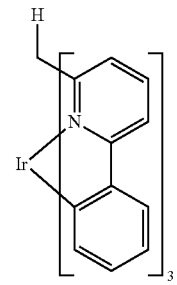
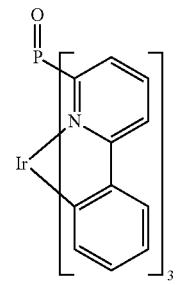
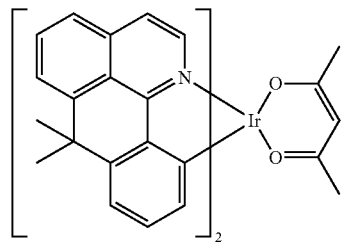
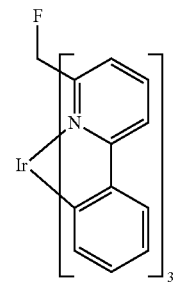
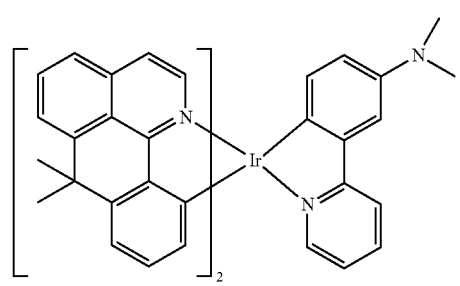

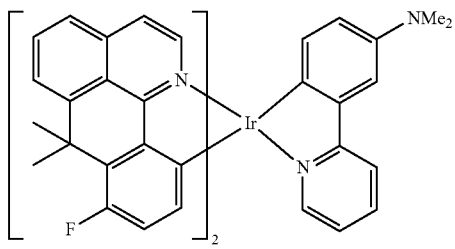
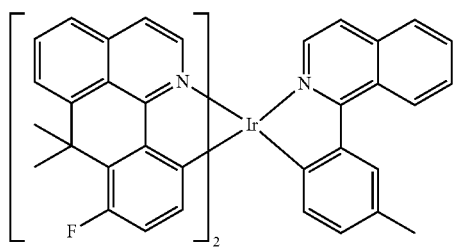
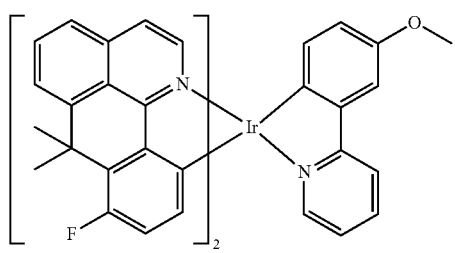
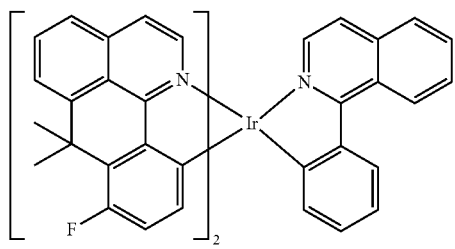
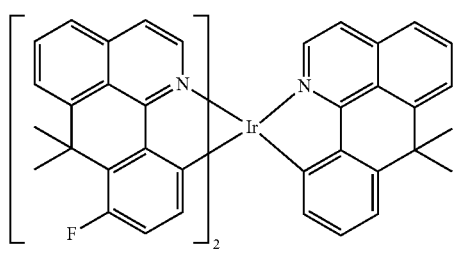
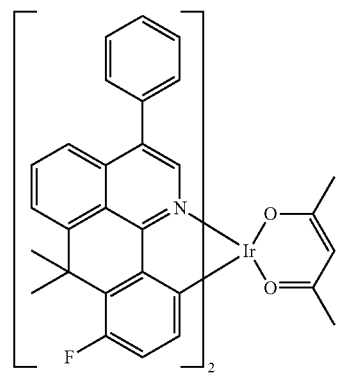
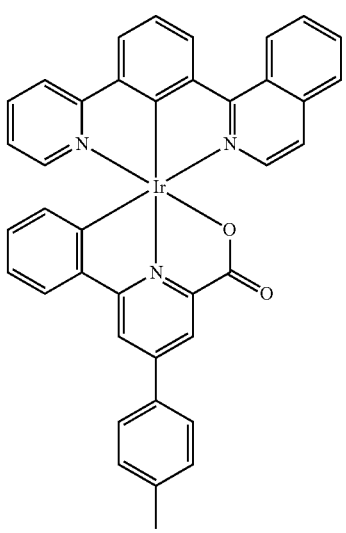
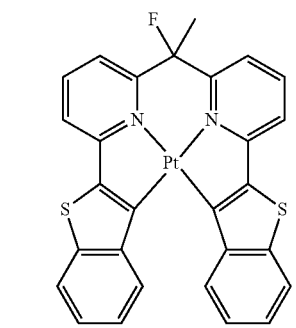

129
-continued
130
-continued
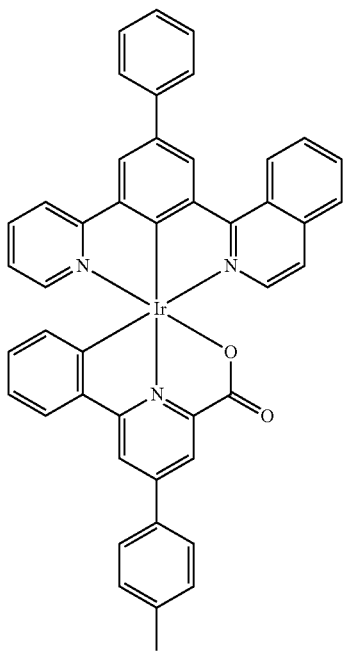
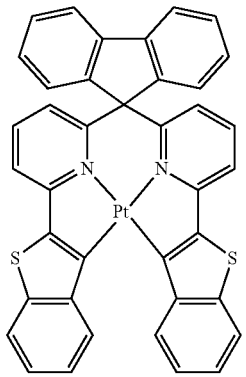
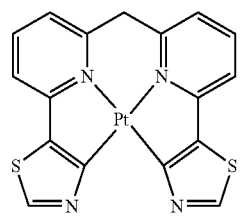
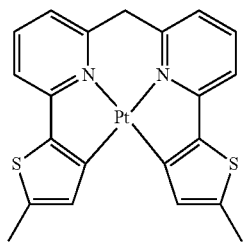
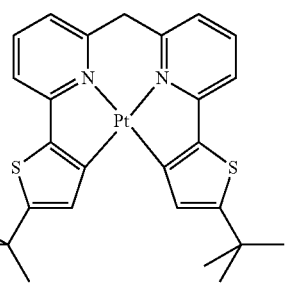
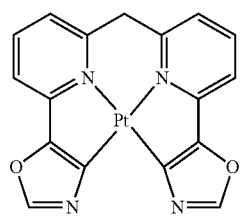
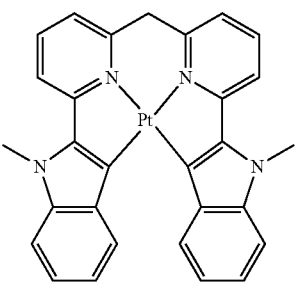

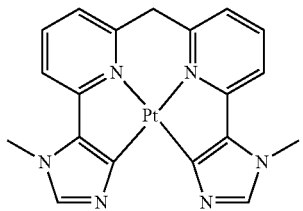
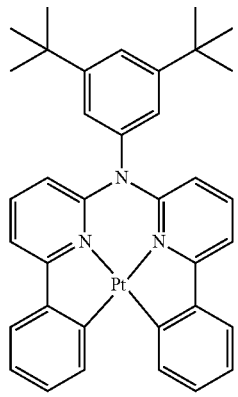
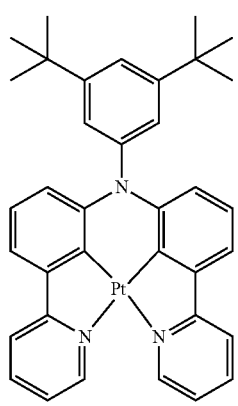
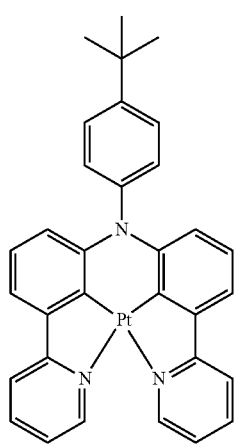
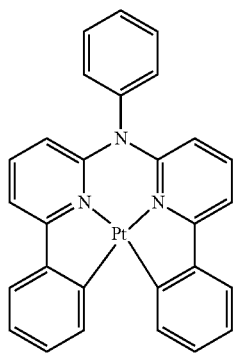
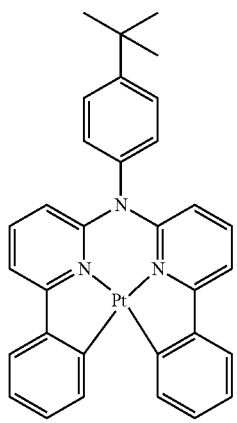
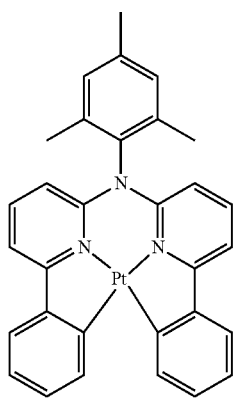
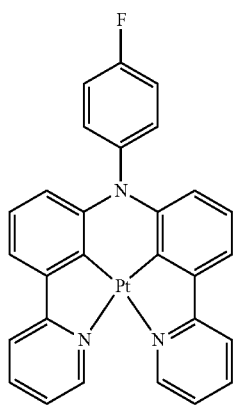

| 133 -continued | 134 -continued |
|---|---|
| 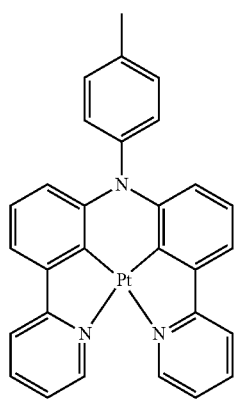 | 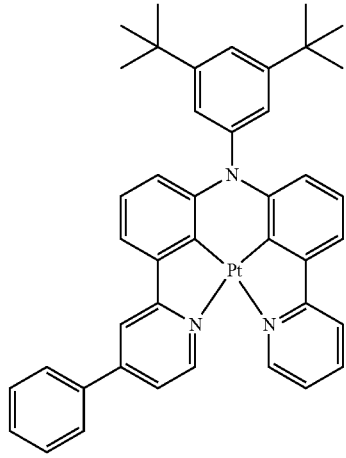 |
| 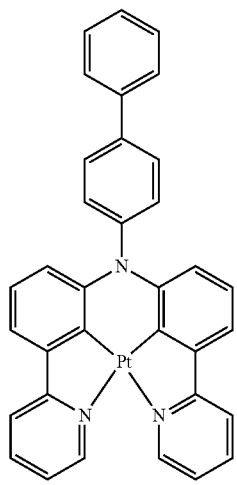 | 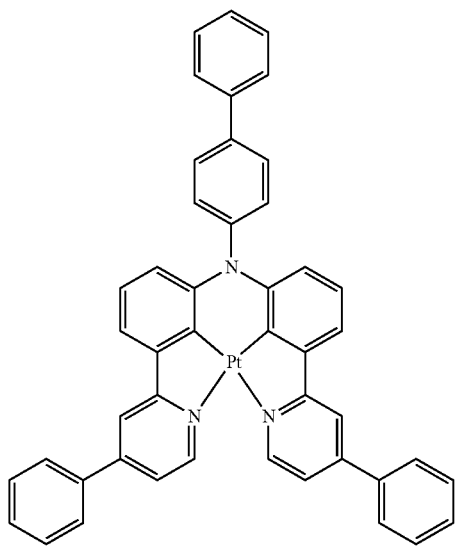 |
| 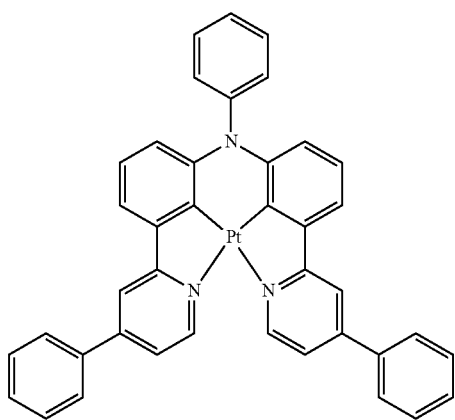 | 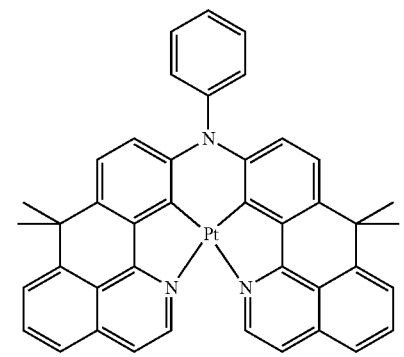 |

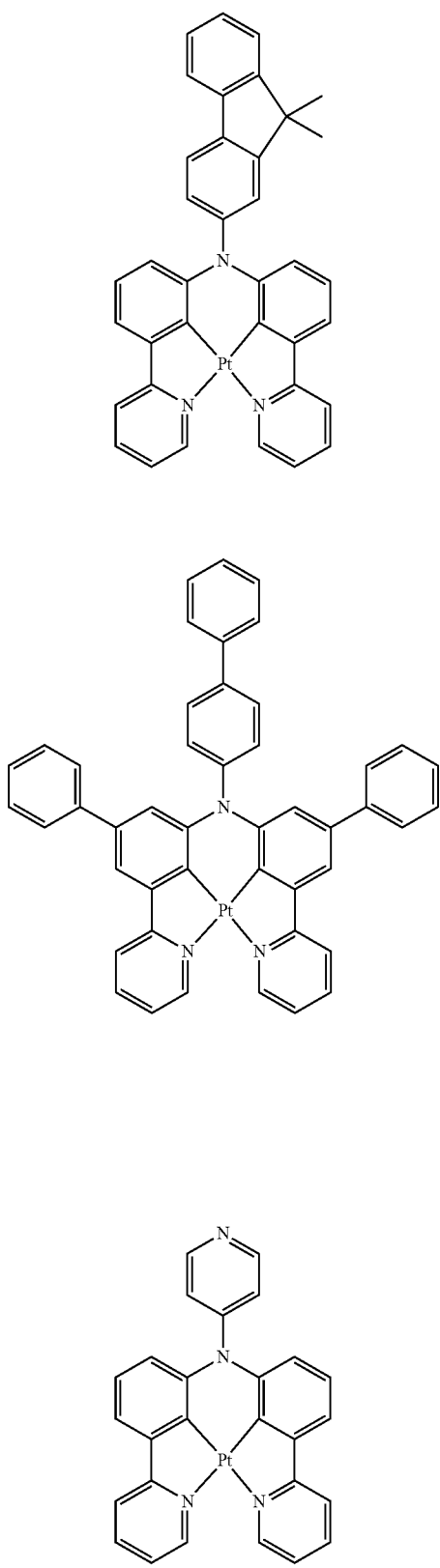
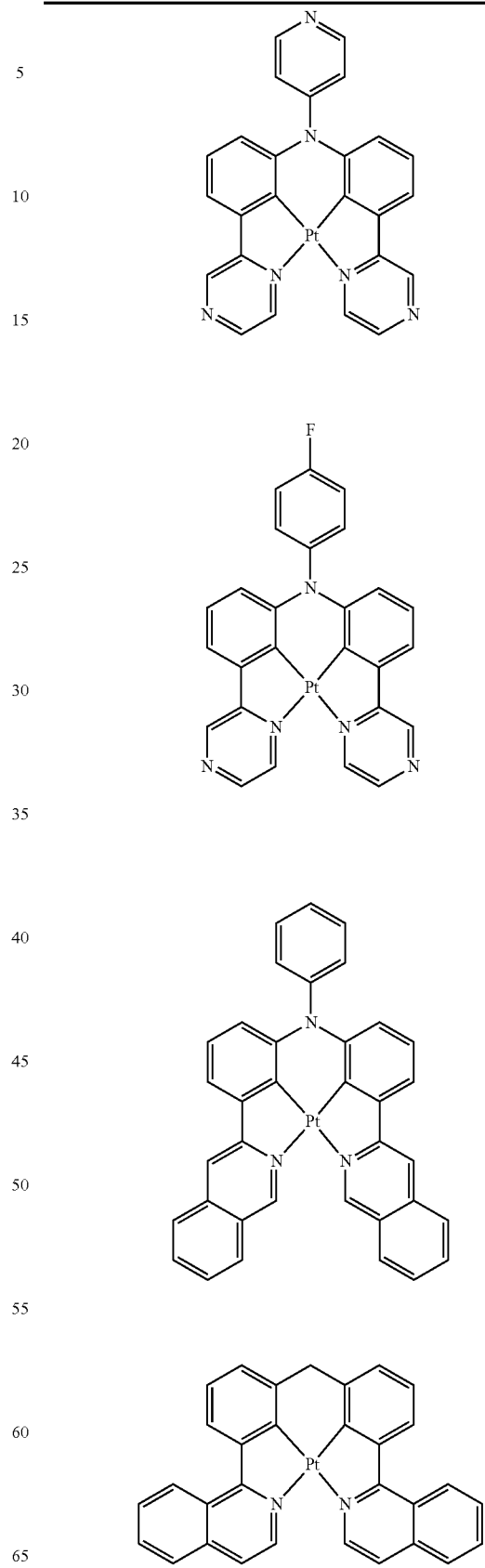

137
-continued
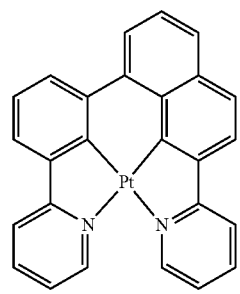
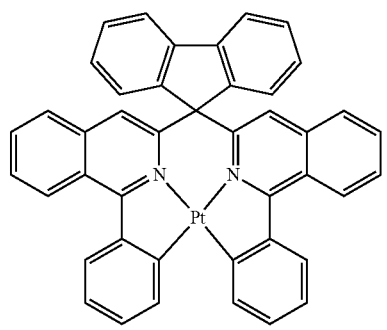
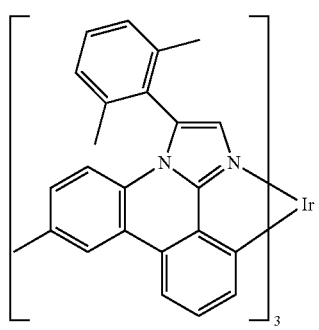
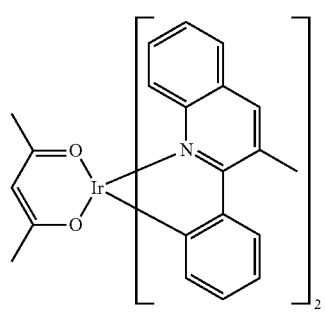
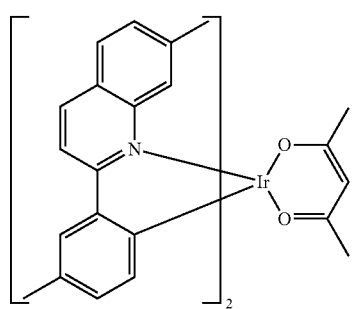
138
-continued
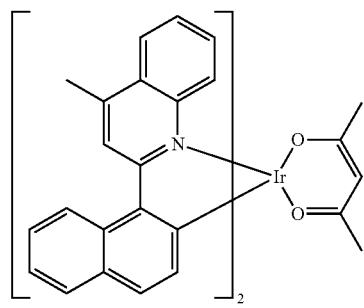
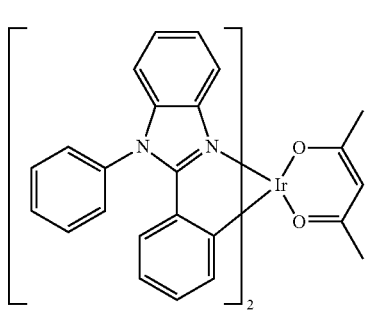
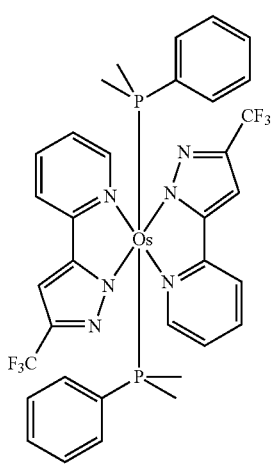
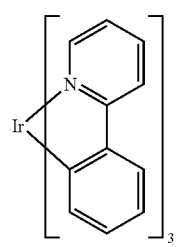
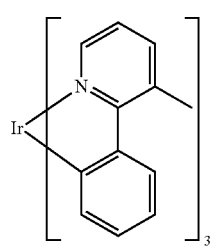

139
-continued
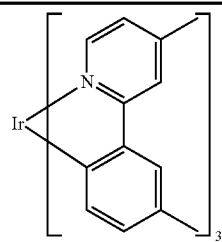
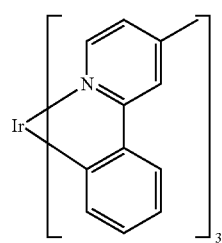
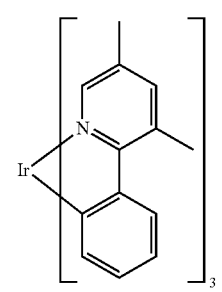
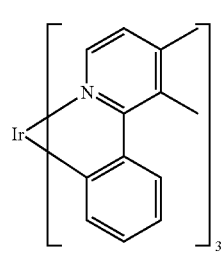
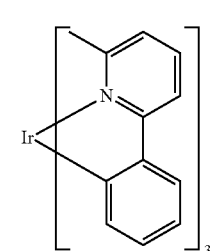
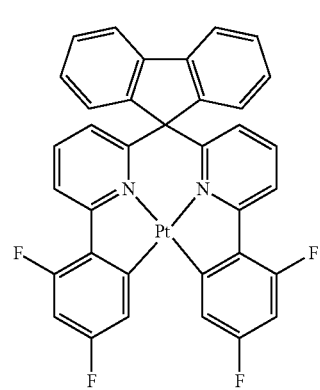
140
-continued
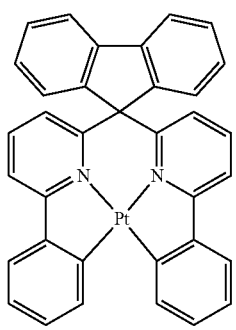
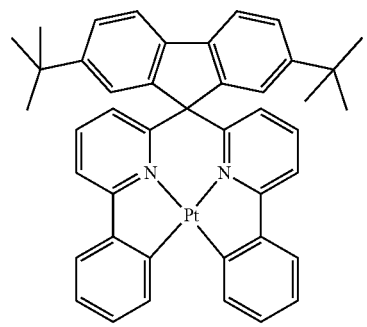
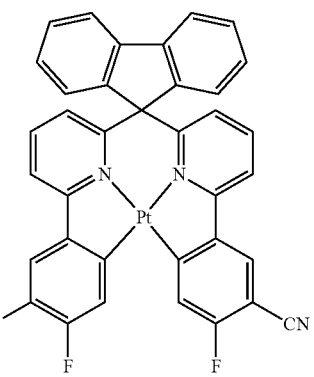
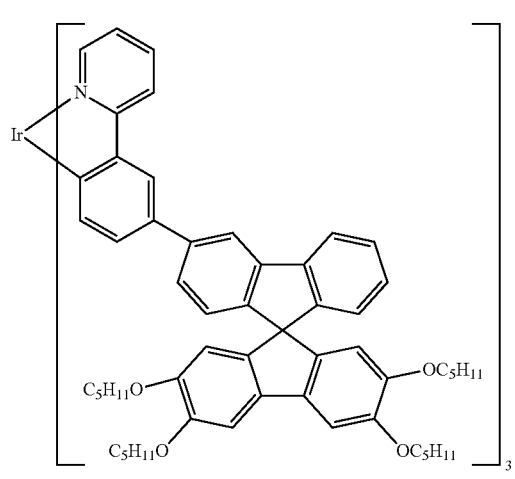

141
-continued
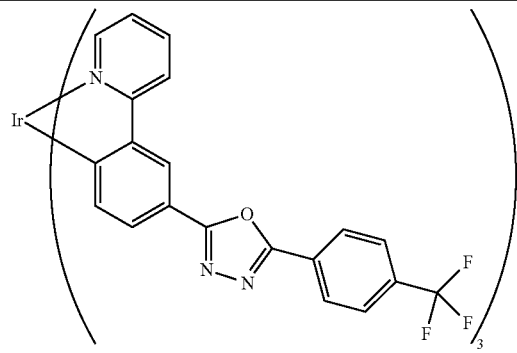
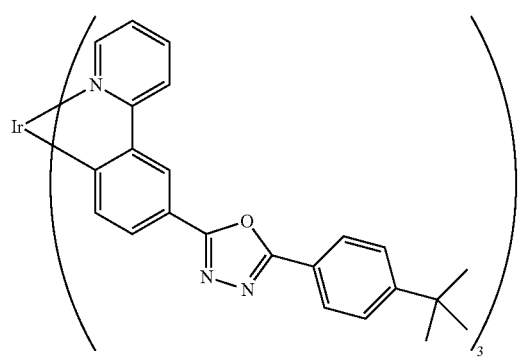
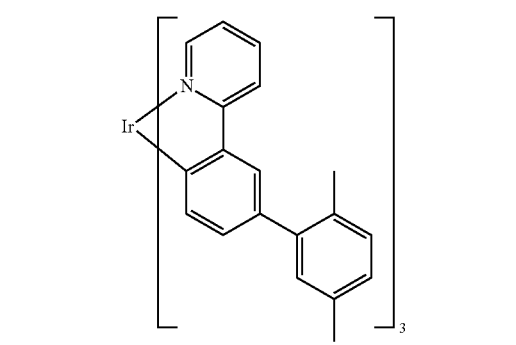
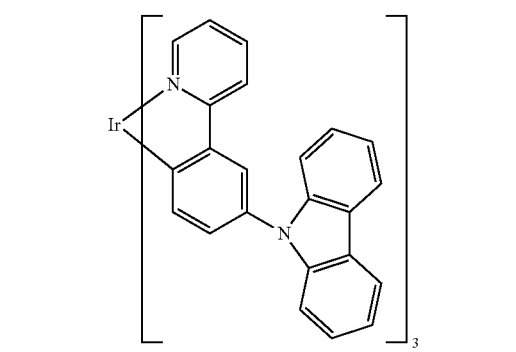
142
-continued
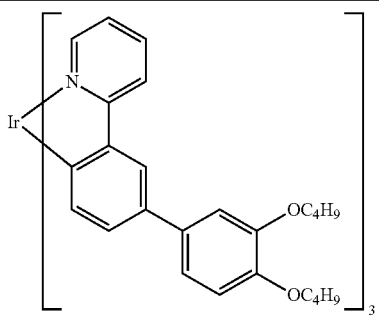
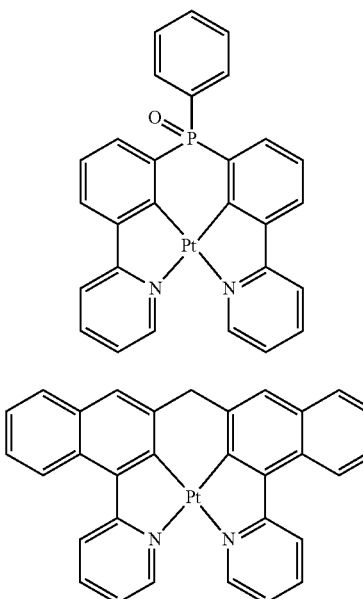
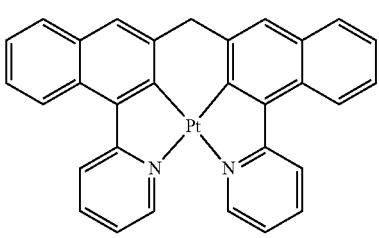
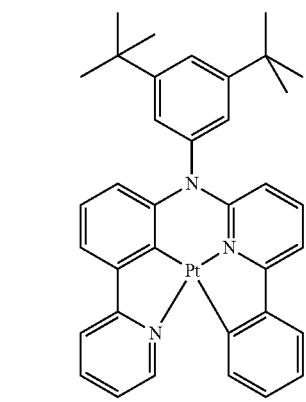
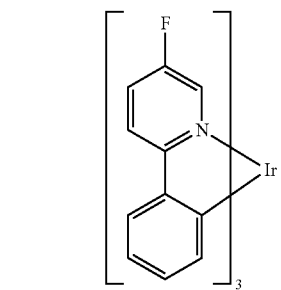

143
-continued
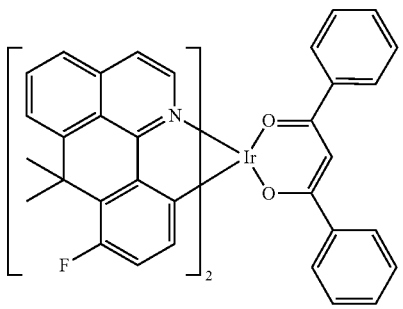
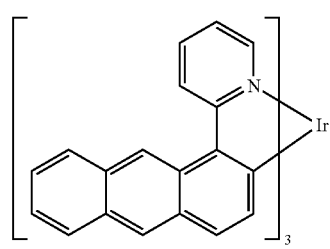
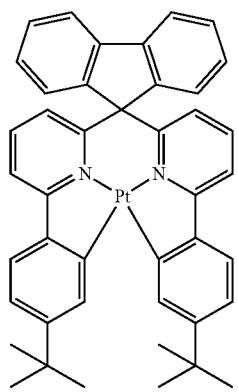
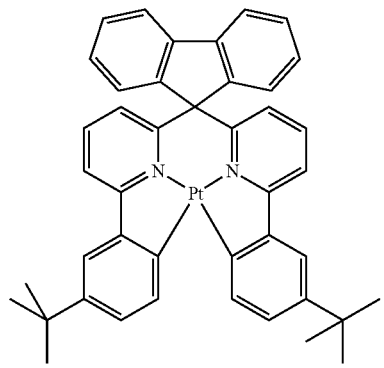
144
-continued
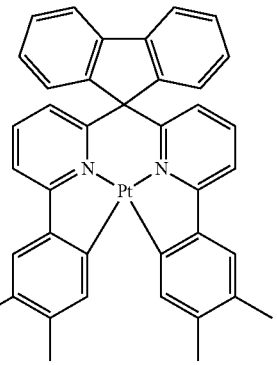
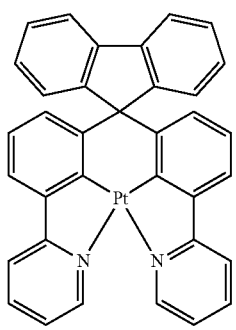
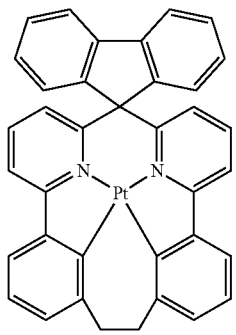
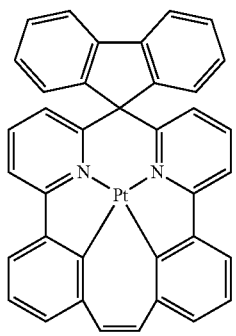

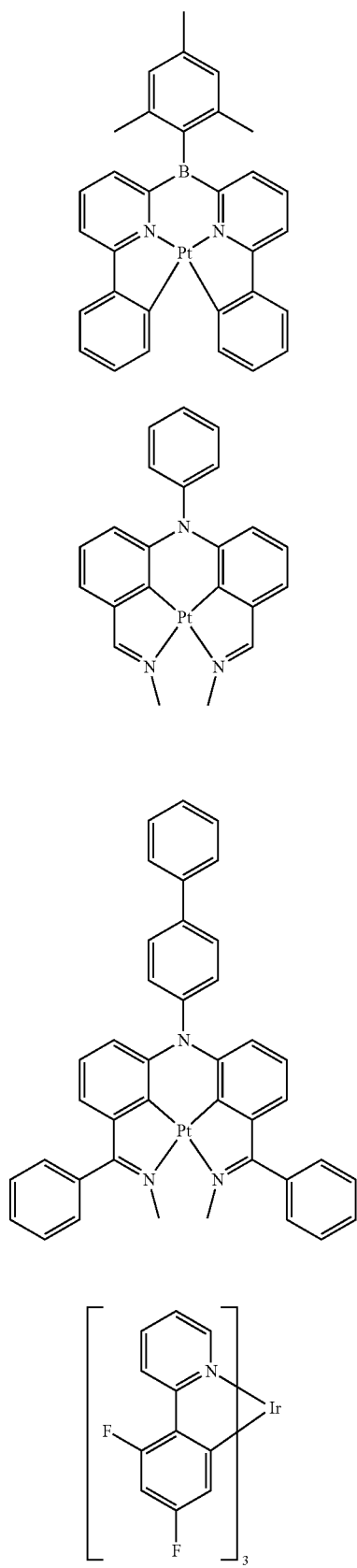
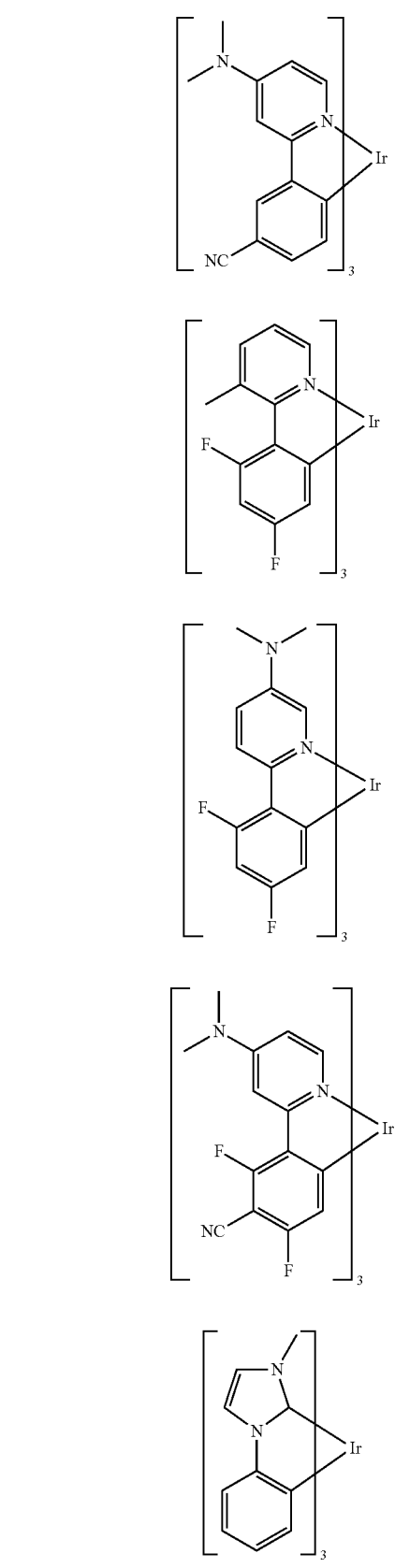

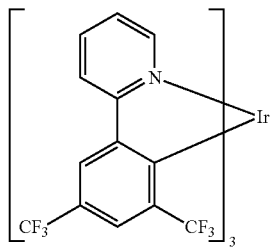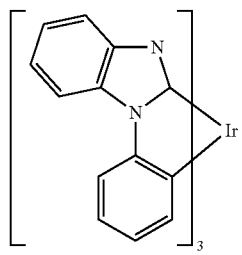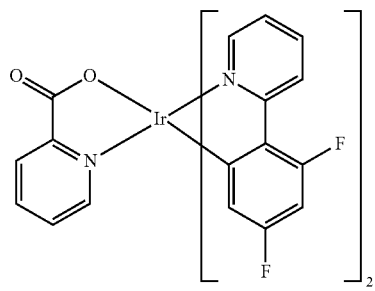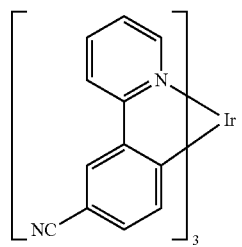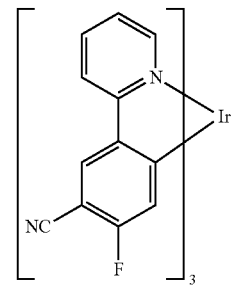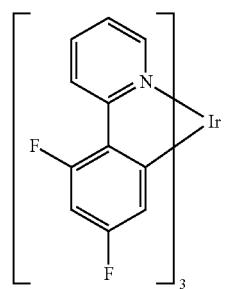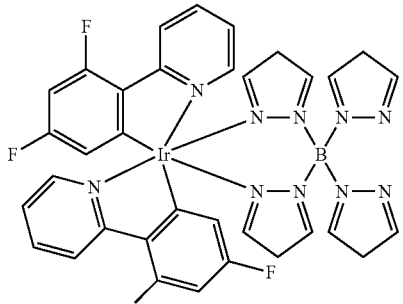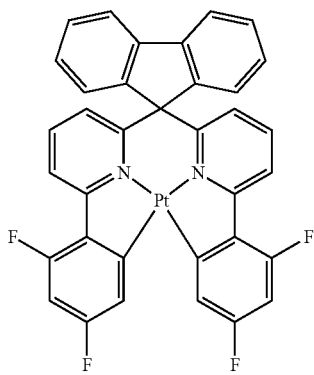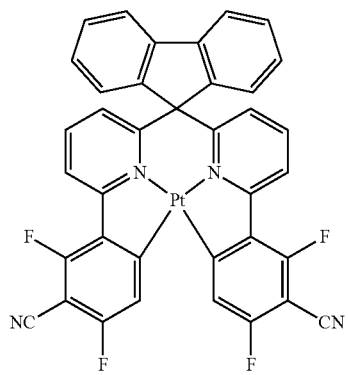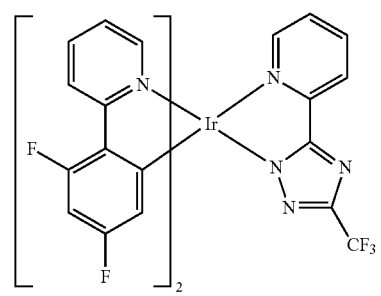

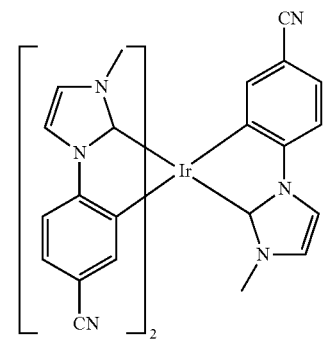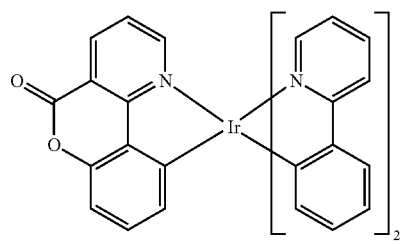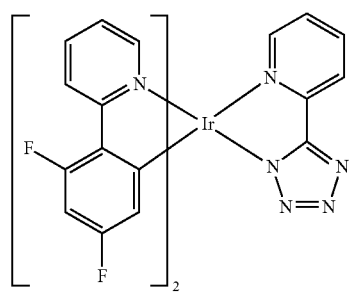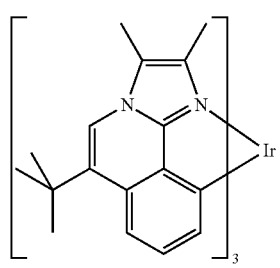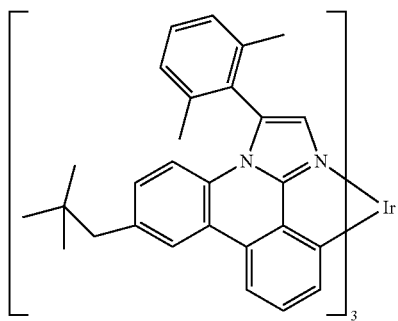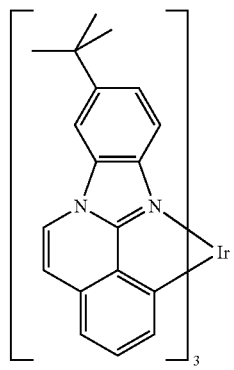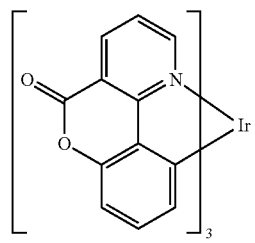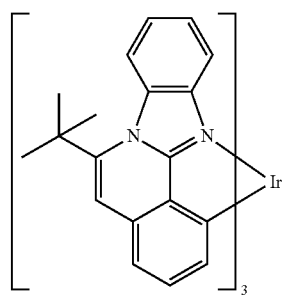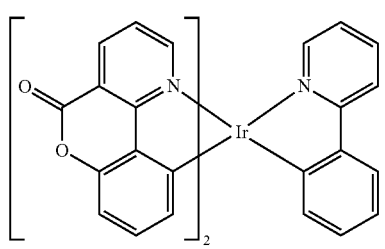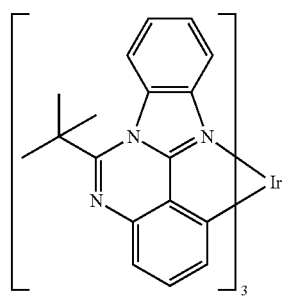

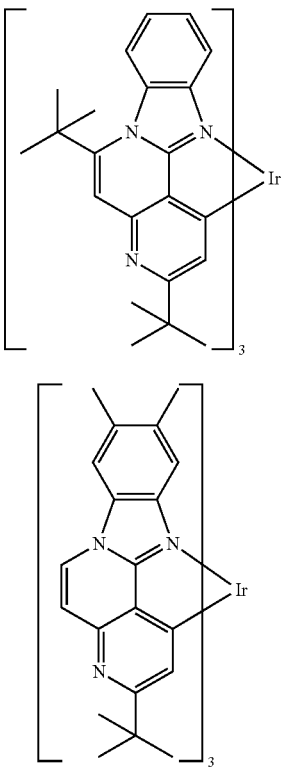

Preferred fluorescent emitters, besides the compounds according to the invention, are selected from the class of the arylamines. An arylamine or aromatic amine here is taken to mean a compound which contains three substituted or unsubstituted aromatic or heteroaromatic ring systems bonded directly to the nitrogen. At least one of these aromatic or heteroaromatic ring systems is preferably a condensed ring system, particularly preferably having at least 14 aromatic ring atoms. Preferred examples thereof are aromatic anthracenamines, aromatic anthracenediamines, aromatic pyrenamines, aromatic pyrenediamines, aromatic chrysenamines or aromatic chrysenediamines. An aromatic anthracenamine is taken to mean a compound in which one diarylamino group is bonded directly to an anthracene group, preferably in the 9-position. An aromatic anthracenediamine is taken to mean a compound in which two diarylamino groups are bonded directly to an anthracene group, preferably in the 9,10-position. Aromatic pyrenamines, pyrenediamines, chrysenamines and chrysenediamines are defined analogously thereto, where the diarylamino groups are preferably bonded to the pyrene in the 1-position or in the 1,6-position. Further preferred fluorescent emitters are indenofluorenamines or indenofluorenediamines, for example in accordance with WO 2006/108497 or WO 2006/122630, benzoindenofluorenamines or benzoindenofluorenediamines, for example in accordance with WO 2008/006449, and dibenzoindenofluorenamines or dibenzoindenofluorenediamines, for example in accordance with WO 2007/140847, and the indenofluorene derivatives containing condensed aryl groups which are disclosed in WO 2010/012328. Preference is likewise given to the pyrenarylamines disclosed in WO 2012/048780 and the as yet unpublished EP 12004426.8. Preference is likewise given to the benzoindenofluorenamines disclosed in the as yet unpublished EP 12006239.3.

Suitable matrix materials, preferably for fluorescent emitters, besides the compounds according to the invention, are materials from various classes of substance. Preferred matrix materials are selected from the classes of the oligoarylenes (for example 2,2',7,7'-tetraphenylspirobifluorene in accordance with EP 676461 or dinaphthylanthracene), in particular the oligoarylenes containing condensed aromatic groups, the oligoarylenevinylenes (for example DPVBi or spiro-DPVBi in accordance with EP 676461), the polypodal metal complexes (for example in accordance with WO 2004/081017), the hole-conducting compounds (for example in accordance with WO 2004/058911), the electron-conducting compounds, in particular ketones, phosphine oxides, sulfoxides, etc. (for example in accordance with WO 2005/084081 and WO 2005/084082), the atropisomers (for example in accordance with WO 2006/048268), the boronic acid derivatives (for example in accordance with WO 2006/117052) or the benzanthracenes (for example in accordance with WO 2008/145239). Particularly preferred matrix materials are selected from the classes of the oligoarylenes, comprising naphthalene, anthracene, benzanthracene and/or pyrene or atropisomers of these compounds, the oligoarylenevinylenes, the ketones, the phosphine oxides and the sulfoxides. Very particularly preferred matrix materials are selected from the classes of the oligoarylenes, comprising anthracene, benzanthracene, benzophenanthrene and/or pyrene or atropisomers of these compounds. An oligoarylene in the sense of this invention is intended to be taken to mean a compound in which at least three aryl or arylene groups are bonded to one another. Particularly preferred matrix materials for fluorescent emitters are the anthracene derivatives disclosed in WO 2006/097208, WO 2006/131192, WO 2007/065550, WO 2007/110129, WO 2007/065678, WO 2008/145239, WO 2009/100925, WO 2011/054442 and EP 1553154. Preferred matrix materials for fluorescent emitters are the pyrene compounds disclosed in EP 1749809, EP 1905754 and US 2012/0187826.

Preferred matrix materials for phosphorescent emitters, besides the compounds according to the invention, are aromatic amines, in particular triarylamines, for example in accordance with US 2005/0069729, carbazole derivatives (for example CBP, N,N-biscarbazolylbiphenyl) or compounds in accordance with WO 2005/039246, US 2005/0069729, JP 2004/288381, EP 1205527 or WO 2008/086851, bridged carbazole derivatives, for example in accordance with WO 2011/088877 and WO 2011/128017, indenocarbazole derivatives, for example in accordance with WO 2010/136109 and WO 2011/000455, azacarbazole derivatives, for example in accordance with EP 1617710, EP 1617711, EP 1731584, JP 2005/347160, indolocarbazole derivatives, for example in accordance with WO 2007/063754 or WO 2008/056746, ketones, for example in accordance with WO 2004/093207 or WO 2010/006680, phosphine oxides, sulfoxides and sulfones, for example in accordance with WO 2005/003253, oligophenylenes, bipolar matrix materials, for example in accordance with WO 2007/137725, silanes, for example in accordance with WO 2005/111172, azaboroles or boronic esters, for example in accordance with WO 2006/117052, triazine derivatives, for example in accordance with WO 2010/015306, WO 2007/063754 or WO 2008/056746, zinc complexes, for example in accordance with EP 652273 or WO 2009/062578, aluminium complexes, for example BAlq, diazasilole and tetraazasilole derivatives, for example in accordance with WO 2010/054729, and diazaphosphole derivatives, for example in accordance with WO 2010/054730.

Suitable charge-transport materials, as can be used in the hole-injection or hole-transport layer or electron-blocking layer or in the electron-transport layer of the organic electroluminescent device according to the invention, are, for example, the compounds disclosed in Y. Shirota et al., Chem. Rev. 2007, 107(4), 953-1010, or other materials as are employed in these layers in accordance with the prior art.

Materials which can be used for the electron-transport layer are all materials as are used in accordance with the prior art as electron-transport materials in the electron-transport layer. Particularly suitable are aluminium complexes, for example $Alq_3$, zirconium complexes, for example $Zrq_4$, benzimidazole derivatives, triazine derivatives, pyrimidine derivatives, pyridine derivatives, pyrazine derivatives, quinoxaline derivatives, quinoline derivatives, oxadiazole derivatives, aromatic ketones, lactams, boranes, diazaphosphole derivatives and phosphine oxide derivatives. Furthermore suitable materials are derivatives of the above-mentioned compounds, as disclosed in JP 2000/053957, WO 2003/060956, WO 2004/028217, WO 2004/080975 and WO 2010/072300.

Preferred hole-transport materials which can be used in a hole-transport, hole-injection or electron-blocking layer in the electroluminescent device according to the invention are indenofluorenamine derivatives (for example in accordance with WO 06/122630 or WO 06/100896), the amine derivatives disclosed in EP 1661888, hexaazatriphenylene derivatives (for example in accordance with WO 01/049806), amine derivatives containing condensed aromatic rings (for example in accordance with U.S. Pat. No. 5,061,569), the amine derivatives disclosed in WO 95/09147, monobenzoindenofluorenamines (for example in accordance with WO 08/006449), dibenzoindenofluorenamines (for example in accordance with WO 07/140847), spirobifluorenamines (for example in accordance with WO 2012/034627 or WO 2013/120577), fluorenamines (for example in accordance with the as yet unpublished applications EP 12005369.9, EP 12005370.7 and EP 12005371.5), spirodibenzopyranamines (for example in accordance with WO 2013/083216) and dihydroacridine derivatives (for example in accordance with WO 2012/150001). The compounds according to the invention can also be used as hole-transport materials.

The cathode of the organic electroluminescent device preferably comprises metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.), Also suitable are alloys comprising an alkali metal or alkaline-earth metal and silver, for example an alloy comprising magnesium and silver. In the case of multilayered structures, further metals which have a relatively high work function, such as, for example, Ag or Al, can also be used in addition to the said metals, in which case combinations of the metals, such as, for example, Ca/Ag, Mg/Ag or Ag/Ag, are generally used. It may also be preferred to introduce a thin interlayer of a material having a high dielectric constant between a metallic cathode and the organic semiconductor. Suitable for this purpose are, for example, alkali metal fluorides or alkaline-earth metal fluorides, but also the corresponding oxides or carbonates (for example LiF, $Li_2O$, $BaF_2$, MgO, NaF, CsF, $Cs_2CO_3$, etc.). Furthermore, lithium quinolinate (LiQ) can be used for this purpose. The layer thickness of this layer is preferably between 0.5 and 5 nm.

The anode preferably comprises materials having a high work function. The anode preferably has a work function of greater than 4.5 eV vs. vacuum. Suitable for this purpose are on the one hand metals having a high redox potential, such as, for example, Ag, Pt or Au. On the other hand, metal/metal oxide electrodes (for example $Al/Ni/NiO_x$, $Al/PtO_x$) may also be preferred. For some applications, at least one of the electrodes must be transparent or partially transparent in order to facilitate either irradiation of the organic material (organic solar cells) or the coupling-out of light (OLEDs, O-lasers). Preferred anode materials here are conductive mixed metal oxides. Particular preference is given to indium tin oxide (ITO) or indium zinc oxide (IZO). Preference is furthermore given to conductive, doped organic materials, in particular conductive, doped polymers. Furthermore, the anode may also consist of a plurality of layers, for example of an inner layer of ITO and an outer layer of a metal oxide, preferably tungsten oxide, molybdenum oxide or vanadium oxide.

The device is appropriately (depending on the application) structured, pro-vided with contacts and finally sealed, since the lifetime of the devices according to the invention is shortened in the presence of water and/or air.

In a preferred embodiment, the organic electroluminescent device according to the invention is characterised in that one or more layers are coated by means of a sublimation process, in which the materials are applied by vapour deposition in vacuum sublimation units at an initial pressure of less than $10^{-5}$ mbar, preferably less than $10^{-6}$ mbar. However, it is also possible here for the initial pressure to be even lower, for example less than $10^{-7}$ mbar.

Preference is likewise given to an organic electroluminescent device, characterised in that one or more layers are coated by means of the OVPD (organic vapour phase deposition) process or with the aid of carrier-gas sublimation, in which the materials are applied at a pressure of between $10^{-5}$ mbar and 1 bar. A special case of this process is the OVJP (organic vapour jet printing) process, in which the materials are applied directly through a nozzle and are thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, nozzle printing or offset printing, but particularly preferably LITI (light induced thermal imaging, thermal transfer printing) or ink-jet printing. Soluble compounds of the formula (I) are necessary for this purpose. High solubility can be achieved through suitable substitution of the compounds.

For the production of an organic electroluminescent device according to the invention, it is furthermore preferred to apply one or more layers from solution and one or more layers by a sublimation process.

In accordance with the invention, the electronic devices comprising one or more compounds of the formula (I) can be employed in displays, as light sources in lighting applications and as light sources in medical and/or cosmetic applications (for example light therapy).

WORKING EXAMPLES

A) Synthesis Examples

Example 1-1

Synthesis of Compound 1-1 According to the Invention

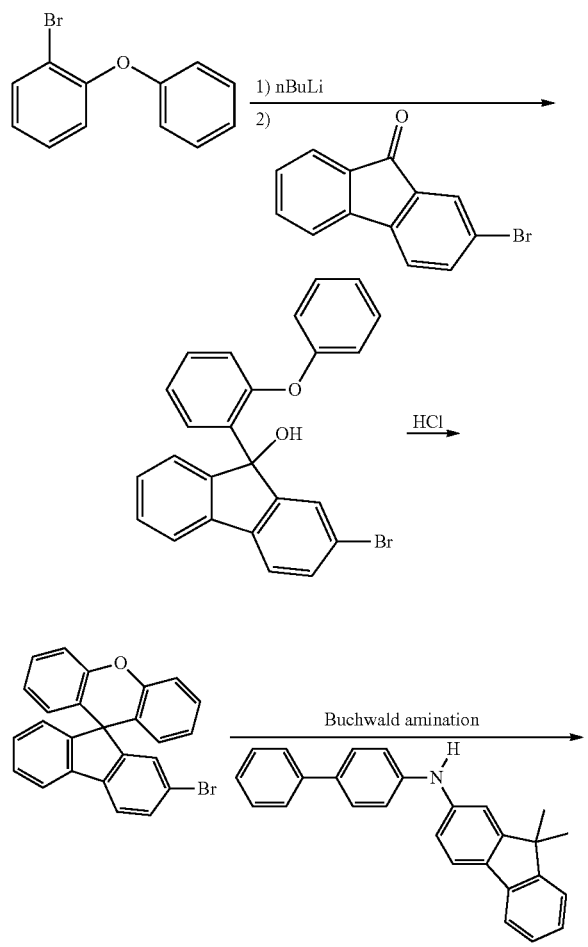

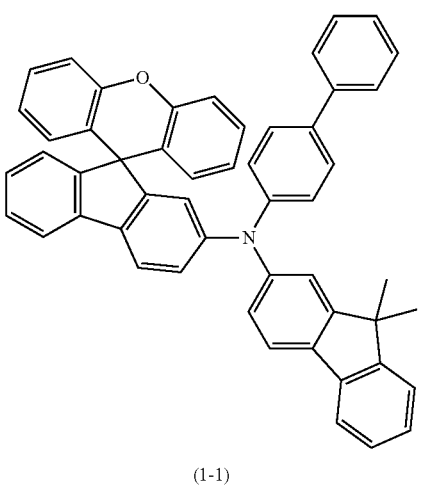

(1-1)

Intermediate: Bromospirofluorenylxanthene Derivative 31.7 g (127 mmol) of 1-bromo-2-diphenyl ether are dissolved in 400 ml of dried THF in a flask which has been dried by heating. The reaction mixture is cooled to −78° C. At this temperature, 55 ml of a 2.5M solution of n-BuLi in hexane (127 mmol) are slowly added dropwise. The batch is stirred at −70° C. for a further 1 hour. 30 g of 2-bromofluorenone (116 mmol) are subsequently dissolved in 100 ml of THF and added dropwise at −70° C. When the addition is complete, the reaction mixture is slowly warmed to room temperature, quenched using NH$_4$Cl and subsequently evaporated in a rotary evaporator. 300 ml of acetic acid are carefully added to the evaporated solution, and 50 ml of fuming HCl are subsequently added. The batch is heated to 75° C. and kept at this temperature for 6 hours. During this time, a white solid precipitates out. The batch is then cooled to room temperature, and the precipitated solid is filtered off with suction and rinsed with methanol. Yield: 45 g (95%).

The following compounds are prepared analogously:

| Starting material 1 | Starting material 2 | Product | Yield |
|---|---|---|---|
| | | | 85% |
| | | | 70% |

-continued
| Starting material 1 | Starting material 2 | Product | Yield |
|---|---|---|---|
| 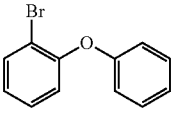 [SMILES: Brc1ccccc1Oc1ccccc1] | 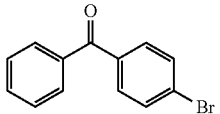 [SMILES: O=C(c1ccccc1)c1ccc(Br)cc1] | 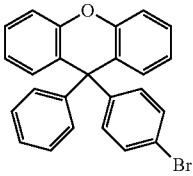 [SMILES: Brc1ccc(C2(c3ccccc3)c3ccccc3Oc3ccccc32)cc1] | 87% |
| 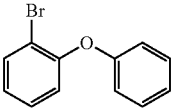 [SMILES: Brc1ccccc1Oc1ccccc1] | 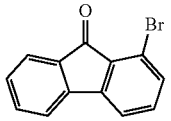 [SMILES: O=C1c2ccccc2-c2cccc(Br)c21] | 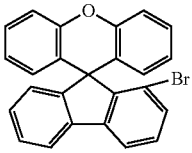 [SMILES: Brc1cccc2c1C1(c3ccccc3Oc3ccccc31)c1ccccc1-2] | 77% |
| 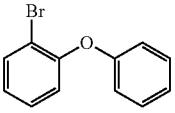 [SMILES: Brc1ccccc1Oc1ccccc1] | 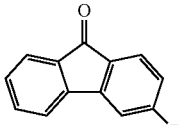 | 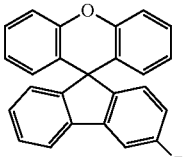 | 65% |
| 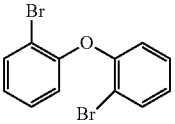 [SMILES: Brc1ccccc1Oc1ccccc1Br] | 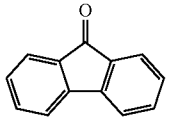 [SMILES: O=C1c2ccccc2-c2ccccc21] | 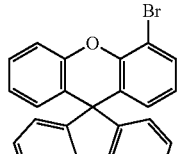 | 73% |
| 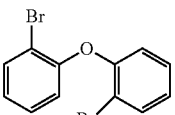 | 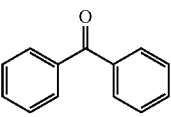 [SMILES: O=C(c1ccccc1)c1ccccc1] | 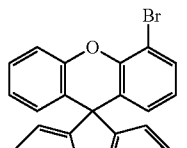 | 69% |
| 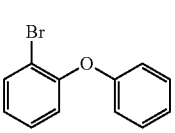 [SMILES: Brc1ccccc1Oc1ccccc1] | 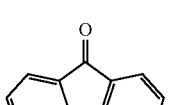 | 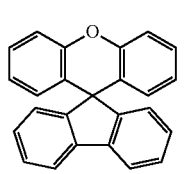 [SMILES: c1ccc2c(c1)Oc1ccccc1C21c2ccccc2-c2ccccc21] | 88% |
| 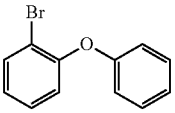 [SMILES: Brc1ccccc1Oc1ccccc1] | 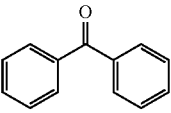 [SMILES: O=C(c1ccccc1)c1ccccc1] | 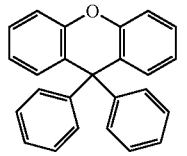 [SMILES: c1ccc(C2(c3ccccc3)c3ccccc3Oc3ccccc32)cc1] | 91% |
| 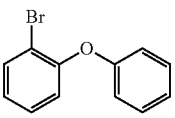 [SMILES: Brc1ccccc1Oc1ccccc1] | 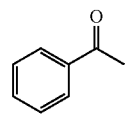 | 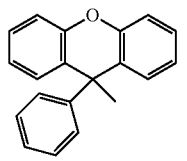 [SMILES: CC1(c2ccccc2)c2ccccc2Oc2ccccc21] | 80% |

| Starting material 1 | Starting material 2 | Product | Yield |
|---|---|---|---|
| 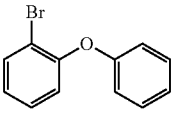 [SMILES: Brc1ccccc1Oc1ccccc1] | 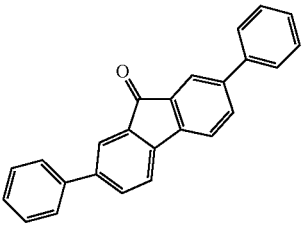 [SMILES: O=C1c2cc(-c3ccccc3)ccc2-c2ccc(-c3ccccc3)cc21] | 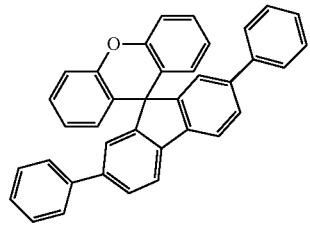 [SMILES: c1ccc(-c2ccc3c(c2)C2(c4ccccc4Oc4ccccc42)c2cc(-c4ccccc4)ccc2-3)cc1] | 83% |

Compound 1-1

17.6 g of biphenyl-4-yl-(9,9-dimethyl-9H-fluoren-2-yl)amine (49 mmol) and 20.0 g of the bromospirofluorenylxanthene (49 mmol) are dissolved in 400 ml of toluene. The solution is degassed and saturated with $N_2$. 2.43 ml (2.43 mmol) of a 1M solution of tri-tert-butyiphosphine and 0.27 g (1.21 mmol) of palladium(II) acetate are then added, and 14 g of sodium tert-butoxide (146 mmol) are subsequently added. The reaction mixture is heated at the boil under a protective atmosphere for 6 h. The mixture is subsequently partitioned between toluene and water, the organic phase is washed three times with water and dried over $Na_2SO_4$ and evaporated in a rotary evaporator. After filtration of the crude product through silica gel with toluene, the residue which remains is recrystallised from heptane/toluene and finally sublimed in a high vacuum. The purity is 99.9%. The yield is 27 g (80% of theory).

The following compounds are prepared analogously:

| | Starting material 1 | Starting material 2 | Product | Yield |
|---|---|---|---|---|
| 1-2 | 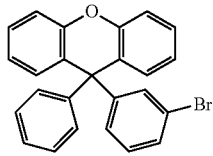 [SMILES: Brc1cccc(C2(c3ccccc3)c3ccccc3Oc3ccccc32)c1] | 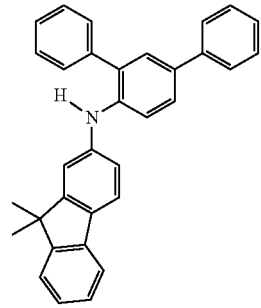 [SMILES: CC1(C)c2ccccc2-c2ccc(Nc3ccc(-c4ccccc4)cc3-c3ccccc3)cc21] | 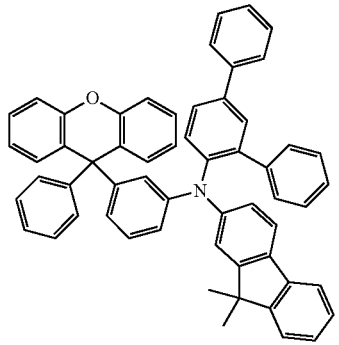 [SMILES: CC1(C)c2ccccc2-c2ccc(N(c3cccc(C4(c5ccccc5)c5ccccc5Oc5ccccc54)c3)c3ccc(-c4ccccc4)cc3-c3ccccc3)cc21] | 78% |
| 1-3 | 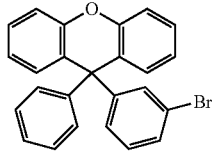 [SMILES: Brc1cccc(C2(c3ccccc3)c3ccccc3Oc3ccccc32)c1] | 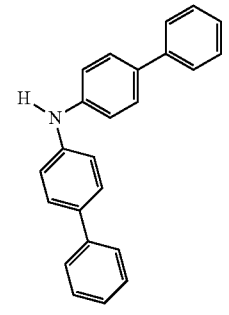 [SMILES: c1ccc(-c2ccc(Nc3ccc(-c4ccccc4)cc3)cc2)cc1] | 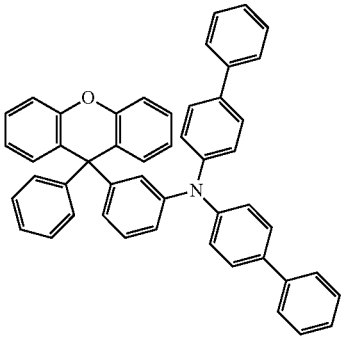 [SMILES: c1ccc(-c2ccc(N(c3ccc(-c4ccccc4)cc3)c3cccc(C4(c5ccccc5)c5ccccc5Oc5ccccc54)c3)cc2)cc1] | 83% |
| 1-4 | 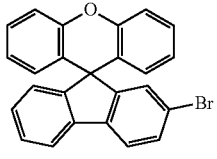 [SMILES: Brc1ccc2c(c1)C1(c3ccccc3Oc3ccccc31)c1ccccc1-2] | 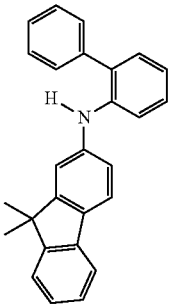 [SMILES: CC1(C)c2ccccc2-c2ccc(Nc3ccccc3-c3ccccc3)cc21] | 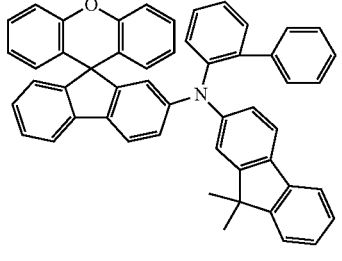 [SMILES: CC1(C)c2ccccc2-c2ccc(N(c3ccc4c(c3)C3(c5ccccc5Oc5ccccc53)c3ccccc3-4)c3ccccc3-c3ccccc3)cc21] | 80% |

-continued
| | Starting material 1 | Starting material 2 | Product | Yield |
|---|---|---|---|---|
| 1-5 | 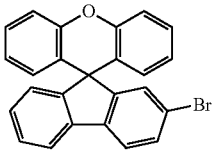 [SMILES: Brc1ccc2c(c1)C1(c3ccccc3Oc3ccccc31)c1ccccc1-2] | 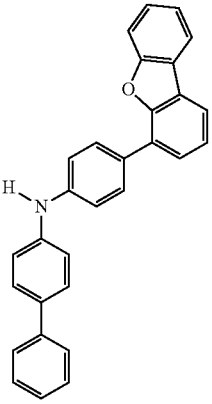 [SMILES: c1ccc(-c2ccc(Nc3ccc(-c4cccc5c4oc4ccccc45)cc3)cc2)cc1] | 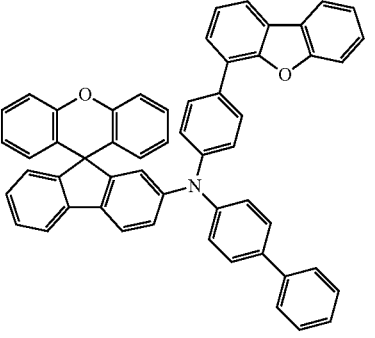 [SMILES: c1ccc(-c2ccc(N(c3ccc(-c4cccc5c4oc4ccccc45)cc3)c3ccc4c(c3)C3(c5ccccc5Oc5ccccc53)c3ccccc3-4)cc2)cc1] | 77% |
| 1-6 |  | 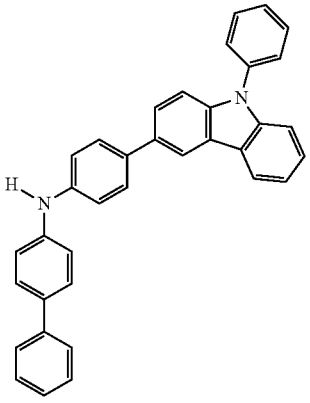 [SMILES: c1ccc(-c2ccc(Nc3ccc(-c4ccc5c(c4)c4ccccc4n5-c4ccccc4)cc3)cc2)cc1] | 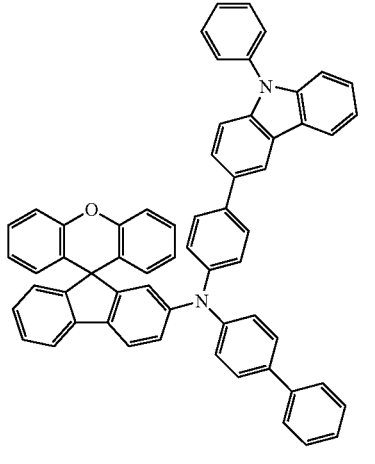 [SMILES: c1ccc(-c2ccc(N(c3ccc(-c4ccc5c(c4)c4ccccc4n5-c4ccccc4)cc3)c3ccc4c(c3)C3(c5ccccc5Oc5ccccc53)c3ccccc3-4)cc2)cc1] | 89% |
| 1-7 |  | 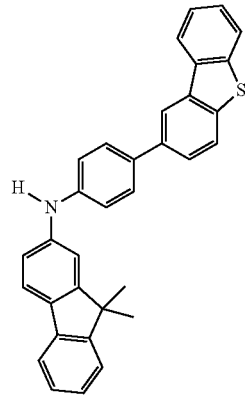 [SMILES: CC1(C)c2ccccc2-c2ccc(Nc3ccc(-c4ccc5sc6ccccc6c5c4)cc3)cc21] | 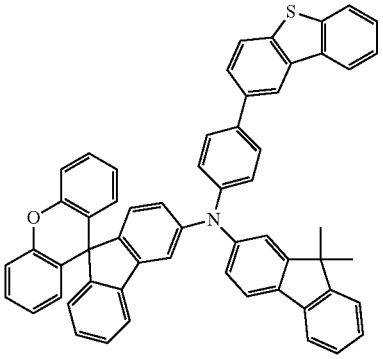 [SMILES: CC1(C)c2ccccc2-c2ccc(N(c3ccc(-c4ccc5sc6ccccc6c5c4)cc3)c3ccc4c(c3)-c3ccccc3C43c4ccccc4Oc4ccccc43)cc21] | 65% |
| 1-8 | 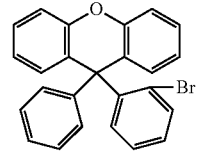 [SMILES: Brc1ccccc1C1(c2ccccc2)c2ccccc2Oc2ccccc21] | 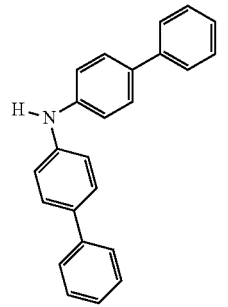 [SMILES: c1ccc(-c2ccc(Nc3ccc(-c4ccccc4)cc3)cc2)cc1] | 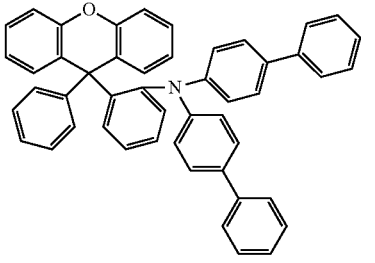 [SMILES: c1ccc(-c2ccc(N(c3ccc(-c4ccccc4)cc3)c3ccccc3C3(c4ccccc4)c4ccccc4Oc4ccccc43)cc2)cc1] | 64% |

| Starting material 1 | Starting material 2 | Product | Yield |
|---|---|---|---|
| 1-9 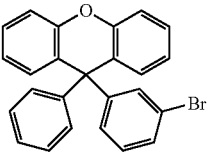 [SMILES: Brc1cccc(C2(c3ccccc3)c3ccccc3Oc3ccccc32)c1] | 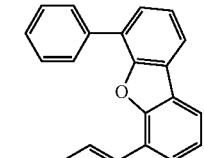 | 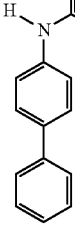 | 71% |
| 1-10 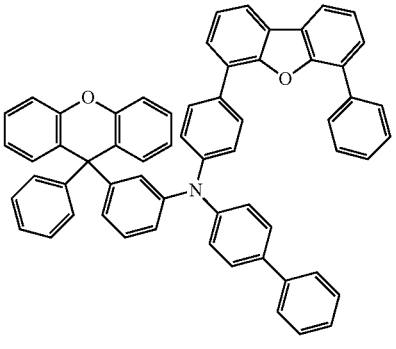 [SMILES: c1ccc(-c2ccc(N(c3ccc(-c4cccc5c4oc4c(-c6ccccc6)cccc45)cc3)c3cccc(C4(c5ccccc5)c5ccccc5Oc5ccccc54)c3)cc2)cc1] | 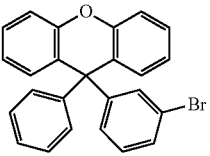 [SMILES: Brc1cccc(C2(c3ccccc3)c3ccccc3Oc3ccccc32)c1] | 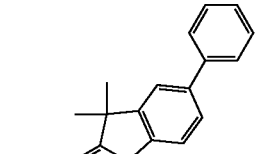 | 78% |
| 1-11 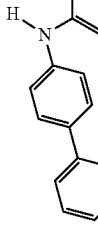 | 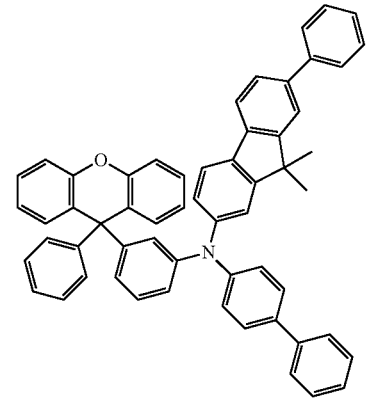 [SMILES: CC1(C)c2cc(-c3ccccc3)ccc2-c2ccc(N(c3ccc(-c4ccccc4)cc3)c3cccc(C4(c5ccccc5)c5ccccc5Oc5ccccc54)c3)cc21] | 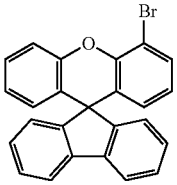 [SMILES: Brc1cccc2c1Oc1ccccc1C21c2ccccc2-c2ccccc21] | 83% |
| 1-12 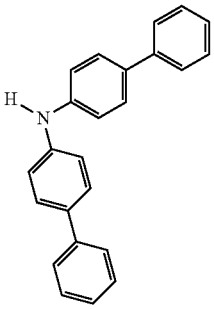 [SMILES: c1ccc(-c2ccc(Nc3ccc(-c4ccccc4)cc3)cc2)cc1] | 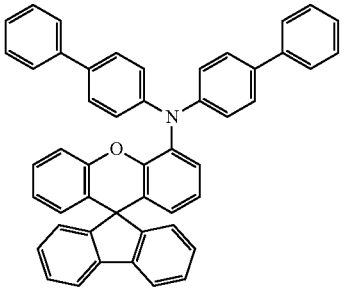 [SMILES: c1ccc(-c2ccc(N(c3ccc(-c4ccccc4)cc3)c3cccc4c3Oc3ccccc3C43c4ccccc4-c4ccccc43)cc2)cc1] | 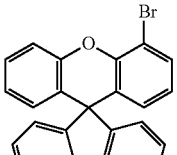 | 85% |

Example 2-1

Synthesis of Compound 2-1 According to the Invention

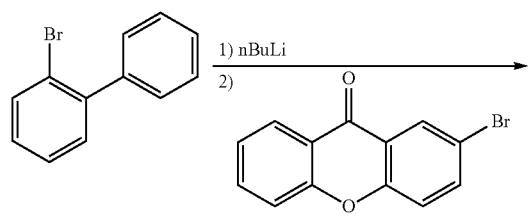

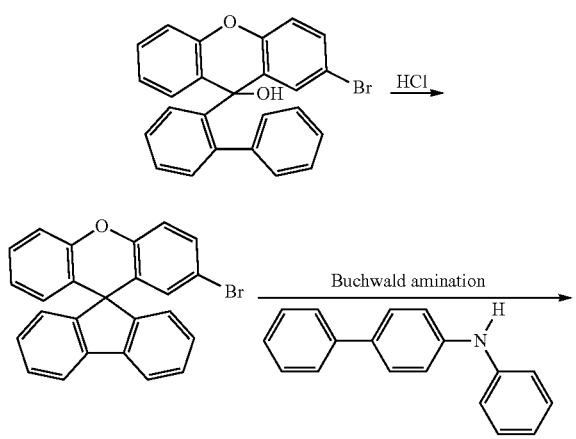

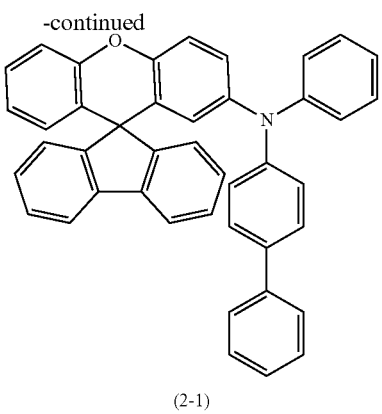

(2-1)

Intermediate: Bromospirofluorenylxanthene Derivative

30 g (129 mmol) of 2-bromobiphenyl are dissolved in 500 ml of dried THF in a flask which has been dried by heating. The reaction mixture is cooled to −78° C. At this temperature, 57 ml of a 2.5M solution of n-BuLi in hexane (142 mmol) are slowly added dropwise. The batch is stirred at −70° C. for a further 1 hour. 35.4 g of 2-bromoxanthen-9-one (129 mmol) are subsequently dissolved in 150 ml of THF and added dropwise at −70° C. When the addition is complete, the reaction mixture is slowly warmed to room temperature, quenched using $NH_4Cl$ and subsequently evaporated in a rotary evaporator. 300 ml of acetic acid are carefully added to the evaporated solution, and 50 ml of fuming HCl are subsequently added. The batch is heated to 75° C. and kept at this temperature for 6 hours. During this time, a white solid precipitates out. The batch is then cooled to room temperature, and the precipitated solid is filtered off with suction and rinsed with methanol.

Yield: 31.5 g (60%).

The following compounds are prepared analogously:

| Starting material 1 | Starting material 2 | Product | Yield |
|---|---|---|---|
| | | | 78% |
| | | | 75% |
| | | | 75% |

Compound 2-1

This compound is prepared analogously to compound 1-1.
Yield: 78%. Purity 99.9%.
The following compounds are prepared analogously:

| | Starting material 1 | Starting material 2 | Product | Yield |
|---|---|---|---|---|
| 2-2 | | | | 78% |
| 2-3 | | | | 72% |
| 2-4 | | | | 75% |
| 2-5 | | | | 82% |

| Starting material 1 | Starting material 2 | Product | Yield |
|---|---|---|---|
| 2-6 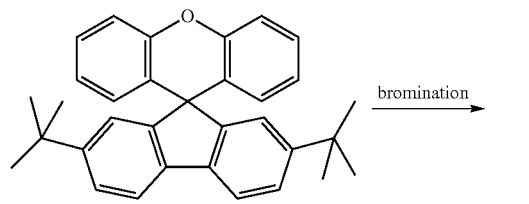 | | | 79% |

Example 3-1

Synthesis of Compound 3-1 According to the Invention

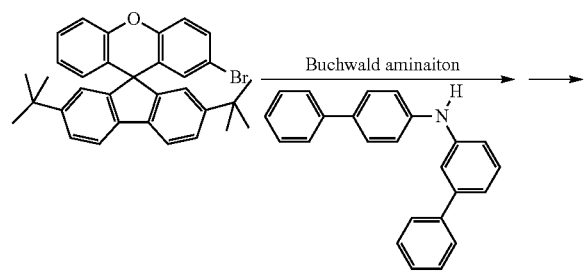

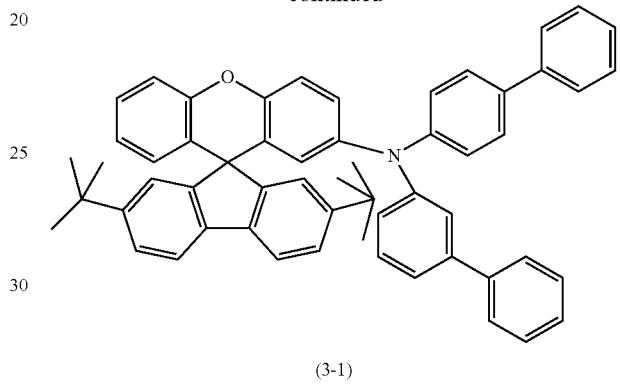

(3-1)

Intermediate: Bromospirofluorenylxanthene Derivative 20 g (60 mmol) of spirofluorenylxanthene are initially introduced in 300 ml of acetonitrile. A solution of 10.7 g (60 mmol) of NBS in 50 ml of $CH_3CN$ is subsequently added dropwise at 0° C. with exclusion of light, the mixture is allowed to come to RT and is stirred at 50° C. for a further 4 h. 150 ml of water are subsequently added to the mixture, which is then extracted with $CH_2Cl_2$. The organic phase is dried over $MgSO_4$, and the solvents are removed in vacuo. The product is washed by stirring with hot hexane and filtered off with suction.

Yield: 13.8 g, 55.9% of theory, purity according to $^1$H-NMR about 97%.

The following compounds are prepared analogously:

| Starting material 1 | Product | Yield |
|---|---|---|
| | | 65% |

| Starting material 1 | Product | Yield |
|---|---|---|
| [xanthene-spiro-fluorene with phenyl substituent] | [xanthene-spiro-fluorene with phenyl substituent, Br] | 67% |
| [xanthene-spiro-fluorene with two phenyl substituents] | [xanthene-spiro-fluorene with two phenyl substituents, Br] | 71% |
| [9,9-diaryl xanthene with biphenyl and phenyl] | [9,9-diaryl xanthene with biphenyl and phenyl, Br] | 67% |
| [9-methyl-9-phenyl xanthene] | [9-methyl-9-phenyl xanthene, Br] | 62% |

Compound 3-1

This compound is prepared analogously to compound 1-1.
Yield: 81%. Purity 99.9%.
The following compounds are prepared analogously:

| | Starting material 1 | Starting material 2 | Product | Yield |
|---|---|---|---|---|
| 3-2 | [di-tert-butyl xanthene-spiro-fluorene with Br] | [N-biphenyl-biphenylamine] | [triarylamine xanthene-spiro-fluorene product] | 81% |

US 9,978,949 B2

173                                                                   174

-continued

| Starting material 1 | Starting material 2 | Product | Yield |
|---|---|---|---|
| 3-3 | | | 78% |
| 3-4 | | | 66% |
| 3-5 | | | 77% |
| 3-6 | | | 75% |

-continued

| | Starting material 1 | Starting material 2 | Product | Yield |
|---|---|---|---|---|
| 3-7 | | | | 92% |

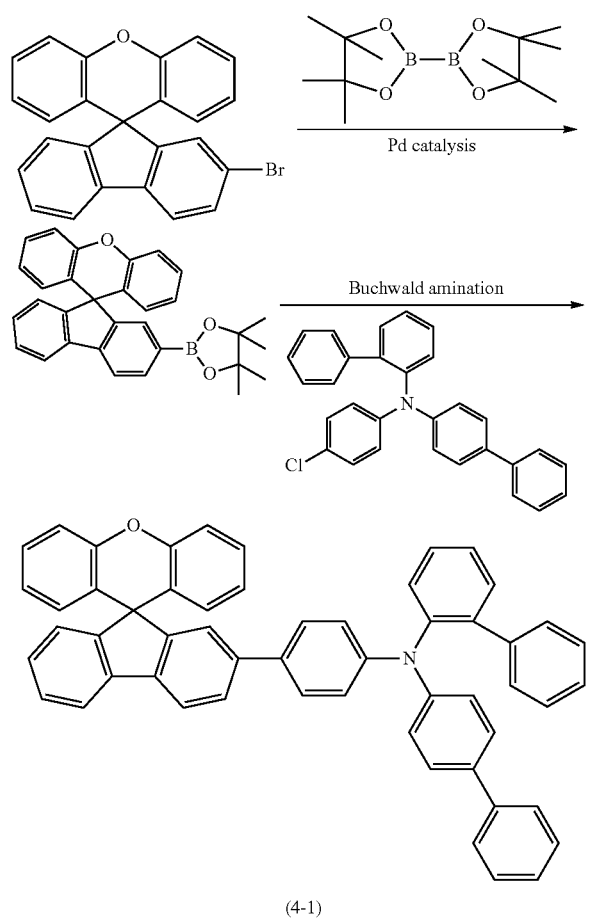

Example 4-1

Synthesis of Compound 4-1 According to the Invention (4-1)

Intermediate: Spirofluorenylxantheneboronic Ester Derivative 20 g (49 mmol) of the bromospirofluorenylxanthene derivative, 13.6 g (53 mmol) of bis(pinacolato)diborane and 14.3 g (146 mmol) of potassium acetate are suspended in 500 ml of dioxane. 1.19 g (1 mmol) of 1,1-bis-(diphenylphosphino)ferrocenepalladium(II) dichloride complex with DCM are added to this suspension. The reaction mixture is heated under reflux for 16 h. After cooling, the organic phase is separated off, washed three times with 200 ml of water and subsequently evaporated to dryness. The residue is recrystallised from toluene (20 g, 90% yield).

The following compounds are prepared analogously:

| Starting material 1 | Product | Yield |
|---|---|---|
| | | 90% |
| | | 80% |
| | | 88% |
| | | 82% |

Precursor: Biphenyl-2-ylbiphenyl-4-yl-(4-chlorophenyl)amine

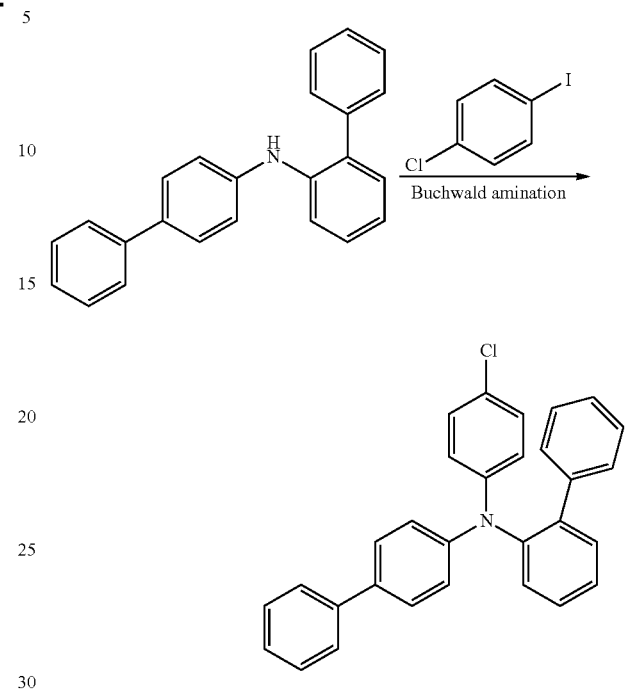

23.8 g of biphenyl-2-ylbiphenyl-4-ylamine (74 mmol) and 21.2 g of 4-chloro-iodobenzenebromofluorene (89 mmol) are dissolved in 500 ml of toluene: the solution is degassed and saturated with $N_2$. 3 ml (3 mmol) of a 1M solution of tri-tert-butylphosphine and 0.33 g (1.48 mmol) of palladium(II) acetate are then added, and 10.7 g of sodium tert-butoxide (111 mmol) are subsequently added. The reaction mixture is heated at the boil under a protective atmosphere for 12 h. The mixture is subsequently partitioned between toluene and water, the organic phase is washed three times with water and dried over $Na_2SO_4$ and evaporated in a rotary evaporator. After filtration of the crude product through silica gel with toluene, the residue which remains is recrystallised from heptane/toluene. The yield is 29 g (90% of theory).

The following compounds are prepared analogously:

| Starting material 1 | Starting material 2 | Product | Yield |
|---|---|---|---|
| | | | 80% |
| | | | 67% |
| | | | 81% |
| | | | 92% |

| Starting material 1 | Starting material 2 | Product | Yield |
|---|---|---|---|
| 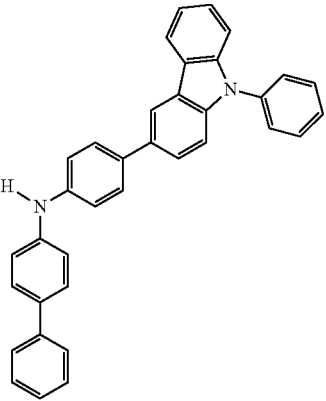 [SMILES: c1ccc(-c2ccc(Nc3ccc(-c4ccc5c(c4)c4ccccc4n5-c4ccccc4)cc3)cc2)cc1] | 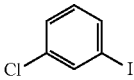 | 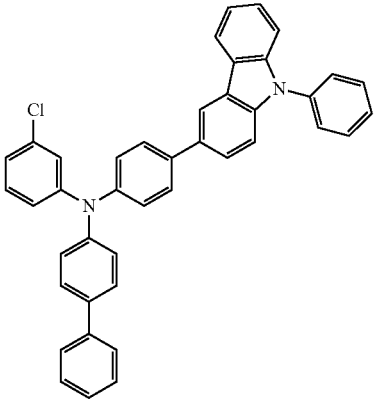 [SMILES: Clc1cccc(N(c2ccc(-c3ccccc3)cc2)c2ccc(-c3ccc4c(c3)c3ccccc3n4-c3ccccc3)cc2)c1] | 85% |
| 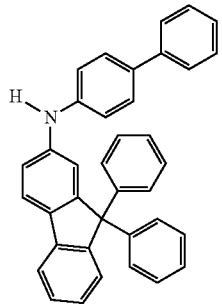 [SMILES: c1ccc(-c2ccc(Nc3ccc4c(c3)C(c3ccccc3)(c3ccccc3)c3ccccc3-4)cc2)cc1] | 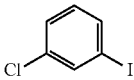 | 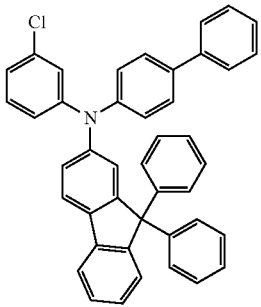 | 80% |
| 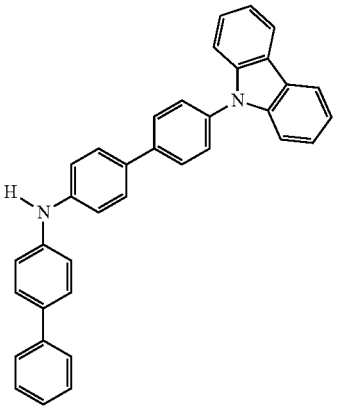 [SMILES: c1ccc(-c2ccc(Nc3ccc(-c4ccc(-n5c6ccccc6c6ccccc65)cc4)cc3)cc2)cc1] | 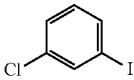 | 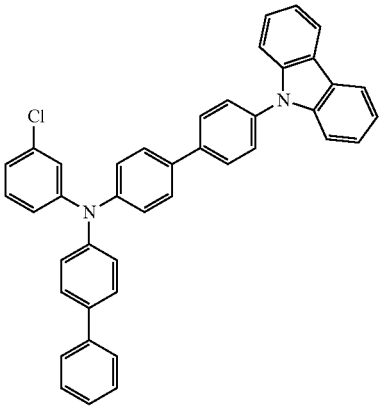 [SMILES: Clc1cccc(N(c2ccc(-c3ccccc3)cc2)c2ccc(-c3ccc(-n4c5ccccc5c5ccccc54)cc3)cc2)c1] | 75% |
| 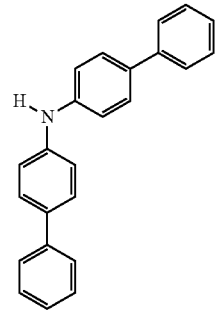 [SMILES: c1ccc(-c2ccc(Nc3ccc(-c4ccccc4)cc3)cc2)cc1] |  | 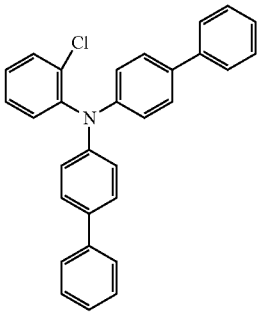 [SMILES: Clc1ccccc1N(c1ccc(-c2ccccc2)cc1)c1ccc(-c2ccccc2)cc1] | 75% |

Compound 4-1

13.8 g (30 mmol) of spirofluorenylxanthenepinacolylboronic ester, 13 g (30 mmol) of 2,7-dibromofluorenone are suspended in 300 ml of dioxane and 9.1 g of caesium fluoride (60 mmol). 2.2 g (3 mmol) of bis(tricyclohexylphosphine)palladium dichloride are added to this suspension, and the reaction mixture is heated under reflux for 18 h. After cooling, the organic phase is separated off, filtered through silica gel, washed three times with 80 ml of water and subsequently evaporated to dryness. After filtration of the crude product through silica gel with toluene, the residue which remains is recrystallised from heptane/toluene and finally sublimed in a high vacuum. The purity is 99.9%. The yield is 17.8 g (85% of theory).

The following compounds are prepared analogously:

| | Starting material 1 | Starting material 2 |
|---|---|---|
| 4-2 | | |
| 4-3 | | |
| 4-4 | | |
| 4-5 | | |

4-6 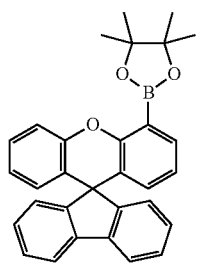 [SMILES: CC1(C)OB(c2cccc3c2Oc2ccccc2C32c3ccccc3-c3ccccc32)OC1(C)C] 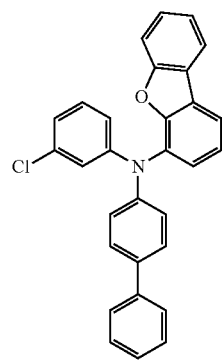 [SMILES: Clc1cccc(N(c2ccc(-c3ccccc3)cc2)c2cccc3c2oc2ccccc23)c1]
4-7 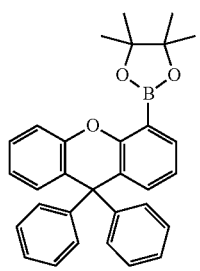 [SMILES: CC1(C)OB(c2cccc3c2Oc2ccccc2C3(c2ccccc2)c2ccccc2)OC1(C)C] 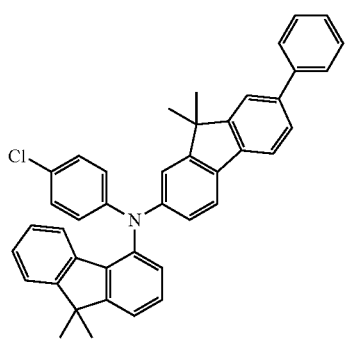 [SMILES: CC1(C)c2cc(-c3ccccc3)ccc2-c2ccc(N(c3ccc(Cl)cc3)c3cccc4c3-c3ccccc3C4(C)C)cc21]
4-8 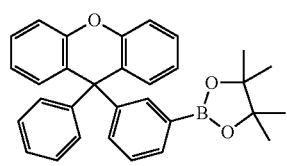 [SMILES: CC1(C)OB(c2cccc(C3(c4ccccc4)c4ccccc4Oc4ccccc43)c2)OC1(C)C] 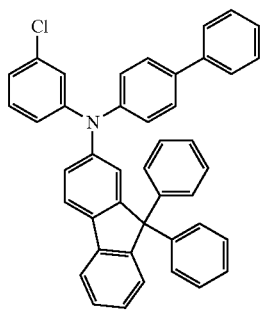 [SMILES: Clc1cccc(N(c2ccc(-c3ccccc3)cc2)c2ccc3c(c2)C(c2ccccc2)(c2ccccc2)c2ccccc2-3)c1]
4-9 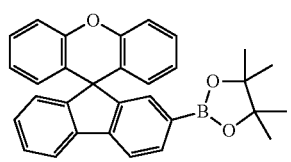 [SMILES: CC1(C)OB(c2ccc3c(c2)C2(c4ccccc4Oc4ccccc42)c2ccccc2-3)OC1(C)C] 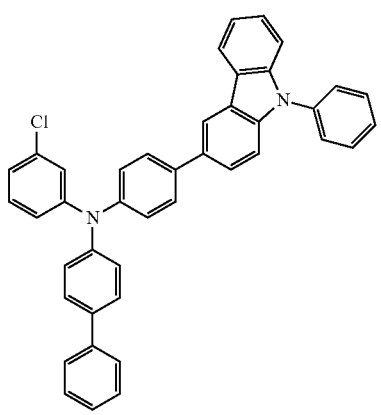 [SMILES: Clc1cccc(N(c2ccc(-c3ccccc3)cc2)c2ccc(-c3ccc4c(c3)c3ccccc3n4-c3ccccc3)cc2)c1]

| | | |
|---|---|---|
| 4-10 | 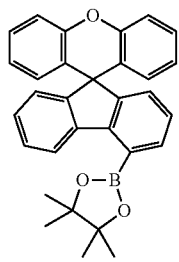 [SMILES: CC1(C)OB(c2cccc3c2-c2ccccc2C32c3ccccc3Oc3ccccc32)OC1(C)C] | 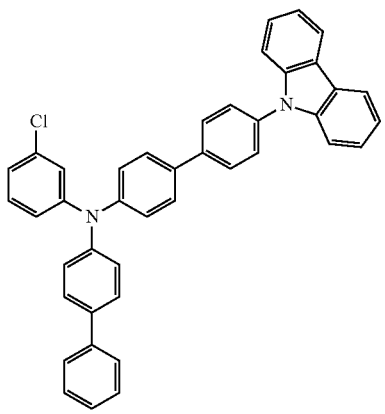 [SMILES: Clc1cccc(N(c2ccc(-c3ccccc3)cc2)c2ccc(-c3ccc(-n4c5ccccc5c5ccccc54)cc3)cc2)c1] |
| 4-11 | 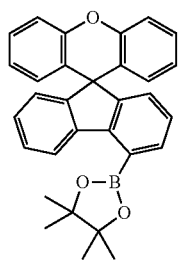 [SMILES: CC1(C)OB(c2cccc3c2-c2ccccc2C32c3ccccc3Oc3ccccc32)OC1(C)C] | 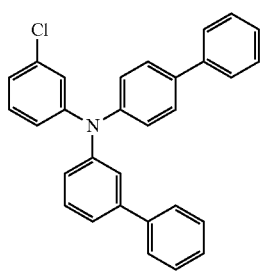 [SMILES: Clc1cccc(N(c2ccc(-c3ccccc3)cc2)c2cccc(-c3ccccc3)c2)c1] |
| | Product | Yield |
|---|---|---|
| 4-2 | 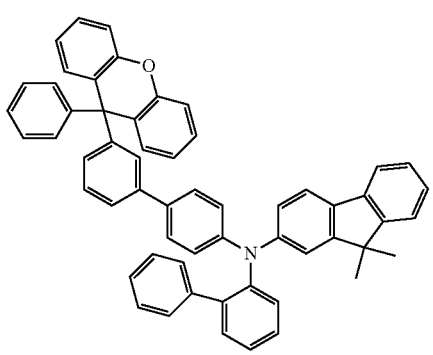 [SMILES: CC1(C)c2ccccc2-c2ccc(N(c3ccc(-c4cccc(C5(c6ccccc6)c6ccccc6Oc6ccccc65)c4)cc3)c3ccccc3-c3ccccc3)cc21] | 78% |
| 4-3 | 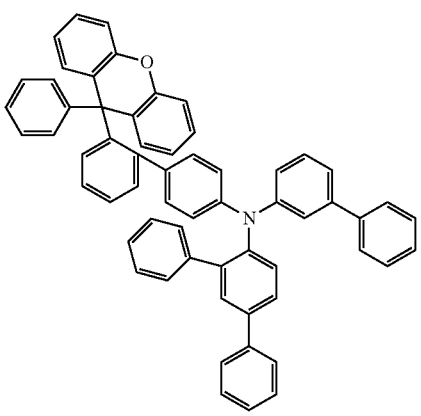 [SMILES: c1ccc(-c2cccc(N(c3ccc(-c4ccccc4C4(c5ccccc5)c5ccccc5Oc5ccccc54)cc3)c3ccc(-c4ccccc4)cc3-c3ccccc3)c2)cc1] | 71% |

| | |
|---|---|
| 4-4 | 82% |
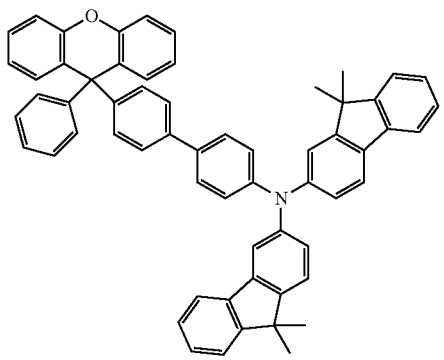 [SMILES: CC1(C)c2ccccc2-c2cc(N(c3ccc(-c4ccc(C5(c6ccccc6)c6ccccc6Oc6ccccc65)cc4)cc3)c3ccc4c(c3)C(C)(C)c3ccccc3-4)ccc21]
| | |
|---|---|
| 4-5 | 89% |
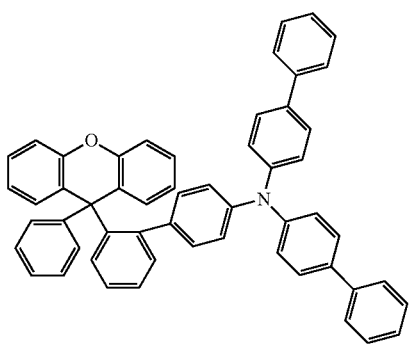 [SMILES: c1ccc(-c2ccc(N(c3ccc(-c4ccccc4)cc3)c3ccc(-c4ccccc4C4(c5ccccc5)c5ccccc5Oc5ccccc54)cc3)cc2)cc1]
| | |
|---|---|
| 4-6 | 69% |
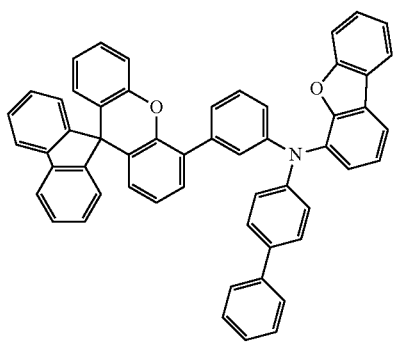 [SMILES: c1ccc(-c2ccc(N(c3cccc(-c4cccc5c4Oc4ccccc4C54c5ccccc5-c5ccccc54)c3)c3cccc4c3oc3ccccc34)cc2)cc1]
| | |
|---|---|
| 4-7 | 88% |
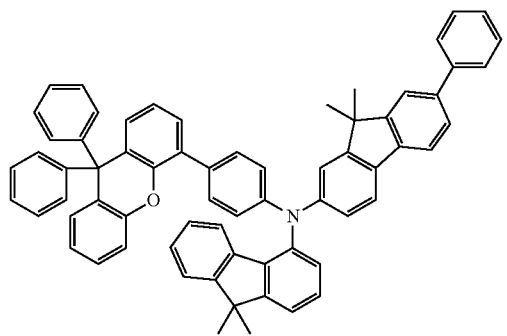 [SMILES: CC1(C)c2cc(-c3ccccc3)ccc2-c2ccc(N(c3ccc(-c4cccc5c4Oc4ccccc4C5(c4ccccc4)c4ccccc4)cc3)c3cccc4c3-c3ccccc3C4(C)C)cc21]

| | |
|---|---|
| 4-8 | 85% |
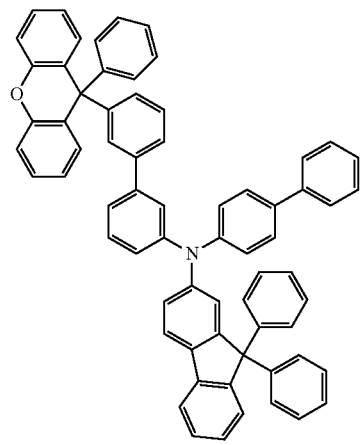 [SMILES: c1ccc(-c2ccc(N(c3cccc(-c4cccc(C5(c6ccccc6)c6ccccc6Oc6ccccc65)c4)c3)c3ccc4c(c3)C(c3ccccc3)(c3ccccc3)c3ccccc3-4)cc2)cc1]
| | |
|---|---|
| 4-9 | 75% |
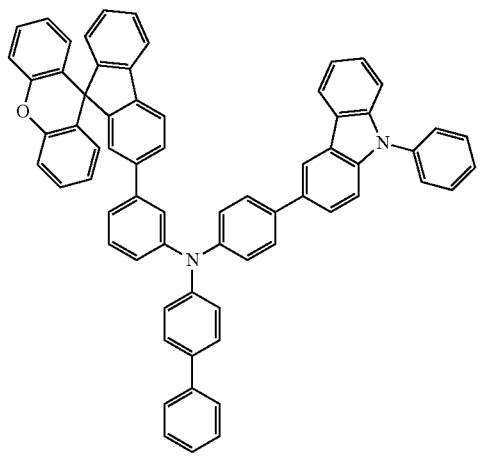 [SMILES: c1ccc(-c2ccc(N(c3ccc(-c4ccc5c(c4)c4ccccc4n5-c4ccccc4)cc3)c3cccc(-c4ccc5c(c4)C4(c6ccccc6Oc6ccccc64)c4ccccc4-5)c3)cc2)cc1]
| | |
|---|---|
| 4-10 | 75% |
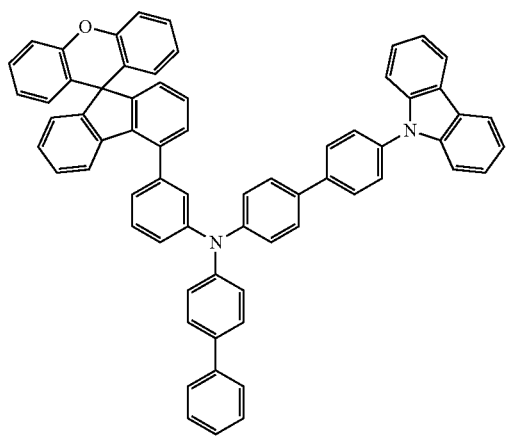 [SMILES: c1ccc(-c2ccc(N(c3ccc(-c4ccc(-n5c6ccccc6c6ccccc65)cc4)cc3)c3cccc(-c4cccc5c4-c4ccccc4C54c5ccccc5Oc5ccccc54)c3)cc2)cc1]

| 4-11 | 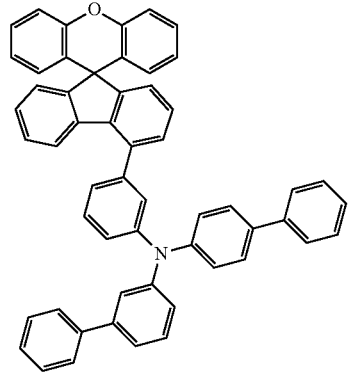 [SMILES: c1ccc(-c2ccc(N(c3cccc(-c4ccccc4)c3)c3cccc(-c4cccc5c4-c4ccccc4C54c5ccccc5Oc5ccccc54)c3)cc2)cc1] | 80% |

B) Device Examples

OLEDs according to the invention and OLEDs in accordance with the prior art are produced by a general process in accordance with WO 04/058911, which is adapted to the circumstances described here (layer-thickness variation, materials).

The data for various OLEDs are presented in the following examples E1 to E6 according to the invention and in Reference Examples V1 to V4. The substrates used are glass plates coated with structured ITO (indium tin oxide) in a thickness of 50 nm. The OLEDs have in principle the following layer structure: substrate/p-doped hole-transport layer (HTL1)/hole-transport layer (HTL2)/p-doped hole-transport layer (HTL3)/hole-transport layer (HTL4)/emission layer (EML)/electron-transport layer (ETL)/electron-injection layer (EIL) and finally a cathode. The cathode is formed by an aluminium layer with a thickness of 100 nm. The materials required for the production of the OLEDs are shown in Table 1, the various component structures are shown in Table 2.

All materials are applied by thermal vapour deposition in a vacuum chamber. The emission layer here always consists of at least one matrix material (host material) and an emitting dopant (emitter), which is admixed with the matrix material or matrix materials in a certain proportion by volume by co-evaporation. An expression such as H1:SEB1 (95%:5%) here means that material H1 is present in the layer in a proportion by volume of 95% and SEB1 is present in the layer in a proportion of 5%. Analogously, the electron-transport layer or hole-injection layer may also consist of a mixture of two materials.

The OLEDs are characterised by standard methods. For this purpose, the electroluminescence spectra, the current efficiency (measured in cd/A), the power efficiency (measured in lm/W) and the external quantum efficiency (EQE, measured in percent) as a function of the luminous density, calculated from current/voltage/luminous density characteristic lines (IUL characteristic lines) assuming Lambert emission characteristics, and the lifetime are determined. The electroluminescence spectra are determined at a luminous density of 1000 cd/m$^2$, and the CIE 1931 x and y color coordinates are calculated therefrom. The expression EQE @ 10 mA/cm$^2$ denotes the external quantum efficiency at a current density of 10 mA/cm$^2$. LT80 @ 50 mA/cm$^2$ is the lifetime by which the OLED has dropped to 80% of the initial intensity at an initial luminance at constant current of 50 mA/cm$^2$.

TABLE 1

Structures of the materials used

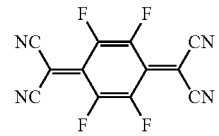 [SMILES: N#CC(C#N)=c1c(F)c(F)c(=C(C#N)C#N)c(F)c1F]

F4TCNQ

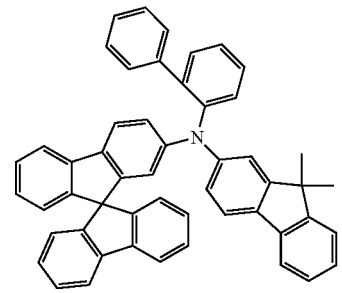 [SMILES: CC1(C)c2ccccc2-c2ccc(N(c3ccc4c(c3)C3(c5ccccc5-c5ccccc53)c3ccccc3-4)c3ccccc3-c3ccccc3)cc21]

HIL

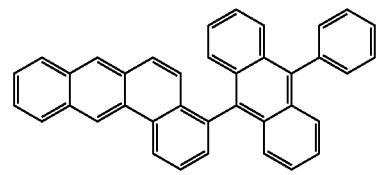 [SMILES: c1ccc(-c2c3ccccc3c(-c3cccc4c3ccc3cc5ccccc5cc34)c3ccccc23)cc1]

H1

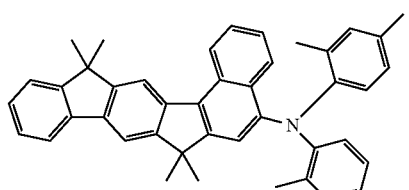

SEB

TABLE 1-continued
Structures of the materials used
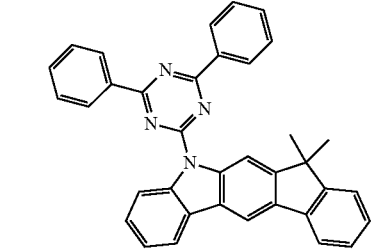 [SMILES: CC1(C)c2ccccc2-c2cc3c4ccccc4n(-c4nc(-c5ccccc5)nc(-c5ccccc5)n4)c3cc21]
H2
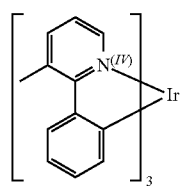
TEG
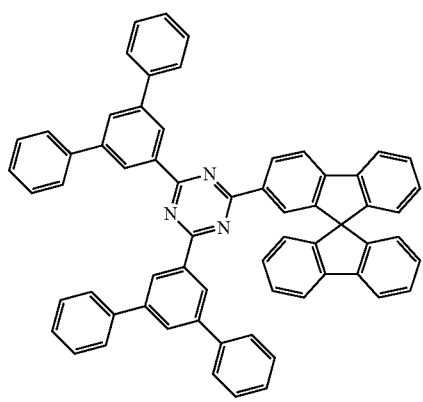 [SMILES: c1ccc(-c2cc(-c3ccccc3)cc(-c3nc(-c4cc(-c5ccccc5)cc(-c5ccccc5)c4)nc(-c4ccc5c(c4)C4(c6ccccc6-c6ccccc64)c4ccccc4-5)n3)c2)cc1]
ETM
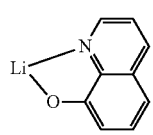
LiQ
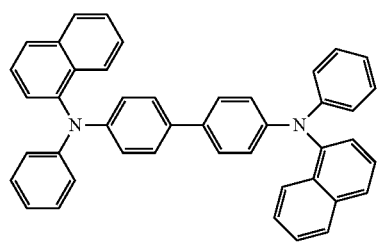 [SMILES: c1ccc(N(c2ccc(-c3ccc(N(c4ccccc4)c4cccc5ccccc45)cc3)cc2)c2cccc3ccccc23)cc1]
NPB
TABLE 1-continued
Structures of the materials used
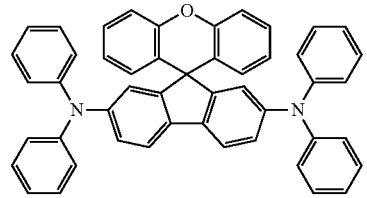 [SMILES: c1ccc(N(c2ccccc2)c2ccc3c(c2)C2(c4ccccc4Oc4ccccc42)c2cc(N(c4ccccc4)c4ccccc4)ccc2-3)cc1]
HTMV1
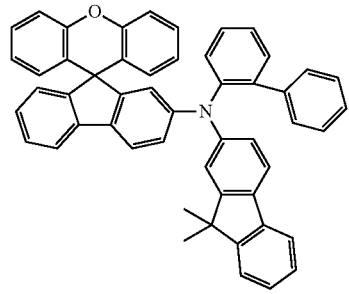 [SMILES: CC1(C)c2ccccc2-c2ccc(N(c3ccc4c(c3)C3(c5ccccc5Oc5ccccc53)c3ccccc3-4)c3ccccc3-c3ccccc3)cc21]
HTM1
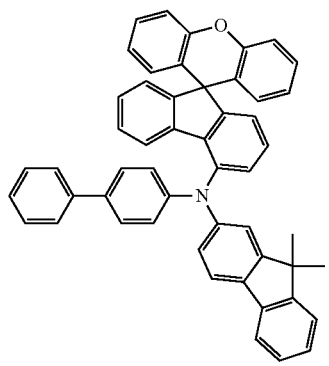 [SMILES: CC1(C)c2ccccc2-c2ccc(N(c3ccc(-c4ccccc4)cc3)c3cccc4c3-c3ccccc3C43c4ccccc4Oc4ccccc43)cc21]
HTM2
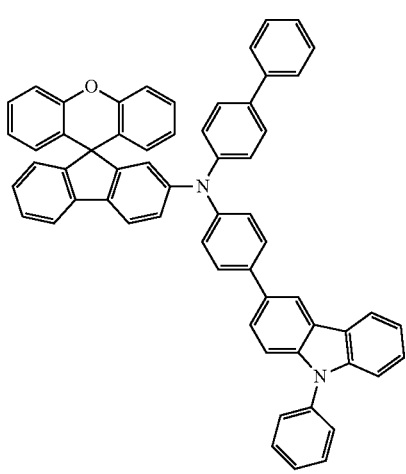 [SMILES: c1ccc(-c2ccc(N(c3ccc(-c4ccc5c(c4)c4ccccc4n5-c4ccccc4)cc3)c3ccc4c(c3)C3(c5ccccc5Oc5ccccc53)c3ccccc3-4)cc2)cc1]
HTM3

TABLE 1-continued

Structures of the materials used

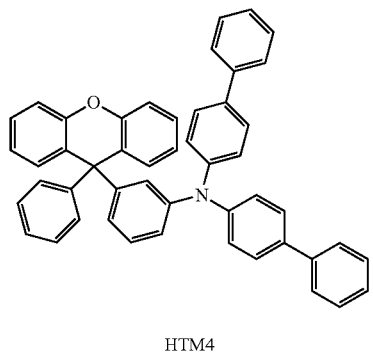

HTM4

Compounds HTM1, HTM2, HTM3 and HTM4 according to the invention are employed in the p-doped hole-transport layer HTL3 and the undoped hole-transport layer HTL4 in Examples E1 to E6 presented. This illustrates by way of example the use as hole-transporting material. Alternatively, other p-dopants can be used in combination with the compounds according to the invention. As a further alternative, the compounds according to the invention can be used in another hole-transporting layer or in other device structures. Hole-transport compounds from the prior art (compounds NPB or HTMV1) are employed instead of the compounds according to the invention in comparative devices V1 to V4.

Example 1 (Fluorescent OLEDs)

Compared with reference devices V1 and V2 (quantum efficiency 6.2% and 7.7%), the two devices E1 and E2 according to the invention exhibit a higher quantum efficiency at 10 mA/cm² of 8.0% and 8.4%. The lifetime LT80 at 50 mA/cm² is also significantly better in the case of devices E1 (225 h) and E2 (285 h) according to the invention than in the case of reference devices V1 (135 h) and V2 (30 h).

Example 2 (Phosphorescent OLEDs)

Reference devices V3 and V4 (quantum efficiency 11.7% and 19.8%) exhibit lower or approximately the same quantum efficiencies at 2 mA/cm² as devices E3 (quantum efficiency 20.4%) and E4 (quantum efficiency 19.9%) according to the invention. The lifetimes at 20 mA/cm² in the case of devices E3 (160 h) and E4 (215 h) according to the invention are also longer than in the case of comparative devices V3 (80 h) and V4 (140 h).

TABLE 2

Structure of the OLEDs

| Ex. | HTL1 Thickness/nm | HTL2 Thickness/nm | HTL3 Thickness/nm | HTL4 Thickness/nm | EML Thickness/nm | ETL Thickness/nm | EIL Thickness/nm |
|---|---|---|---|---|---|---|---|
| V1 | HIM1:F4TCNQ (3%) 20 nm | HIM1 155 nm | NPB:F4TCNQ (3%) 20 nm | NPB 20 nm | H1:SEB1(5%) 20 nm | ETM(50%):LiQ (50%) 30 nm | LiQ 1 nm |
| V2 | HIM1:F4TCNQ (3%) 20 nm | HIM1 155 nm | HTMV1:F4TCNQ (3%) 20 nm | HTMV1 20 nm | H1:SEB1(5%) 20 nm | ETM(50%):LiQ (50%) 30 nm | LiQ 1 nm |
| E1 | HIM1:F4TCNQ (3%) 20 nm | HIM1 155 nm | HTM1:F4TCNQ (3%) 20 nm | HTM1 20 nm | H1:SEB1(5%) 20 nm | ETM(50%):LiQ (50%) 30 nm | LiQ 1 nm |
| E2 | HIM1:F4TCNQ (3%) 20 nm | HIM1 155 nm | HTM2:F4TCNQ (3%) 20 nm | HTM2 20 nm | H1:SEB1(5%) 20 nm | ETM(50%):LiQ (50%) 30 nm | LiQ 1 nm |
| V3 | HIM1:F4TCNQ (3%) 20 nm | HIM1 210 nm | NPB:F4TCNQ (3%) 20 nm | NPB 20 nm | H2:TEG(10%) 30 nm | ETM(50%):LiQ (50%) 40 nm | LiQ 1 nm |
| V4 | HIM1:F4TCNQ (3%) 20 nm | HIM1 210 nm | HTMV1:F4TCNQ (3%) 20 nm | HTMV1 20 nm | H2:TEG(10%) 30 nm | ETM(50%):LiQ (50%) 40 nm | LiQ 1 nm |
| E3 | HIM1:F4TCNQ (3%) 20 nm | HIM1 210 nm | HTM1:F4TCNQ (3%) 20 nm | HTM1 20 nm | H2:TEG(10%) 30 nm | ETM(50%):LiQ (50%) 40 nm | LiQ 1 nm |
| E4 | HIM1:F4TCNQ (3%) 20 nm | HIM1 210 nm | HTM2:F4TCNQ (3%) 20 nm | HTM2 20 nm | H2:TEG(10%) 30 nm | ETM(50%):LiQ (50%) 40 nm | LiQ 1 nm |
| E5 | HIM1:F4TCNQ (3%) 20 nm | HIM1 155 nm | HTM3:F4TCNQ (3%) 20 nm | HTM3 20 nm | H1:SEB1(5%) 20 nm | ETM(50%):LiQ (50%) 30 nm | LiQ 1 nm |
| E6 | HIM1:F4TCNQ (3%) 20 nm | HIM1 210 nm | HTM4:F4TCNQ (3%) 20 nm | HTM4 20 nm | H2:TEG(10%) 30 nm | ETM(50%):LiQ (50%) 40 nm | LiQ 1 nm |

Example 3 (Fluorescent OLED)

OLED E5 according to the invention exhibits a similar or higher quantum efficiency of 7.5% at 10 mA/cm² compared with reference devices V1 and V2 (6.2% and 7.7%). The lifetime LT80 at 50 mA/cm² is better in the case of OLED E5 according to the invention (145 h) than in the case of reference devices V1 (135 h) and V2 (30 h).

Example 4 (Phosphorescent OLED)

Device E6 according to the invention exhibits a higher quantum efficiency (19.2%) at 2 mA/cm² than reference device V3 (11.7%).

In summary, the examples show the very good device data which are obtained on use of the compounds according to the invention as hole-transporting materials in OLEDs. Furthermore, the examples show improved device data compared with materials in accordance with the prior art.

The invention claimed is:
1. A compound of a formula (I)

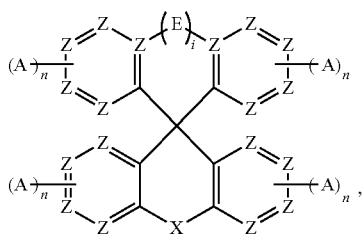

formula (I)

where:
- A is an arylamino group, optionally substituted by one or more radicals $R^1$, or a carbazole group, optionally substituted by one or more radicals $R^1$;
- E is a single bond;
- X is O or S;
- Z is on each occurrence, identically or differently, $CR^2$, where, in the case where a group A is bonded to it, the group Z is equal to C;
- $R^1$ is on each occurrence, identically or differently, H, D, F, Cl, Br, I, $C(=O)R^3$, CN, $Si(R^3)_3$, $N(R^3)_2$, $P(=O)(R^3)_2$, $S(=O)R^3$, $S(=O)_2R^3$, a straight-chain alkyl or alkoxy group having 1 to 20 C atoms or a branched or cyclic alkyl or alkoxy group having 3 to 20 C atoms or an alkenyl or alkynyl group having 2 to 20 C atoms, where the above-mentioned groups may each be substituted by one or more radicals $R^3$ and where one or more $CH_2$ groups in the above-mentioned groups is optionally replaced by $-R^3C=CR^3-$, $-C\equiv C-$, $Si(R^3)_2$, $C=O$, $C=NR^3$, $-C(=O)O-$, $-C(=O)NR^3-$, $NR^3$, $P(=O)(R^3)$, $-O-$, $-S-$, SO or $SO_2$ and where one or more H atoms in the above-mentioned groups is optionally replaced by D, F, Cl, Br, I or CN, or an aromatic or heteroaromatic ring system having 5 to 30 aromatic ring atoms, which may in each case be substituted by one or more radicals $R^3$, or an aryloxy or heteroaryloxy group having 5 to 30 aromatic ring atoms, which is optionally substituted by one or more radicals $R^3$, where two or more radicals $R^1$ are optionally linked to one another and may form a ring;
- $R^2$ is on each occurrence, identically or differently, H, D, F, CN, $Si(R^3)_3$, a straight-chain alkyl having 1 to 20 C atoms or a branched or cyclic alkyl or alkoxy group having 3 to 20 C atoms where the above-mentioned groups may each be substituted by one or more radicals $R^3$ and where one or more $CH_2$ groups in the above-mentioned groups is optionally replaced by $-R^3C=CR^3-$, $-C\equiv C-$, $Si(R^3)_2$, $C=O$, $C=NR^3$, $-C(=O)O-$, $-S-$ or $-C(=O)NR^3-$, or an aromatic or heteroaromatic ring system having 5 to 20 aromatic ring atoms, which may in each case be substituted by one or more radicals $R^3$, where two or more radicals $R^2$ are optionally linked to one another and may form a ring;
- $R^3$ is on each occurrence, identically or differently, H, D, F, a straight-chain alkyl group having 1 to 20 C atoms or a branched or cyclic alkyl or alkoxy group having 3 to 20 C atoms where the above-mentioned groups may each be substituted by one or more radicals $R^4$ and where one or more $CH_2$ groups in the above-mentioned groups is optionally replaced by $-R^4C=CR^4-$, $-C\equiv C-$, $Si(R^4)_2$, $C=O$, $C=NR^4$, $-C(=O)O-$, $-S-$ or $-C(=O)NR^4-$, or an aromatic or heteroaromatic ring system having 5 to 20 aromatic ring atoms, which may in each case be substituted by one or more radicals $R^4$, where two or more radicals $R^3$ are optionally linked to one another and may form a ring;
- $R^4$ is on each occurrence, identically or differently, H, D, F or an aliphatic radical having 1 to 20 C atoms, aromatic ring having 6 to 20 C atoms or heteroaromatic organic radical having 5 to 20 C atoms in which, in addition, one or more H atoms is optionally replaced by D or F; two or more substituents $R^4$ here are optionally linked to one another and may form a ring;
- i is equal to 0 or 1; and
- n is on each occurrence, identically or differently, 0 or 1, where the sum of all the indices n is equal to 1.

2. The compound according to claim 1, wherein the group A is an arylamino group, which is optionally substituted by one or more radicals $R^1$.

3. The compound according to claim 1, wherein the compound contains only a single amino group.

4. The compound according to claim 1, wherein X is equal to O.

5. The compound according to claim 1, wherein the compound of the formula (I) conforms to one of the formulae (I-1) to (I-8)

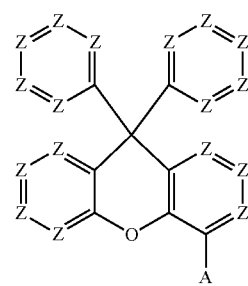

formula (I-1)

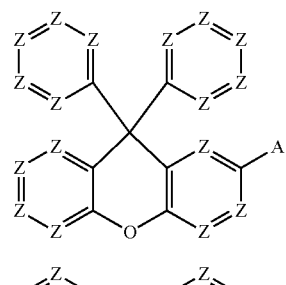

formula (I-2)

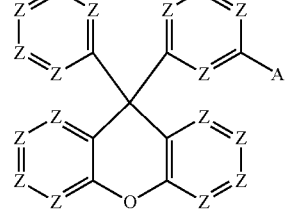

formula (I-3)

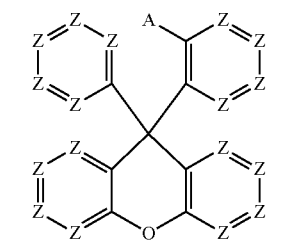

formula (I-4)

-continued formula (I-5)

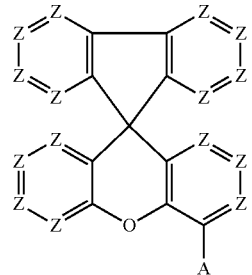

formula (I-6)

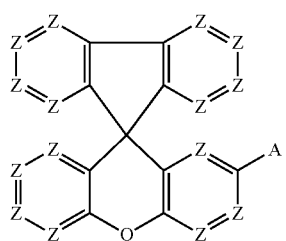

formula (I-7)

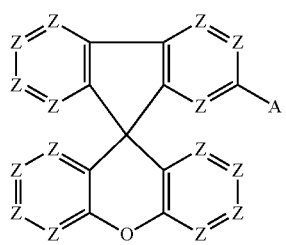

-continued formula (I-8)

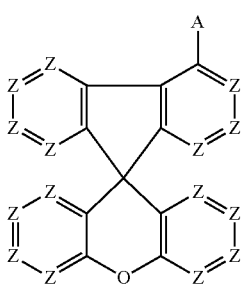

where the symbols occurring are as defined in claim 1.

6. An oligomer, polymer or dendrimer containing one or more compounds of the formula (I) according to claim 1, where the bond(s) to the polymer, oligomer or dendrimer is optionally localised at any position in formula (I) that are substituted by $R^1$ or $R^2$.

7. A formulation comprising at least one compound of the formula (I) according to claim 1 and at least one solvent.

8. A formulation comprising at least one polymer, oligomer or dendrimer according to claim 6 and at least one solvent.

9. Electronic device comprising at least one compound of the formula (I) according to claim 1.

10. The electronic device according to claim 9, wherein the device is selected from the group consisting of organic integrated circuit (OIC), organic field-effect transistor (OFET), organic thin-film transistor (OTFT), organic light-emitting transistor (OLET), organic solar cell (OSC), organic optical detector, organic photoreceptor, organic field-quench device (OFQD), organic light-emitting electrochemical cell (OLEC), organic laser diode (O-laser) and organic electroluminescent device (OLED).

11. An organic electroluminescent device which comprises the compound of the formula (I) according to claim 1, which is present in a hole-transport layer, an electron-blocking layer, a hole-injection layer or in an emitting layer.

* * * * *

UNITED STATES PATENT AND TRADEMARK OFFICE
CERTIFICATE OF CORRECTION

PATENT NO. : 9,978,949 B2
APPLICATION NO. : 14/441975
DATED : May 22, 2018
INVENTOR(S) : Teresa Mujica-Fernaud et al.

It is certified that error appears in the above-identified patent and that said Letters Patent is hereby corrected as shown below:

On the Title Page

Please replace the title page with the attached title page showing the corrected number of claims.

In the Claims

Please add the following claims:

12. The compound according to Claim 1, wherein $R^1$ is on each occurrence, identically or differently, H, D, F, CN, $Si(R^3)_3$, a straight-chain alkyl or alkoxy group having 1 to 20 C atoms or a branched or cyclic alkyl or alkoxy group having 3 to 20 C atoms, where the above-mentioned groups may each be substituted by one or more radicals $R^3$ and where one or more $CH_2$ groups in the above-mentioned groups may be replaced by -C≡C-, -$R^3$C= $CR^3$ - , $Si(R^3)_2$, C=O, C=$NR^3$, -$NR^3$-, -O-, -S-, - C(=O)O- or -C(= O)$NR^{3-}$, or an aromatic or heteroaromatic ring system having 5 to 20 aromatic ring atoms, which may in each case be substituted by one or more radicals $R^3$.

13. The compound according to Claim 11, wherein A is of the formula

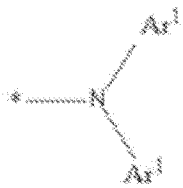

wherein
$Ar^1$ is on each occurrence, identically or differently, an aromatic ring having 6 to 30 aromatic ring atoms, which is optionally substituted by one or more radicals $R^1$.

Signed and Sealed this
Twenty-seventh Day of August, 2024

Katherine Kelly Vidal
*Director of the United States Patent and Trademark Office*

14. The compound according to Claim 13, wherein $Ar^1$ is an aromatic ring having 6 to 24 aromatic ring atoms, which is optionally substituted by one or more radicals $R^1$.

15. The compound according to Claim 13, wherein $Ar^1$ is phenyl, biphenyl, naphthyl, terphenyl, fluorenyl, spirobifluorene or indenofluorenyl, each of which is optionally substituted by one or more radicals $R^1$.

16. The compound according to Claim 15, wherein $R^1$ is on each occurrence, identically or differently, H, D, F, CN, $Si(R^3)_3$, a straight-chain alkyl or alkoxy group having 1 to 20 C atoms or a branched or cyclic alkyl or alkoxy group having 3 to 20 C atoms, where the above-mentioned groups may each be substituted by one or more radicals $R^3$ and where one or more $CH_2$ groups in the above-mentioned groups may be replaced by -C≡C-, $-R^3C=CR^3$-, $Si(R^3)_2$, C=O, $C=NR^3$, $-NR^3$-, -O-, -S-, -C(=O)O- or $-C(=O)NR^{3-}$, or an aromatic or heteroaromatic ring system having 5 to 20 aromatic ring atoms, which may in each case be substituted by one or more radicals $R^3$.

17. The compound according to Claim 1, wherein A is a carbazole group, optionally substituted by one or more radicals $R^1$.

(12) United States Patent
Mujica-Fernaud et al.

(10) Patent No.: US 9,978,949 B2
(45) Date of Patent: May 22, 2018

(54) MATERIALS FOR ELECTRONIC DEVICES

(71) Applicant: Merck Patent GmbH, Darmstadt (DE)

(72) Inventors: Teresa Mujica-Fernaud, Darmstadt (DE); Elvira Montenegro, Weinheim (DE); Frank Voges, Bad Duerkheim (DE); Jonas Valentin Kroeber, Frankfurt am Main (DE); Philipp Stoessel, Frankfurt am Main (DE)

(73) Assignee: Merck Patent GmbH (DE)

( * ) Notice: Subject to any disclaimer, the term of this patent is extended or adjusted under 35 U.S.C. 154(b) by 171 days.

(21) Appl. No.: 14/441,975

(22) PCT Filed: Oct. 18, 2013

(86) PCT No.: PCT/EP2013/003136
§ 371 (c)(1),
(2) Date: May 11, 2015

(87) PCT Pub. No.: WO2014/072017
PCT Pub. Date: May 15, 2014

(65) Prior Publication Data
US 2015/0295181 A1    Oct. 15, 2015

(30) Foreign Application Priority Data
Nov. 12, 2012   (EP) .................... 12007665

(51) Int. Cl.
| | |
|---|---|
| *H05B 33/20* | (2006.01) |
| *H01L 51/50* | (2006.01) |
| *C09K 11/06* | (2006.01) |
| *C07D 409/12* | (2006.01) |
| *C07D 405/12* | (2006.01) |
| *C07D 311/96* | (2006.01) |
| *C07D 311/90* | (2006.01) |
| *H01L 51/00* | (2006.01) |
| *C08G 73/02* | (2006.01) |
| *C08G 75/00* | (2006.01) |

(52) U.S. Cl.
CPC ........ *H01L 51/0061* (2013.01); *C07D 311/90* (2013.01); *C07D 311/96* (2013.01); *C07D 405/12* (2013.01); *C07D 409/12* (2013.01); *C08G 73/0273* (2013.01); *C08G 75/00* (2013.01); *C09K 11/06* (2013.01); *H01L 51/006* (2013.01); *H01L 51/0052* (2013.01); *H05B 33/20* (2013.01); *C09K 2211/1011* (2013.01); *C09K 2211/1014* (2013.01); *H01L 51/0072* (2013.01); *H01L 51/0073* (2013.01); *H01L 51/0074* (2013.01); *H01L 51/0085* (2013.01); *H01L 51/0087* (2013.01); *H01L 51/5012* (2013.01); *H01L 51/5056* (2013.01); *H01L 51/5096* (2013.01); *Y02E 10/549* (2013.01)

(58) Field of Classification Search
CPC combination set(s) only.
See application file for complete search history.

(56) References Cited

U.S. PATENT DOCUMENTS

| | | |
|---|---|---|
| 5,387,725 A | 2/1995 | Walters et al. |
| 9,368,733 B2 | 6/2016 | Ryu et al. |
| 2003/0168970 A1 | 9/2003 | Tominaga et al. |

FOREIGN PATENT DOCUMENTS

| | | | |
|---|---|---|---|
| CN | 1397148 A | 2/2003 | |
| CN | 101440082 A | 5/2009 | |
| CN | 102229623 A | 11/2011 | |
| JP | H07502728 A | 3/1995 | |
| JP | 2002222697 A | 8/2002 | |
| JP | 2009191232 A | 8/2009 | |
| JP | 4843889 B2 | 12/2011 | |
| JP | 2016502500 A | 1/2016 | |
| KR | 20080037699 A | 4/2008 | |
| KR | 20120116838 A | 10/2012 | |
| KR | 20130007390 A * | 1/2013 | |
| KR | 20130140303 A | 12/2013 | |
| WO | WO 9309074 A2 * | 5/1993 | ............ C07B 37/04 |
| WO | WO-2014051232 A1 | 4/2014 | |

OTHER PUBLICATIONS

Chu et al. "Synthesis of spiro[fluorene-9,9'-xanthene] derivatives and their application as hole-transporting materials for organic light-emitting devices" Synth. Met. 2012 162, 614-620.*
Goodbrand et al. "Ligand-Accelerated Catalysis of the Ullmann Condensation: Application to Hole Conducting Trlarylamlnes" J. Org. Chem. 1999, 64, 670-674.*
Kim et al. KR 20130007390 A English Machine Translation [retrieved on Feb. 16, 2017]. Retrieved from KIPO.*
Qian, Y., et al., "A new spiro[fluorene-9,9'-xanthene]-based host material possessing no conventional hole- and electron-transporting units for efficient and low voltage blue PHOLED via simple two-step synthesis", Organic Electronics, 2012, vol. 13, pp. 22741-22746.
International Search Report for PCT/EP2013/003136 dated Dec. 13, 2013.
Japanese Office Action for Japanese Application No. 2015/541029, dated Jul. 11, 2017.

\* cited by examiner

*Primary Examiner* — Amanda L Aguirre
(74) *Attorney, Agent, or Firm* — Drinker Biddle & Reath LLP

(57)   ABSTRACT

The application relates to a compound of a formula (I) which is suitable for use as functional material in electronic devices.

17 Claims, No Drawings